US007189705B2

(12) United States Patent
Lam et al.

(10) Patent No.: US 7,189,705 B2
(45) Date of Patent: Mar. 13, 2007

(54) METHODS OF ENHANCING SPLP-MEDIATED TRANSFECTION USING ENDOSOMAL MEMBRANE DESTABILIZERS

(75) Inventors: Angela M. I. Lam, Vancouver (CA); Lorne R. Palmer, Vancouver (CA); Pieter R. Cullis, Vancouver (CA)

(73) Assignee: The University of British Columbia, Vancouver (CA)

( * ) Notice: Subject to any disclaimer, the term of this patent is extended or adjusted under 35 U.S.C. 154(b) by 446 days.

(21) Appl. No.: 09/839,707

(22) Filed: Apr. 20, 2001

(65) Prior Publication Data

US 2002/0072121 A1 Jun. 13, 2002

Related U.S. Application Data

(63) Continuation-in-part of application No. 09/553,639, filed on Apr. 20, 2000.

(60) Provisional application No. 60/227,949, filed on Aug. 25, 2000.

(51) Int. Cl.
*A61K 48/00* (2006.01)

(52) U.S. Cl. .................... 514/44; 424/450; 435/320.1; 435/455; 435/458

(58) Field of Classification Search .................. 514/44; 435/320.1, 455, 458; 424/450
See application file for complete search history.

(56) References Cited

U.S. PATENT DOCUMENTS

| | | | | |
|---|---|---|---|---|
| 4,885,172 | A | 12/1989 | Bally et al. | |
| 5,059,421 | A | 10/1991 | Loughrey et al. | |
| 5,171,578 | A | 12/1992 | Bally et al. | |
| 5,208,036 | A | 5/1993 | Eppstein et al. | |
| 5,264,423 | A | 11/1993 | Cohen et al. | |
| 5,264,618 | A | 11/1993 | Felgner et al. | |
| 5,276,019 | A | 1/1994 | Cohen et al. | |
| 5,279,833 | A | 1/1994 | Rose | |
| 5,283,185 | A | 2/1994 | Epand et al. | |
| 5,534,259 | A | 7/1996 | Zalipsky et al. | 424/450 |
| 5,639,473 | A | 6/1997 | Grinstaff et al. | 424/450 |
| 5,766,902 | A | 6/1998 | Craig et al. | 435/172.3 |
| 5,837,282 | A | 11/1998 | Fenske et al. | |
| 5,846,530 | A | 12/1998 | Soon-Shiong et al. | 424/93.7 |
| 5,876,695 | A | 3/1999 | Gries et al. | |
| 5,885,613 | A | 3/1999 | Holland et al. | |
| 5,976,567 | A | 11/1999 | Wheeler et al. | |
| 5,981,501 | A | 11/1999 | Wheeler et al. | |
| 6,177,274 | B1 * | 1/2001 | Park | 435/455 |
| 6,210,707 | B1 * | 4/2001 | Papahadjopoulos | 424/450 |
| 6,245,530 | B1 * | 6/2001 | Alitalo | 435/69.1 |
| 6,270,761 | B1 * | 8/2001 | Russell | 424/93.21 |
| 6,271,208 | B1 * | 8/2001 | Bischoff | 514/44 |
| 6,284,267 | B1 | 9/2001 | Aneja | 424/450 |
| 6,287,591 | B1 * | 9/2001 | Semple | 424/450 |
| 6,300,317 | B1 | 10/2001 | Szoka, Jr. et al. | 514/44 |
| 6,316,024 | B1 * | 11/2001 | Allen | 424/450 |
| 6,320,017 | B1 * | 11/2001 | Ansell | 528/310 |
| 6,395,254 | B1 | 5/2002 | Sinn et al. | 424/1.69 |
| 6,410,049 | B1 * | 6/2002 | Papahadjopoulos | 424/450 |
| 6,413,941 | B1 * | 7/2002 | Garnett | 514/44 |
| 2002/0022264 | A1 * | 2/2002 | Sullivan | 435/320.1 |

FOREIGN PATENT DOCUMENTS

| | | | |
|---|---|---|---|
| CA | 2271582 | | 11/1999 |
| WO | WO 96/40964 | A2 | 12/1996 |
| WO | WO 97/38010 | A2 | 10/1997 |
| WO | WO 98/16202 | A2 | 4/1998 |
| WO | WO 98/19710 | * | 5/1998 |
| WO | WO 98/46208 | A1 | 10/1998 |
| WO | WO 98/51285 | A2 | 11/1998 |
| WO | WO 99/05094 | A1 | 2/1999 |
| WO | WO 99/05303 | A1 | 2/1999 |
| WO | WO 99/08997 | | 2/1999 |
| WO | WO 99/65461 | A2 | 12/1999 |
| WO | WO/0003738 | * | 1/2000 |
| WO | WO 00/06120 | A1 | 2/2000 |
| WO | WO 00/41647 | * | 7/2000 |
| WO | WO 00/43043 | A1 | 7/2000 |
| WO | WO 00/62813 | A2 | 10/2000 |
| WO | WO 01/05373 | A1 | 1/2001 |

OTHER PUBLICATIONS

Haberland (Biochimica et Biophysica Acta 1445, 21-30, Apr. 14, 1999).*
Lam, J. of Liposome Res., Feb. 1998, vol. 8, No. 1, pp. 75-76.*
Huang, Biomedical Engineering, Dec. 25, 2000, 12/6, pp. 281-287.*
Lam, Biochimica et Biophysica Acta, Feb. 2000, 1463, 2, pp. 279-290.*
Mozafari, J. Microencapsulation, vol. 15, pp. 55-65, 1998.*
Anwer et al., *J. of Drug Targeting*, 8(2):125-135 (2000).
Barron et al., *Gene Ther.*, 6:1179-1183 (1999).
Bennett et al., *Mol. Pharmacol.*, 41:1023-1033 (1992).
Bhattachary et al., *Tetrahedron Letters*, 40:8167-8171 (1999).
Bottger et al., *Biochimica et Biophysica Acta*, 1395:78-87 (1998).
Chen et al., *Bioconj. Chem.*, 11:433-437 (2000).
Chonn et al., *Current Opinion in Biotechnology*, 6:698-708 (1995).
Cullis et al., *Biochimica et Biophysica Acta*, 559:399-420 (1979).
Drummond, *Dissertation Abstracts Online, Part B*, 59(2):673 (1997).

(Continued)

*Primary Examiner*—Joseph Woitach
*Assistant Examiner*—Robert M. Kelly
(74) *Attorney, Agent, or Firm*—Seed IP Law Group PLLC

(57) ABSTRACT

The present invention provides novel and surprisingly effective methods for delivering nucleic acids to cells. These methods are based upon the discovery that the presence of endosomal membrane destabilizers (e.g., calcium) leads to a dramatic increase in the transfection efficiency of plasmids formulated as SPLP, or "stabilized plasmid-lipid particles."

62 Claims, 23 Drawing Sheets

OTHER PUBLICATIONS

Edwards et al., *Biophys. J.*, 73:258-266 (1997).
Felgner et al., *Journal of Biological Chemistry*, 269(4):2550-2561 (1994).
Felgner et al., *Proc. Natl. Acad. Sci. USA*, 84:7413-7417 (1987).
Felgner, *Scientific American*, 276:102-106 (1997).
Fenske et al., *Biochimica et Biophysica Acta*, 1512:259-272 (2001.
Haberland et al., *Biochimica et Biophysica Acta*, 1445:21-30 (1999).
Hafez, *Dissertation Abstracts Online, Part B*, 61(12):6350 (2000).
Harrison et al., *Biotechniques*, 19:816-823 (1995).
Hofland et al., *Pharmaceutical Research*, 14(6):742-749 (1997).
Hope et al., *FEBS Letters*, 107(2):323-326 (1979).
Hope et al., *Molecular Membrane Biology*, 15:1-14 (1998).
Hristova et al., *Macromolecules*, 28:7693-7699 (1995).
Huang et al., *Nature Biotechnology*, 15:620-621 (1997).
Kenworthy et al., *Biophys. J.*, 68:1903-1920 (1995).
Lam et al., *Biochim Biophys Acta*, 1463:279-290 (2000).
Loyter et al., *Proc. Natl. Acad. Sci. USA*, 79:422-426 (1982).
Miller et al., *Biochemistry*, 37:12875-12883 (1998).
Mislick et al., *Proc. Natl. Acad. Sci. USA*, 93:12349-12354 (1996).
Mok et al., *Biochimica et Biophysica Acta*, 1419:137-150 (1999).
Monck et al., *J. Drug Targ.*, 7(6):439-452 (2000).
Mori et al., *J. of Liposome Research*, 8(2):195-211 (1998).
Mounkes et al., *J. Biol. Chem.*, 273(40):26164-26170 (1998).
Orriantia et al., *Experimental Cell Research*, 190:170-174 (1990).
Ouahabi et al., *FEBS Letters* 414:187-192 (1997).
Pedroso De Lima et al., *Mol. Membrane Biology*, 16:103-109 (1999).
Peeters et al., *Human Gene Therapy*, 7:1693-1699 (1996).
Sheth et al., *Proc. Natl. Acad. Sci. USA*, 94:8399-8404 (1997).
Stein et al., *Science*, 261:1004-1011 (1993).
Templeton et al., *Nature Biotechnology*, 15:647-652 (1997).
Tilcock et al., *Biochemistry*, 23:2696-2703 (1984).
Tilcock et al., *Biochimica et Biophysica Acta*, 641:189-201 (1981).
Uduehi et al., *Pharmaceutical Research*, 16(12):1805-1811 (1999).
Uster et al., *FEBS Lett.*, 386:243-246 (1996).
Van Der Woude et al., *Biochim Biophys Acta*, 1240:34-40 (1995).
Wattiaux et al., *FEBS Letters*, 417:199-202 (1997).
Wheeler et al., *Gene Therapy*, 6:271-281 (1999).
Woodle et al., *Biochim. Biophys. Acta*, 1113:171-199 (1992).
Worgall et al., *Human Gene Therapy*, 8:37-44 (1997).
Xu et al., *Biochemistry*, 35:5616-5623 (1996).
Yei et al., *Gene Therapy*, 1:192-200 (1994).
Zalipsky et al., *FEBS Letters*, 353:71-74 (1994).
Zhang et al., *Gene Therapy*, 6:1438-1447 (1999).
Haselgruber, T., et al., "Synthesis and applications of a new poly-(ethylene glycol) derivative for the crosslinking of amines with thiols," *Bioconjug Chem.*6(3):242-8, May-Jun. 1995.
Jagur-Grodzinski, J., et al., "Biomedical Application of Functional Polymers," *Reactive and Functional Polymers*, 39(2):99-138, Feb. 15, 1999.
Macian, M., et al., "Preliminary Studies of the Toxic Effects of Non-ionic Surfactants Derived from Lysine," *Toxicolgy*, 106(1-3):1-9, Jan. 8, 1996.
Nathan, A., et al., "Copolymers of Lysine and Polyethylene Glycol: A New Family of Functionalized Drug Carriers," *Bioconjug Chem.*, 4(1):54-62, Jan.-Feb. 1993.
Toncheva, V., et al., "Block Copolymers with pH-Dependent Secondary Structure," *Journal of Controlled Release*, 48(2-3):301-302, Oct. 1997.
Trubetskoy, V., et al., "New Approaches in the Chemical Design of Gd-Containing Liposomes for Use in Magnetic Resonance Imaging of Lymph Nodes," *Journal of Liposome Research*, 4(2):961-980, 1994. XP000619021.
Trubetskoy, V., et al., "New Approaches in the Chemical Design of Gd-Containing Liposomes for Use in Magnetic Resonance Imaging of Lymph Nodes," *Journal of Liposome Research*, 4(2):961-983, 1994. XP000978705.
Weissig, V., et al., "Long-circulating Gadolinium-loaded Liposomes: Potential Use for Magnetic Resonance Imaging of the Blood Pool," *Colloids Surf B Biointerfaces*, 18(3-4):293-299, Oct. 1, 2000.

* cited by examiner

DSPE-CPL-1

DSPE-CPL-2

DSPE-CPL-2

DSPE-CPL-4

DSPE-CPL-8

METHODS OF ENHANCING SPLP-MEDIATED TRANSFECTION USING ENDOSOMAL MEMBRANE DESTABILIZERS

CROSS-REFERENCES TO RELATED APPLICATIONS

The present application claims priority to U.S. Provisional Patent Application No. 60/227,949, filed Aug. 25, 2000, the teachings of which are incorporated herein by reference for all purposes. The present application is a continuation-in-part of and claims the benefits of U.S. patent application Ser. No. 09/553,639 and PCT International Application No. 00/00451, both filed on Apr. 20, 2000, the teachings of which are incorporated herein by reference for all purposes.

BACKGROUND OF THE INVENTION

An effective and safe gene delivery system is required for gene therapy to be clinically useful. Viral vectors are relatively efficient gene delivery systems, but suffer from a variety of limitations, such as the potential for reversion to the wild type as well as immune response concerns. As a result, nonviral gene delivery systems are receiving increasing attention (Worgall, et al., *Human Gene Therapy* 8:37–44 (1997); Peeters, et al., *Human Gene Therapy* 7:1693–1699 (1996); Yei, et al., *Gene Therapy* 1:192–200 (1994); Hope, et al, *Molecular Membrane Biology* 15:1–14 (1998)). Plasmid DNA-cationic liposome complexes are currently the most commonly employed nonviral gene delivery vehicles (Felgner, *Scientific American* 276:102–106 (1997); Chonn, et al., *Current Opinion in Biotechnology* 6:698–708 (1995)). However, complexes are large, poorly defined systems that are not suited for systemic applications and can elicit considerable toxic side effects (Harrison, et al., *Biotechniques* 19:816–823 (1995); Huang, et al., *Nature Biotechnology* 15:620–621 (1997); Templeton, et al., *Nature Biotechnology* 15:647–652 (1997); Hofland, et al., *Pharmaceutical Research* 14:742–749 (1997)).

Recent work has shown that plasmid DNA can be encapsulated in small (~70 nm diameter) "stabilized plasmid-lipid particles" (SPLP) that consist of a single plasmid encapsulated within a bilayer lipid vesicle (Wheeler, et al., *Gene Therapy* 6:271–281 (1999)). These SPLPs typicaly contain the "fusogenic" lipid dioleoylphosphatidylethanolamine (DOPE), low levels of cationic lipid, and are stabilized in aqueous media by the presence of a poly(ethylene glycol) (PEG) coating. SPLP have systemic application as they exhibit extended circulation lifetimes following intravenous (i.v.) injection, accumulate preferentially at distal tumour sites due to the enhanced vascular permeability in such regions, and can mediate transgene expression at these tumour sites. The levels of transgene expression observed at the tumour site following i.v. injection of SPLP containing the luciferase marker gene are superior to the levels that can be achieved employing plasmid DNA-cationic liposome complexes (lipoplexes) or naked DNA. Still, improved levels of expression may be required for optimal therapeutic benefit in some applications (see, e.g., Monck, et al., *J. Drug Targ.* 7:439–452 (2000)).

Cationic poly(ethylene glycol) (PEG) lipids, or CPLs, have been designed for insertion into lipid bilayers to impart a positive charge(see, Chen, et al., *Bioconj. Chem.* 11:433–437 (2000)). For example, CPL containing distearoyl-PE (DSPE) coupled to PEG containing one or more distal positive charges were synthesized, and shown to promote enhanced in vitro cellular binding and uptake of liposomes (Chen, et al., *Bioconj. Chem.* 11:433–7 (2000)).

Thus, there remains a strong need in the art for novel and more efficient methods for introducing nucleic acids into cells. The present invention addresses this and other needs.

SUMMARY OF THE INVENTION

The present invention provides effective compositions, methods and uses for delivering nucleic acids to cells. The inventive compositions and methods are based upon the surprising discovery that the presence of an endosomal membrane destabilizer in a lipid formulation leads to a dramatic increase in transfection efficiency. The present compositions and methods can be used in vitro or in vivo, and can be used to increase the transfection efficiency of any cell type, including mammalian cells (e.g., human).

As such, in one embodiment, the present invention provides a nucleic acid-lipid particle composition for introducing a nucleic acid into a cell comprising: a cationic lipid, a conjugated lipid that inhibits aggregation of particles, a nucleic acid and an endosomal membrane destabilizer. In preferred aspects, the nucleic acid-lipid particles are "stabilized plasmid-lipid particles" (SPLP). Typically, SPLP are less than 150 nm in diameter and comprise a single plasmid encapsulated within a bilayer lipid vesicle. The conjugated lipid that inhibits aggregation typically comprises a hydrophilic polymer. In preferred embodiments, the hydrophilic polymer is a PEG or polyamide (e.g., ATTA) having a molecular weight of about 250 to about 7000 daltons. The endosomal membrane destabilizer can be inside the particle, outside the particle, or both inside and outside the particle. Preferably, the endosomal membrane destabilizer is $Ca^{++}$ ion. In certain aspects, the concentration of $Ca^{++}$ ion is from about 0.1 mM to about 100 mM.

In certain embodiments, the conjugated lipid that inhibits aggregation is a "cationic polymer lipid" (CPL). In preferred aspects, the CPL has the formula

A-W-Y     I

In Formula I, A is a lipid moiety, W is a hydrophilic polymer; and Y is a polycationic moiety. In certain preferred embodiments, Y is selected from lysine, arginine, asparagine, glutamine, and combinations thereof.

In another embodiment, the present invention provides a method for introducing a nucleic acid into a cell, comprising contacting the cell with a nucleic acid-lipid particle composition, wherein the particle comprises a cationic lipid, a conjugated lipid that inhibits aggregation of particles, a nucleic acid; and an endosomal membrane destabilizer. The endosomal membrane destabilizer can be inside the particle, outside the particle, or both inside and outside the particle. In certain embodiments, the endosomal membrane destabilizer contacts the cell before the particle, after the particle, simultaneously or combinations thereof.

In still another embodiment, the present invention provides a method for inducing $H_{II}$ phase structure in a lipid bilayer, comprising contacting the lipid bilayer with an endosomal membrane destabilizer, thereby inducing $H_{II}$ phase structure in the lipid bilayer. In certain aspects, the endosomal membrane destabilizer (e.g., $Ca^{++}$ ion) acts synergistically or additively with low levels of the cationic lipid to trigger $H_{II}$ phase formation.

The present compositions, methods and uses offer numerous advantages. For example, the presence of an endosomal membrane destabilizer leads to a dramatic increase in the transfection efficiency of nucleic acids. By increasing transfection efficiency, the amount of gene product within the cell is greatly increased. Moreover, the present compositions and methods can be used in vitro or in vivo, and can be used to increase the transfection efficiency of any cell type, including human.

These and other advantages, objects and embodiments of the present invention, will be described in more detail in conjunction with the following figures and the detailed description.

DETAILED DESCRIPTION OF THE INVENTION AND PREFERRED EMBODIMENTS

I. Introduction

Figure 1:
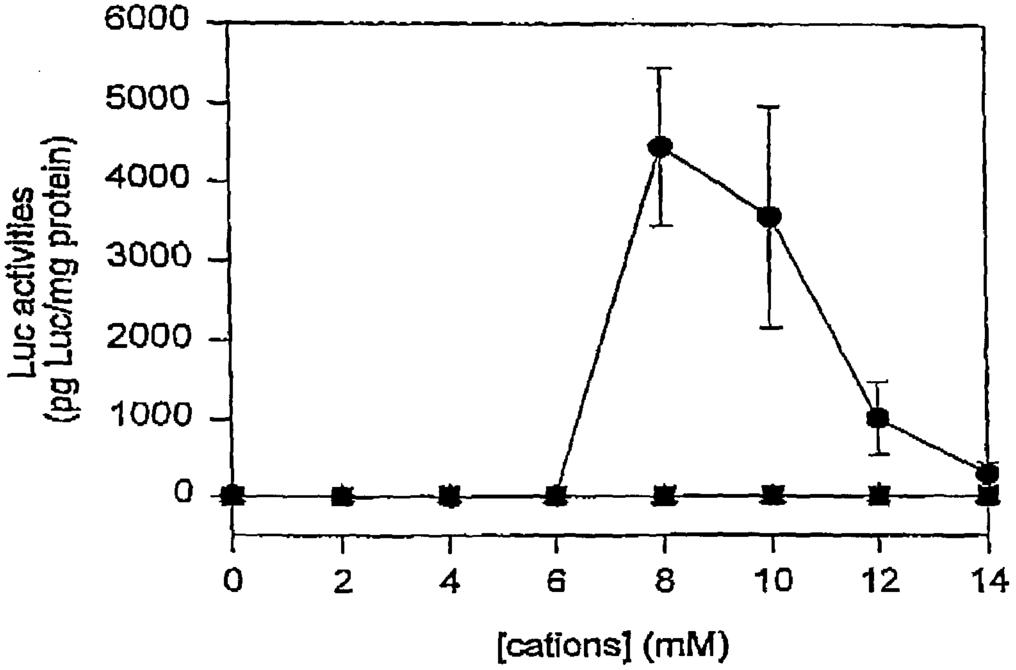
FIG. 1. Effect and specificity of $Ca^{2+}$ on SPLP transfection. Increasing concentrations of $CaCl_2$ (●), $MgCl_2$ (■), or NaCl (▲) (0 to 14 mM) were titrated into SPLP prior to their addition to cells. 0.5 μg of pCMVLuc plasmid encapsulated in SPLP (DODAC/DOPE/PEG-CerC20; 7:83:10 mol/mol/mol) vesicles was used to transfect cells plated at $1\times10^4$ cells/well of 96-well plates. Cells were incubated with SPLP for 24 h, and Luc activity was measured as described in Materials and Methods, Exampl I. All experiments were performed in triplicate.

The present invention provides novel and surprisingly effective compositions and methods for delivering nucleic acids to cells. These compositions and methods are based upon the discovery that the presence of an endosomal membrane destabilizer (e.g., calcium) leads to a dramatic increase in the transfection efficiency of nucleic acids (e.g., plasmids) formulated as SPLP or "stabilized nucleic acid (e.g., plasmid)-lipid particles." Typically, SPLP are less than about 150 nm in diameter (more preferably about 70 nm in diameter) and consist of a single plasmid encapsulated within a bilayer lipid vesicle.

As used herein, the term "endosomal membrane destabilizer" (EMD) refers to an agent(s) that is believed to facilitate the disruption or destabilization of the endosomal membrane thereby enhancing the release of their contents. Endosomes are typically distinct intracellular compartments isolated from the rest of the cell by a selectively permeable membrane. Suitable EMDs include, but are not limited to, monovalent metal ions such as $K^+$, $Na^+$, divalent metal ions such as $Mg^{2+}$, $Ca^{2+}$, $Mn^{2+}$, $Co^{2+}$, and combinations of th ions with cationic lipids. The most preferred EMD is $Ca^{2+}$ ion wherein approximately $10^6$ times higher transfection efficiency is observed for SPLPs containing $Ca^{2+}$ ions than SPLPs in the absence of $Ca^{2+}$ ions.

The present methods can be used in vitro or in vivo, and can be used to increase the transfection efficiency of any cell type, including mammalian cells. For example, for in vitro transfection, an endosomal membrane destabilizer (e.g., calcium) can be added to the transfection medium. For instance, any of a wide range of calcium concentrations can be used, ranging, for example, from 0.1 mM to 100 mM. Preferably, from about 1 mM to about 20 mM is used, most preferably from about 8 to about 10 mM. In one embodiment, the endosomal membrane destabilizer (e.g., calcium) is first added to the SPLP at a high concentration which will give rise to a desired final concentration following the dilution of the SPLP into the transfection medium. In other embodiments, the endosomal membrane destabilizer (e.g., calcium) is added to the SPLP at the time of transfection into the cells. The endosomal membrane destabilizer can be co-administered with the SPLP, it can be administered prior to the administration of the SPLP or it can be administered after the administration of the SPLP.

In vivo, any method can be used that will result in a local increase of the endosomal membrane destabilizer (e.g., calcium) concentration at the site of transfection. For example, particles can be formulated to incorporate the endosomal membrane destabilizer, particles can be soaked in a solution containing a high endosomal membrane destabilizer (e.g., calcium) concentration prior to administration, or the particles can be administered in a buffer or formulation containing a high endosomal membrane destabilizer (e.g., calcium) concentration. Such methods are especially useful for the local delivery of particles, e.g., intratumoral injection, where the co-administration of, e.g., calcium ions, can produce a locally high calcium concentration, thereby leading to enhanced transfection of the particles into cells at or near the site of delivery. Again, the endosomal membrane destabilizer can be co-administered with the SPLP, it can be administered prior to the administration of the SPLP or it can be administered after the administration of the SPLP.

In certain in vivo or in vitro embodiments, the SPLP are formulated to include on their surface chelating molecules for chelating the endosomal membrane destabilizer, e.g., lipids derivatized with a endosomal membrane destabilizer chelator, thereby allowing the generation of a locally high endosomal membrane destabilizer concentration even following systemic delivery of the particles. For instance, in certain in vivo or in vitro embodiments, particles are formulated to include calcium chelating molecules on the surface, e.g., lipids derivatized with a calcium chelator, thereby allowing the generation of a locally high calcium concentration even following systemic delivery of the particles.

Any SPLP particle can be used to practice the present invention. For example, SPLP comprising any of a broad range of concentrations of cationic and other lipids can be used. Similarly, the SPLP can comprise any of a wide variety of cationic and other lipids. The SPLP can be prepared with any plasmid, from any source and comprising any polynucleotide sequence, and can be prepared using any of a large number of methods.

The present invention also provides SPLP containing cationic PEG lipids, called SPLP-CPL. In a preferred embodiment, SPLP-$CPL_4$ is used, comprising a PEG lipid having four positive charges. SPLP and SPLP-CPL can be derivatized to include any of a number of functional groups, including, but not limited to, calcium chelators, cell or tissue-specific targeting molecules, labels, and others.

Suitable SPLP and SPLP-CPL for use in the present invention, and methods of making and using SPLP and SPLP-CPL, are taught, e.g., in U.S. application Ser. Nos. 60/130,151 and 09/553,639, as well as in PCT International Application PCT/CA00/00451, the teachings of each of which is incorporated herein in its entirety by reference.

II. Definitions

The term "lipid" refers to a group of organic compounds that include, but are not limited to, esters of fatty acids and are characterized by being insoluble in water, but soluble in many organic solvents. They are usually divided into at least three classes: (1) "simple lipids" which include fats and oils as well as waxes; (2) "compound lipids" which include phospholipids and glycolipids; (3) "derived lipids" such as steroids.

The term "vesicle-forming lipid" is intended to include any amphipathic lipid having a hydrophobic moiety and a polar head group, and which by itself can form spontaneously into bilayer vesicles in water, as exemplified by most phospholipids.

The term "vesicle-adopting lipid" is intended to include any amphipathic lipid which is stably incorporated into lipid bilayers in combination with other amphipathic lipids, with its hydrophobic moiety in contact with the interior, hydrophobic region of the bilayer membrane, and its polar head group moiety oriented toward the exterior, polar surface of the membrane. Vesicle-adopting lipids include lipids that on their own tend to adopt a nonlamellar phase, yet which are capable of assuming a bilayer structure in the presence of a bilayer-stabilizing component. A typical example is DOPE (dioleoylphosphatidylethanolamine). Bilayer stabilizing components include, but are not limited to, conjugated lipids that inhibit aggregation of the SPLPs, polyamide oligomers (e.g., ATTA-lipid derivatives), peptides, proteins, detergents, lipid-derivatives, PEG-lipid derivatives such as PEG coupled to phosphatidylethanolamines, and PEG conjugated to ceramides (see, U.S. application Ser. No. 08/485,608, now U.S. Pat. No. 5,885,613, which is incorporated herein by reference).

The term "amphipathic lipid" refers, in part, to any suitable material wherein the hydrophobic portion of the lipid material orients into a hydrophobic phase, while the hydrophilic portion orients toward the aqueous phase. Amphipathic lipids are usually the major component of a lipid vesicle. Hydrophilic characteristics derive from the presence of polar or charged groups such as carbohydrates, phosphate, carboxylic, sulfato, amino, sulfhydryl, nitro, hydroxy and other like groups. Hydrophobicity can be conferred by the inclusion of apolar groups that include, but are not limited to, long chain saturated and unsaturated aliphatic hydrocarbon groups and such groups substituted by one or more aromatic, cycloaliphatic or heterocyclic group(s). Examples of amphipathic compounds include, but are not limited to, phospholipids, aminolipids and sphingolipids. Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine or dilinoleoylphosphatidylcholine. Other compounds lacking in phosphorus, such as sphingolipid, glycosphingolipid families, diacylglycerols and β-acyloxyacids, are also within the group designated as amphipathic lipids. Additionally, the amphipathic lipid described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides and diacylglycerols.

The term "hydrophopic lipid" refers to compounds having apolar groups that include, but are not limited to, long chain saturated and unsaturated aliphatic hydrocarbon groups and such groups optionally substituted by one or more aromatic, cycloaliphatic or heterocyclic group(s). Suitable examples include, but are not limited to, diacylglycerol, dialkylglycerol, N-N-dialkylamino, 1,2-diacyloxy-3-aminopropane and 1,2-dialkyl-3-aminopropane.

The term "diacylglycerolyl" denotes 2-fatty acyl chains, $R^1$ and $R^2$ having independently between 2 and 30 carbons bonded to the 1- and 2-position of glycerol by ester linkages. The acyl groups can be saturated or have varying degrees of unsaturation.

The term "dialkylglycerolyl" denotes two $C_1$–$C_{30}$ alkyl chains bonded to the 1- and 2-position of glycerol by ether linkages.

The term "N-N-dialkylamino" denotes

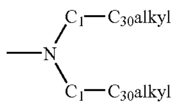

The term "1,2-diacyloxy-3-aminopropane" denotes 2-fatty acyl chains $C_1$–$C_{30}$ bonded to the 1- and 2-position of propane by an ester linkage. The acyl groups can be saturated or have varying degrees of unsaturation. The 3-position of the propane molecule has a —NH— group attached. 1,2-diacyloxy-3-aminopropanes have the following general formula:

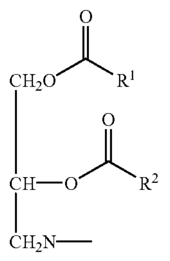

The term "1,2-dialkyl-3-aminopropane" denotes 2-alkyl chains ($C_1$–$C_{30}$) bonded to the 1- and 2-position of propane by an ether linkage. The 3-position of the propane molecule has a —NH— group attached. 1,2-dialkyl-3-aminopropanes have the following general formula:

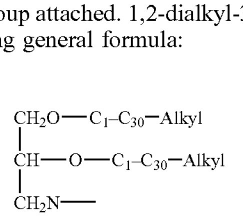

The term "noncationic lipid" refers to any neutral lipid as described above as well as anionic lipids. Examples of anionic lipids include, but are not limited to, phosphatidylglycerol, cardiolipin, diacylphosphatidylserine, diacylphosphatidic acid, N-dodecanoyl phosphatidylethanolamines, N-succinyl phosphatidylethanolamines, N-glutarylphosphatidylethanolamines, lysophosphatidylglycerols, and other anionic modifying groups joined to neutral lipids.

The term "cationic lipid" refers to any of a number of lipid species that carry a net positive charge at a selected pH, such as physiological pH. Such lipids include, but are not limited to, N,N-dioleyl-N,N-dimethylammonium chloride ("DODAC"); N-(2,3-dioleyloxy)propyl)-N,N,N-trimethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 3-(N-(N',N'-dimethylaminoethane)-carbamoyl)cholesterol ("DC-Chol") and N-(1,2-dimyristyloxyprop-3-yl)-N,N-dimethyl-N-hydroxyethyl ammonium bromide ("DMRIE"). Additionally, a number of commercial preparations of cationic lipids are available which can be used in the present invention. These include, for example, LIPOFECTIN® (commercially available cationic liposomes comprising DOTMA and 1,2-dioleoyl-sn-3-phosphoethanolamine ("DOPE"), from GIBCO/BRL, Grand Island, N.Y. USA); LIPOFECTAMINE® (commercially available cationic liposomes comprising N-(1-(2,3-dioleyloxy)propyl)-N-(2-(sperminecarboxamido)ethyl)-N,N-dimethylammonium trifluoroacetate ("DOSPA") and("DOPE"), from GIBCO/BRL); and TRANSFECTAM® (commercially available cationic lipids comprising dioctadecylamidoglycyl carboxyspernine ("DOGS") in ethanol from Promega Corp., Madison, Wis., USA). The following lipids are cationic and have a positive charge at below physiological pH: DODAP, DODMA, DMDMA and the like.

The term "fusogenic" refers to the ability of a liposome, an SPLP or other drug delivery system to fuse with membranes of a cell. The membranes can be either the plasma membrane or membranes surrounding organelles, e.g., endosome, nucleus, etc. Fusogenesis is the fusion of a liposome to such a membrane.

The term "dendrimer" includes reference to branched polymers that possess multiple generations. In dendrimers, each generation creates multiple branch points.

The term "ligand" includes any molecule, compound or device with a reactive functional group and includes lipids, amphipathic lipids, carrier compounds, chelating moities, bioaffinity compounds, biomaterials, biopolymers, biomedical devices, analytically detectable compounds, therapeutically active compounds, enzymes, peptides, proteins, antibodies, immune stimulators, radiolabels, fluorogens, biotin, drugs, haptens, DNA, RNA, polysaccharides, liposomes, virosomes, micelles, immunoglobulins, functional groups, targeting agents, or toxins. The foregoing list is illustrative and not intended to be exhaustive.

The term "ATTA" or "polyamide" refers to, but is not limited to, compounds disclosed in U.S. patent application Ser. No. 09/218,988, filed Dec. 22, 1998. These compounds include a compound having the formula

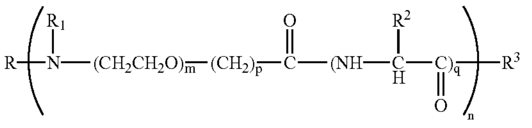

wherein: R is a member selected from the group consisting of hydrogen, alkyl and acyl; $R^1$ is a member selected from the group consisting of hydrogen and alkyl; or optionally, R and $R^1$ and the nitrogen to which they are bound form an azido moiety; $R^2$ is a member of the group selected from hydrogen, optionally substituted alkyl, optionally substituted aryl and a side chain of an amino acid; $R^3$ is a member selected from the group consisting of hydrogen, halogen, hydroxy, alkoxy, mercapto, hydrazino, amino and $NR^4R^5$, wherein $R^4$ and $R^5$ are independently hydrogen or alkyl; n is 4 to 80; m is 2 to 6; p is 1 to 4; and q is 0 or 1. It will be apparent to those of skill in the art that other polyamides can be used in the compounds of the present invention.

As used herein, the term "alkyl" denotes branched or unbranched hydrocarbon chains, such as, methyl, ethyl, n-propyl, iso-propyl, n-butyl, sec-butyl, iso-butyl, tertbutyl, octa-decyl and 2-methylpentyl. These groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoromethyl, 3-hydroxyhexyl, 2-carboxypropyl, 2-fluoroethyl, carboxymethyl, cyanobutyl and the like.

The term "alkylene" refers to a divalent alkyl as defined above, such as methylene ($—CH_2—$), propylene ($—CH_2CH_2CH_2—$), chloroethylene ($—CHClCH_2—$), 2-thiobutene $CH_2CH(SH)CH_2CH_2—$), 1-bromo-3-hydroxyl-4-methylpentene ($—CHBrCH_2CH(OH)CH(CH_3)CH_2—$), and the like.

The term "alkenyl" denotes branched or unbranched hydrocarbon chains containing one or more carbon-carbon double bonds.

The term "alkynyl" refers to branched or unbranched hydrocarbon chains containing one or more carbon-carbon triple bonds.

The term "aryl" denotes a chain of carbon atoms which form at least one aromatic ring having preferably between about 6–14 carbon atoms, such as phenyl, naphthyl, indenyl, and the like, and which may be substituted with one or more functional groups which are attached commonly to such chains, such as hydroxyl, bromo, fluoro, chloro, iodo, mercapto or thio, cyano, cyanoamido, alkylthio, heterocycle, aryl, heteroaryl, carboxyl, carbalkoyl, alkyl, alkenyl, nitro, amino, alkoxyl, amido, and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, amidophenyl, thiazolylphenyl, oxazolylphenyl, imidazolylphenyl, imidazolylmethylphenyl, and the like.

The term "acyl" denotes the —C(O)R group, wherein R is alkyl or aryl as defined above, such as formyl, acetyl, propionyl, or butyryl.

The term "alkoxy" denotes —OR—, wherein R is alkyl.

The term "amido" denotes an amide linkage: —C(O)NR— (wherein R is hydrogen or alkyl).

The term "amino" denotes an amine linkage: —NR—, wherein R is hydrogen or alkyl or a terminal $NH_2$.

The term "carboxyl" denotes the group —C(O)O—, and the term "carbonyl" denotes the group —C(O)—.

The term "carbonate" indicates the group —OC(O)O—.

The term "carbamate" denotes the group —NHC(O)O—, and the term "urea" denotes the group —NHC(O)NH—.

The term "phosphoro" denotes the group —OP(O)(OH)O—.

The term "basic amino acid" refers to naturally-occurring amino acids as well as synthetic amino acids and/or or amino acid mimetics having a net positive charge at a selected pH, such as physiological pH. This group includes, but is not limited to, lysine, arginine, asparagine, glutamine, histidine and the like.

The term "phosphorylethanolamino" denotes the group $—OP(O)(OH)OCH_2CH_2NH—$.

The term "phosphorylethanolamido" denotes the group $—OP(O)(OH)OCH_2CH_2NHC(O)—$.

The term "phospho" denotes a pentavalent phosphorous moiety —P(O)(OH)O—.

The term "phosphoethanolamino" denotes the group $—P(O)(OH)OCH_2CH_2NH—$.

The term "phosphoethanolamido" denotes the group $—P(O)(OH)OCH_2CH_2NHC(O)—$.

The term "ethylene oxide unit" denotes the group $—OCH_2CH_2—$.

The term "CPL" refers to a cationic-polymer-lipid, e.g., cationic-PEG-lipid. Preferred CPLs are compounds of Formulae I and II. Such CPLs are disclosed in U.S. patent application Ser. No. 09/553,639, which was filed Apr. 20, 2000, and PCT Patent Application No. CA 00/00451, which was filed Apr. 20, 2000 and which published as WO 00/62813 on Oct. 26, 2000.

The term "d-DSPE-CPL-M" is encompassed by the term "CPL1" which refers to a DSPE-CPL having one positive charge. The "d-" in d-DSPE-CPL-M indicates that the CPL contains a fluorescent dansyl group. It will be apparent to those of skill in the art that a CPL can be synthesized without the dansyl moiety, and thus the term "DSPE-CPL-M" is encompassed by in the term "CPL1" as defined above.

The term "d-DSPE-CPL-D" is encompassed by the term "CPL2" which refers to DSPE-CPL having two positive charges.

The term "d-DSPE-CPL-T1" is encompassed by the term "CPL3" which refers to DSPE-CPL having three positive charges.

The term "d-DSPE-CPL-Q1" is encompassed by the term "CPL4a" which refers to DSPE-CPL having four positive charges.

The term "d-DSPE-CPL-Q5," or, alternatively, DSPE-PEGQuad5, or, alternatively, DSPE-CPL-4, are all encompassed by the term "CPL4 (or CPL4b)" which refer to a DSPE-CPL having four positive charges. By modifying the headgroup region, CPLs were synthesized which contained 1 (mono, or M), 2 (di, or D), 3 (tri, or T), and 4 (quad, or Q) positive charges. Various Quad CPLs were synthesized, hence these are numbered QI through Q5.

The abbreviations "HBS" refers to Hepes-buffered saline, "Rho-PE" refers to rhodamine-phosphatidylethanolamine, and "LUVs" refers to "large unilamellar vesicles."

II. Nucleic Acid-Lipid Particles (SPLPs) and Properties Thereof

The nulceic acid-lipid particles or, alternatively, SPLPs typically comprise cationic lipid and nucleic acids. Such SPLPs also preferably comprise noncationic lipid and a bilayer stabilizing component or, more preferably, a conjugated lipid that inhibits aggregation of the SPLPs. The SPLPs of the present invention have a mean diameter of less than about 150 nm and are substantially nontoxic. In addition, the nucleic acids when present in the SPLPs of the present invention are resistant to aqueous solution to degradation with a nuclease. Such SPLPs are disclosed in great detail in U.S. Pat. No. 5,976,567 and PCT Patent Publication No. WO 96/40964, the teachings of both of which are incoporated herein by reference.

A. SPLP Components

Various suitable cationic lipids may be used in the present invention, either alone or in combination with one or more other cationic lipid species or neutral lipid species.

Cationic lipids which are useful in the present invention can be any of a number of lipid species which carry a net positive charge at physiological pH, for example: DODAC, DOTMA, DDAB, DOTAP, DOSPA, DOGS, DC-Chol and DMRIE, or combinations thereof. A number of these lipids and related analogs, which are also useful in the present invention, have been described in co-pending U.S. Ser. No. 08/316,399; U.S. Pat. Nos. 5,208,036, 5,264,618, 5,279,833 and 5,283,185, the disclosures of which are incorporated herein by reference. Additionally, a number of commercial preparations of cationic lipids are available and can be used in the present invention. These include, for example, LIPOFECTIN® (commercially available cationic liposomes comprising DOTMA and DOPE, from GIBCO/BRL, Grand Island, N.Y. USA); LIPOFECTAMINE® (commercially available cationic liposomes comprising DOSPA and DOPE, from GIBCO/BRL); and TRANSFECTAMT® (commercially available cationic liposomes comprising DOGS from Promega Corp., Madison, Wis., USA).

The noncationic lipids used in the present invention can be any of a variety of neutral uncharged, zwitterionic or anionic lipids capable of producing a stable complex. They are preferably neutral, although they can alternatively be positively or negatively charged. Examples of noncationic lipids useful in the present invention include: phospholipid-related materials, such as lecithin, phosphatidylethanolamine, lysolecithin, lysophosphatidylethanolamine, phosphatidylserine, phosphatidylinositol, sphingomyelin, cephalin, cardiolipin, phosphatidic acid, cerebrosides, dicetylphosphate, dioleoylphosphatidylcholine (DOPC), dipalmitoyl-phosphatidylcholine (DPPC), dioleoylphosphatidylglycerol (DOPG), dipalmitoylphosphatidylglycerol (DPPG), dioleoylphosphatidylethanolamine (DOPE), palmitoyloleoy-lphosphatidylcholine (POPC), palmitoyloleoyl- phosphatidylethanolamine (POPE) and dioleoylphosphatidylethanolamine 4-(N-maleimidomethyl)-cyclohexane-1-carboxylate (DOPE-mal). Additional nonphosphorous containing lipids are, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide and the like, diacylphosphatidylcholine, diacylphosphatidylethanolamine, ceramide, sphingomyelin, cephalin, and cerebrosides. Other lipids such as lysophosphatidylcholine and lysophosphatidylethanolamine may be present. Noncationic lipids also include polyethylene glycol-based polymers such as PEG 2000, PEG 5000 and polyethylene glycol conjugated to phospholipids or to ceramides (referred to as PEG-Cer), as described in co-pending U.S. Ser. No. 08/316,429, incorporated herein by reference.

In preferred embodiments, the noncationic lipids are diacylphosphatidylcholine (e.g., dioleoylphosphatidylcholine, dipalmitoylphosphatidylcholine and dilinoleoylphosphatidylcholine), diacylphosphatidylethanolamine (e.g., dioleoylphosphatidylethanolamine and palmitoyloleoylphosphatidylethanolamine), ceramide or sphingomyelin. The acyl groups in these lipids are preferably acyl groups derived from fatty acids having $C_{10}$–$C_{24}$ carbon chains. More preferably the acyl groups are lauroyl, myristoyl, palmitoyl, stearoyl or olcoyl. In particularly preferred embodiments, the noncationic lipid will be 1,2-sn-dioleoylphosphatidylethanolamine, or egg sphingomyelin (ESM).

In one embodiment, the SPLP further comprises a bilayer stabilizing component (BSC). Suitable BSCs include, but are not limited to, polyamide oligomers, peptides, proteins, detergents, lipid-derivatives, PEG-lipids such as PEG coupled to phosphatidylethanolamine, and PEG conjugated to ceramides (see, U.S. Pat. No. 5,885,613, which is incorporated herein by reference). Preferably, the bilayer stabilizing component is a PEG-lipid, or an ATTA-lipid. In a presently preferred embodiment, the BSC is a conjugated lipid that inhibits aggregation of the SPLPs. Suitable conjugated lipids include, but are not limited to PEG-lipid conjugates, ATTA-lipid conjugates, cationic-polymer-lipid conjugates (CPLs) or mixtures thereof. In a presently preferred embodiment, the SPLPs comprise either a PEG-lipid conjugate or an ATTA-lipid conjugate together with a CPL.

The CPLs used in the present invention have the following architectural features: (1) a lipid anchor, such as a hydrophobic lipid, for incorporating the CPLs into the lipid bilayer; (2) a hydrophilic spacer, such as a polyethylene glycol, for linking the lipid anchor to a cationic head group; and (3) a polycationic moiety, such as a naturally occurring amino acid, to produce a protonizable cationic head group. As such, the present invention provides a compound of Formula I:

A-W-Y I wherein A, W and Y are as follows.

With reference to Formula I, "A" is a lipid moiety such as an amphipathic lipid, a neutral lipid or a hydrophobic lipid that acts as a lipid anchor. Suitable lipid examples include vesicle-forming lipids or vesicle adopting lipids and include, but are not limited to, diacylglycerolyls, dialkylglycerolyls, N-N-dialkylaminos, 1,2-diacyloxy-3-aminopropanes and 1,2-dialkyl-3-aminopropanes.

"W" is a polymer or an oligomer, such as a hydrophilic polymer or oligomer. Preferably, the hydrophilic polymer is a biocompatable polymer that is nonimmunogenic or possesses low inherent immunogenicity. Alternatively, the hydrophilic polymer can be weakly antigenic if used with appropriate adjuvants. Suitable nonimmunogenic polymers include, but are not limited to, PEG, polyamides, polylactic acid, polyglycolic acid, polylactic acid/polyglycolic acid copolymers and combinations thereof. In a preferred embodiment, the polymer has a molecular weight of about 250 to about 7000 daltons.

"Y" is a polycationic moiety. The term polycationic moiety refers to a compound, derivative, or functional group having a positive charge, preferably at least 2 positive charges at a selected pH, preferably physiological pH.

Suitable polycationic moieties include basic amino acids and their derivatives such as arginine, asparagine, glutamine, lysine and histidine; spermine; spermidine; cationic dendrimers; polyamines; polyamine sugars; and amino polysaccharides. The polycationic moieties can be linear, such as linear tetralysine, branched or dendrimeric in structure. Polycationic moieties have between about 2 to about 15 positive charges, preferably between about 2 to about 12 positive charges, and more preferably between about 2 to about 8 positive charges at selected pH values. The selection of which polycationic moiety to employ may be determined by the type of liposome application which is desired.

The charges on the polycationic moieties can be either distributed around the entire liposome moiety, or alternatively, they can be a discrete concentration of charge density in one particular area of the liposome moiety e.g., a charge spike. If the charge density is distributed on the liposome, the charge density can be equally distributed or unequally distributed. All variations of charge distribution of the polycationic moiety are encompassed by the present invention.

The lipid "A," and the nonimmunogenic polymer "W," can be attached by various methods and preferably, by covalent attachment. Methods known to those of skill in the art can be used for the covalent attachment of "A" and "W." Suitable linkages include, but are not limited to, amide, amine, carboxyl, carbonate, carbamate, ester and hydrazone linkages. It will be apparent to those skilled in the art that "A" and "W" must have complementary functional groups to effectuate the linkage. The reaction of these two groups, one on the lipid and the other on the polymer, will provide the desired linkage. For example, when the lipid is a diacylglycerol and the terminal hydroxyl is activated, for instance with NHS and DCC, to form an active ester, and is then reacted with a polymer which contains an amino group, such as with a polyamide (see, U.S. patent application Ser. No. 09/218,988, filed Dec. 22, 1998), an amide bond will form between the two groups.

In certain embodiments, "W" is bound, preferably covalently bound, to "Y". As with "A" and "W", a covalent attachment of "W" to "Y" can be generated by complementary reactivity of functional groups, one on the polymer and the other on the polycationic moiety. For example, an amine functional group on "W" can be reacted with an activated carboxyl group, such as an acyl chloride or NHS ester, to form an amide. By suitable choice of reactive groups, the desired coupling can be obtained. Other activated carboxyl groups include, but are not limited to, a carboxylic acid, a carboxylate ester, a carboxylic acid halide and other activated forms of carboxylic acids, such as a reactive anhydride. Reactive acid halides include for example, acid chlorides, acid bromides, and acid fluorides.

In certain instances, the polycationic moiety can have a ligand attached, such as a targeting ligand or a chelating moiety for complexing calcium. Preferably, alter the ligand is attached, the cationic moiety maintains a positive charge. In certain instances, the ligand that is attached has a positive charge. Suitable ligands include, but are not limited to, a compound or device with a reactive functional group and include lipids, amphipathic lipids, carrier compounds, bioaffinity compounds, biomaterials, biopolymers, biomedical devices, analytically detectable compounds, therapeutically active compounds, enzymes, peptides, proteins, antibodies, immune stimulators, radiolabels, fluorogens, biotin, drugs, haptens, DNA, RNA, polysaccharides, liposomes, virosomes, micelles, immunoglobulins, finctional groups, other targeting moieties, or toxins. Suitable chelating moieties for chelating or complexing the endosomal membrane destabilizer are described below.

In certain preferred embodiments, other moieties are incorporated into the compounds of Formula I to form the compounds of Formula II:

$$A\text{—}(X\text{—}(CH_2\text{—}CH_2\text{—}O)_n\text{—}Z)\text{—}Y \qquad \text{II}$$

In Formula II, "A" is a lipid moiety such as, an amphipathic lipid, a neutral lipid or a hydrophobic lipid moiety. Suitable lipid examples include, but are not limited to, diacylglycerolyl, dialkylglycerolyl, N-N-dialkylamino, 1,2-diacyloxy-3-aminopropane and 1,2-dialkyl-3-aminopropane.

In Formula II, "X" is a single bond or a functional group that covalently attaches the lipid to at least one ethylene oxide unit. Suitable functional groups include, but are not limited to, phosphatidylethanolamino, phosphatidylethanolamido, phosphoro, phospho, phosphoethanolamino, phosphoethanolamido, carbonyl, carbamate, carboxyl, carbonate, amido, thioamido, oxygen, NR wherein R is a hydrogen or alkyl group and sulfur. In certain instances, the lipid "A" is directly attached to the ethylene oxide unit by a single bond. The number of ethylene oxide units can range from about 1 to about 160 and preferably from about 6 to about 50.

In Formula II, "Z" is a single bound or a functional group that covalently attaches the ethylene oxide unit to the polycationic moiety. Suitable functional groups include, but are not limited to, phospho, phosphoethanolamino, phosphoethanolamido, carbonyl, carbamate, carboxyl, amido, thioamido, NR wherein R is a member selected from the group consisting of hydrogen atom or alkyl group. In certain embodiments, the terminal ethylene oxide unit is directly attached to the polycationic moiety.

In Formula II, "Y" is a polycationic moiety as described above in connection with Formula I. In Formula II, the index "n" is an integer ranging in value from about 6 to about 160.

Figure 21A:
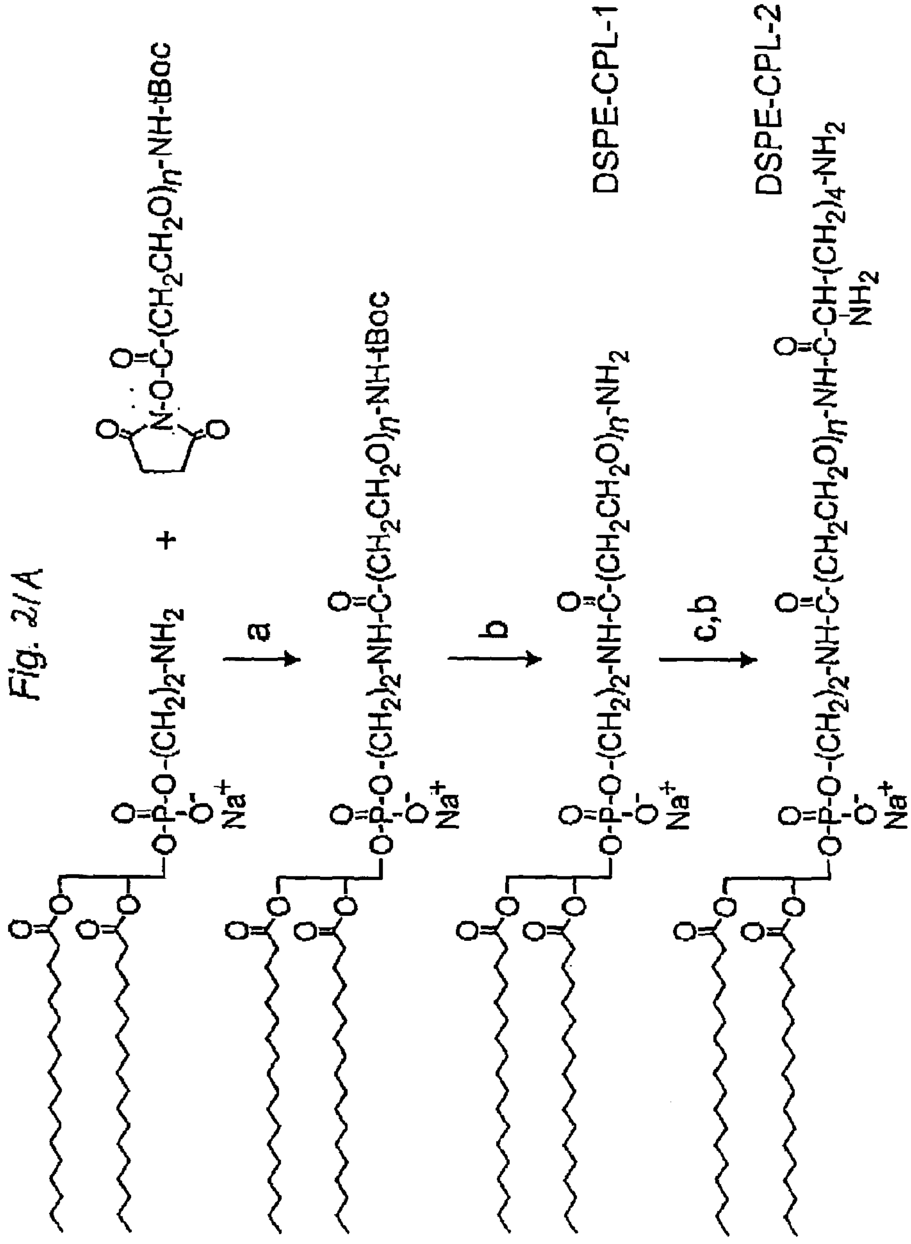
FIG. 21. A synthetic scheme for the preparation of cationic-PEG-lipid conjugates having varying amount of charged head groups (FIG. 21A ) $Et_3N/CHCl_3$.
(FIG. 21B.) $TFA/CHCl_3$; c. $Et_3N/CHCl_3$ Nα, Nϵ-di-t-Boc-L-Lysine N-hydroxysuccinide ester.
Figure 21B:

In an illustrative embodiment, compounds of Formula II can be synthesized using a generalized procedure as outlined in FIG. 21. FIG. 21 illustrates one particular embodiment of the present invention and thus, is merely an example that should not limit the scope of the claims herein. Clearly, one of ordinary skill in the art will recognize many other variations, alternatives, and modifications that can be made to the reaction scheme illustrated in FIG. 21. With reference to FIG. 21, a solution of a lipid, such as DSPE, and a base, such as triethylamine in a chloroform solution is added to (t-Boc-NH-$PEG_{3400}$-$CO_2$NHS), and the solution is stirred at ambient temperature. The solution is then concentrated under a nitrogen stream to dryness. The residue is then purified by repeated precipitation of the chloroform mixture solution with diethyl ether until disappearance of the lipid using chromatography. The purified CPL conjugate is dissolved in a solvent, followed by addition of TFA, and the solution is stirred at room temperature. The solution can again be concentrated under a nitrogen stream. The residue is then purified by repeated precipitation of the mixture with diethyl ether to offer a lipid-PEG-$NH_2$, such as a DSPE-PEG-$NH_2$ or, alternatively, DSPE-CPL-1 with one protonizable cationic head group. The ratio of the phosphoryl-lipid anchor and the distal primary amine can then be measured by phosphate and flourescamine assays as described herein.

In this illustrative embodiment, the number of protonizable amino groups can be increased to create a polycationic moiety. By incrementally adding stoichiometric amounts of, for example, a Nα,Nε-di-t-Boc-L-Lysine N-hydroxysuccinide ester, the polycationic moiety can be increase from about 2 to about 16 positive charges. As describe previously, the positive charges can be incorporated using any number of suitable polycationic moieties such as lysine, arginine, asparagine, glutamine, histidine, polyamines and derivatives or combinations thereof. Using the synthesis methods of the present invention, the number of cationic groups, such as amino groups, can be readily controlled during the CPL synthesis.

In addition, as explained above, the endosomal membrane destabilizer can be incorporated into the nucleic acid-lipid particle. In such embodiments. the endosomal membrane destabilizer can be loaded into the nucleic-acid lipid particle using any of a number of different loading techniques (see, Examples I and II). Exemplar loading methods are disclosed, for example, in U.S. Pat. No. 4,885,172, U.S. Pat. No. 5,059,421, and U.S. Pat. No. 5,171,578, the teachings of which are incorporated herein by reference. In addition, a particularly preferred ionophore-mediated loading process is disclosed and claimed in U.S. Pat. No. 5,837,282, the teachings of which are incorporated herein by reference.

Moreover, as explained above, a chelating moiety suitable for chelating the endosomal membrane destabilizer can be attached, linked or coupled to any of the lipid components of the SPLP, such as the CPL. In a presently preferred embodiment, the chelating moiety is a metal chelator. Metal chelators, such as ethylenediaminetetraacetic acid (EDTA), diethylenetriaminepentaacetic acid (DTPA), ethylenebis (oxyethylenenitrilo)-tetraacetic acid (EGTA), 1,4,7,10-tetraazacyclododecane-N,N',N",N'"-tetraacetic acid, trans-1,2-cyclohexylenediamine-N,N,N',N'-tetraacetic acid,$N^6$-carboxymethyl-$N^3$,$N^9$-[2,3-dihydroxy-N-methylpropylcarbamoylmethyl]-3,6,9-triazaundecanedioic acid, $N^6$-carboxymethyl-$N^3$,$N^9$-bis(methylcarbamoylmethyl)-3,6,9-triazaundecanedioic acid, $N^3$,$N^6$-bis (carboxymethyl)-$N^9$-3-oxapentamethylene-carbamoylmethyl-3,6,9-triazaundecanedioic acid or $N^3$,$N^6$-bis(carboxymethyl)-$N^9$[3,3-bis (dihydroxyphosphoryl)-3-hydroxypropyl-carbarnoylmethyl]-3,6,9-triazaundecanedioic acid, metal ion transporters, metal ion transport proteins, metal sequesters, metal chelate ligands, and the like can be used to chelate the endosomal membrane destabilizer. In addition, the metal chelators disclosed in U.S. Pat. No. 5,876,695, which is incorporated herein by reference, can also be used. Other chelators suitable for use in the compositions and methods of the present invention witll be known to those of skill in the art.

2. Nucleic Acid Component

While the invention is described in the examples with reference to the use of plasmids, one of skill in the art will understand that the methods described herein are equally applicable to other larger nucleic acids or oligonucleotides. As such, suitable nucleic acids include, but are not limited to, plasmids, antisense oligonucleotides, ribozymes as well as other poly- and oligo-nucleotides.

The nucleic acids which are useful in the present invention (including both the complexes and particles) are typically nucleotide polymers having from 10 to 100,000 nucleotide residues. Typically, the nucleic acids are to be administered to a subject for the purpose of repairing or enhancing the expression of a cellular protein. Additionally, the nucleic acid can carry a label (e.g., radioactive label, fluorescent label or colorimetric label) for the purpose of providing clinical diagnosis relating to the presence or absence of complementary nucleic acids. Accordingly, the nucleic acids, or nucleotide polymers, can be polymers of nucleic acids including genomic DNA, cDNA, MRNA or oligonucleotides containing nucleic acid analogs, for example, the antisense derivatives described in a review by Stein, et al., *Science* 261:1004–1011 (1993) and in U.S. Pat. Nos. 5,264,423 and 5,276,019, the disclosures of which are incorporated herein by reference. Still further, the nucleic acids may encode transcriptional and translational regulatory sequences including promoter sequences and enhancer sequences.

The nucleotide polymers can be single-stranded DNA or RNA, or double-stranded DNA or DNA-RNA hybrids. Examples of double-stranded DNA include structural genes, genes including control and termination regions, and self-replicating systems such as plasmid DNA.

Single-stranded nucleic acids include antisense oligonucleotides (complementary to DNA and RNA), ribozymes and triplex-forming oligonucleotides. In order to increase stability, some single-stranded nucleic acids will preferably have some or all of the nucleotide linkages substituted with stable, nonphosphodiester linkages, including, for example, phosphorothioate, phosphorodithioate, phosphoroselenate, or O-alkyl phosphotriester linkages.

The nucleic acids used in the present invention will also include those nucleic acids in which modifications have been made in one or more sugar moieties and/or in one or more of the pyrimidine or purine bases. Examples of sugar modifications include replacement of one or more hydroxyl groups with halogens, alkyl groups, amines, azido groups or functionalized as ethers or esters. Additionally, the entire sugar may be replaced with sterically and electronically similar structures, including aza-sugars and carbocyclic sugar analogs. Modifications in the purine or pyrimidine base moiety include, for example, alkylated purines and pyrimidines, acylated purines or pyrimidines, or other heterocyclic substitutes known to those of skill in the art.

Multiple genetic sequences can be also be used in the present methods. Thus, the sequences for different proteins may be located on one strand or plasmid. Nonencoding sequences may be also be present, to the extent that they are necessary to achieve appropriate expression.

The nucleic acids used in the present method can be isolated from natural sources, obtained from such sources as ATCC or GenBank libraries or prepared by synthetic methods. Synthetic nucleic acids can be prepared by a variety of solution or solid phase methods. Generally, solid phase synthesis is preferred. Detailed descriptions of the procedures for solid phase synthesis of nucleic acids by phosphite-triester, phosphotriester, and H-phosphonate chemistries are widely available. See, for example, Itakura, U.S. Pat. No. 4,401,796; Caruthers, et al., U.S. Pat. Nos. 4,458,066 and 4,500,707; Beaucage, et al., *Tetrahedron Lett.*, 22:1859–1862 (1981); Matteucci, et al., *J. Am. Chem. Soc.*, 103:3185–3191 (1981); Caruthers, et al., *Genetic Engineering*, 4:1–17 (1982); Jones, chapter 2, Atkinson, et al., chapter 3, and Sproat, et al., chapter 4, in *Oligonucleotide Synthesis: A Practical Approach*, Gait (ed.), IRL Press, Washington D.C. (1984); Froehler, et al., *Tetrahedron Lett.*, 27:469–472 (1986); Froehler, et al., *Nucleic Acids Res.*, 14:5399–5407 (1986); Sinha, et al. *Tetrahedron Lett.*, 24:5843–5846 (1983); and Sinha, et al., *Nucl. Acids Res.*, 12:4539–4557 (1984) which are incorporated herein by reference.

a. Vectors for Introduction and Expression of Genes in Cells

An important aspect of this invention is the use of the lipid-nucleic acid particles provided herein to introduce selected genes into cells in vitro and in vivo, followed by expression of the selected gene in the host cell. Thus, the nucleic acids in the particles specificlly encompass vectors that are capable of being expressed in a host cell. Promoter, enhancer, stress or chemically-regulated promoters, antibiotic-sensitive or nutrient-sensitive regions, as well as therapeutic protein encoding sequences, may be included as required.

In brief summary, the expression of natural or synthetic nucleic acids is typically achieved by operably linking a nucleic acid of interest to a promoter (which is either constitutive or inducible), incorporating the construct into an expression vector, and introducing the vector into a suitable host cell. Typical vectors contain transcription and translation terminators, transcription and translation initiation sequences, and promoters useful for regulation of the expression of the particular nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman and Smith (1979), *Gene,* 8: 81–97; Roberts et al. (1987), *Nature,* 328:731–734; Berger and Kimmel, *Guide to Molecular Cloning Techniques, Methods in Enzymology*, volume 152, Academic Press, Inc., San Diego, Calif. (Berger); Sambrook et al. (1989), *MOLECULAR CLONING—A LABORATORY MANUAL* (2nd ed.) Vol. 1–3, Cold Spring Harbor Laboratory, Cold Spring Harbor Press, N.Y., (Sambrook); and F. M. Ausubel et al., *CURRENT PROTOCOLS IN MOLECULAR BIOLOGY*, eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosystems (Foster City, Calif.), as well as many other commercial sources known to one of skill.

Vectors to which foreign nucleic acids are operably linked may be used to introduce these nucleic acids into host cells and mediate their replication and/or expression. "Cloning vectors" are useful for replicating and amplifying the foreign nucleic acids and obtaining clones of specific foreign nucleic acid-containing vectors. "Expression vectors" mediate the expression of the foreign nucleic acid. Some vectors are both cloning and expression vectors.

In general, the particular vector used to transport a foreign gene into the cell is not particularly critical. Any of the conventional vectors used for expression in the chosen host cell may be used.

An expression vector typically comprises a eukaryotic transcription unit or "expression cassette" that contains all the elements required for the expression of exogenous genes in eukaryotic cells. A typical expression cassette contains a promoter operably linked to the DNA sequence encoding a desired protein and signals required for efficient polyadenylation of the transcript.

Eukaryotic promoters typically contain two types of recognition sequences, the TATA box and upstream promoter elements. The TATA box, located 25–30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus, the long term repeat from various retroviruses such as murine leukemia virus, murine or Rous sarcoma virus and HIV. See, *Enhancers and Eukaryotic Expression*, Cold Spring Harbor Press, Cold Spring Harbor, N.Y. 1983, which is incorporated herein by reference.

In addition to a promoter sequence, the expression cassette should also contain a transcription termination region downstream of the structural gene to provide for efficient termination. The termination region may be obtained from the same source as the promoter sequence or may be obtained from a different source.

If the mRNA encoded by the selected structural gene is to be efficiently translated, polyadenylation sequences are also commonly added to the vector construct. Two distinct sequence elements are required for accurate and efficient polyadenylation: GU or U rich sequences located downstream from the polyadenylation site and a highly conserved sequence of six nucleotides, AAUAAA, located 11–30 nucleotides upstream. Termination and polyadenylation signals that are suitable for the present invention include those derived from SV40, or a partial genomic copy of a gene already resident on the expression vector.

In addition to the elements already described, the expression vector of the present invention may typically contain other specialized elements intended to increase the level of expression of cloned nucleic acids or to facilitate the identification of cells that carry the transduced DNA. For instance, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The expression vectors of the present invention will typically contain both prokaryotic sequences that facilitate the cloning of the vector in bacteria as well as one or more eukaryotic transcription units that are expressed only in eukaryotic cells, such as mammalian cells. The prokaryotic sequences are preferably chosen such that they do not interfere with the replication of the DNA in eukaryotic cells.

Selected genes are normally be expressed when the DNA sequence is functionally inserted into a vector. "Functionally inserted" means that it is inserted in proper reading frame and orientation and operably linked to proper regulatory elements. Typically, a gene will be inserted downstream from a promoter and will be followed by a stop codon, although production as a hybrid protein followed by cleavage may be used, if desired.

Expression vectors containing regulatory elements from eukaryotic viruses such as retroviruses are typically used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/$A^+$, pMTO10/$A^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

While a variety of vectors may be used, it should be noted that viral vectors such as retroviral vectors are useful for modifying eukaryotic cells because of the high efficiency with which the retroviral vectors transfect target cells and integrate into the target cell genome. Additionally, the retroviruses harboring the retroviral vector are capable of infecting cells from a wide variety of tissues.

In addition to the retroviral vectors mentioned above, cells may be lipofected with adeno-associated viral vectors. See, e.g., *Methods in Enzymology*, Vol. 185, Academic Press, Inc., San Diego, CA (D. V. Goeddel, ed.) (1990) or M. Krieger (1990), *Gene Transfer and Expression—A Laboratory Manual*, Stockton Press, New York, N.Y., and the references cited therein. Adeno associated viruses (AAVs) require helper viruses such as adenovirus or herpes virus to achieve productive infection. In the absence of helper virus functions, AAV integrates (site-specifically) into a host cell's genome, but the integrated AAV genome has no pathogenic effect. The integration step allows the AAV genome to remain genetically intact until the host is exposed to the appropriate environmental conditions (e.g., a lytic helper virus), whereupon it re-enters the lytic life-cycle. Samulski (1993), *Current Opinion in Genetic and Development,* 3:74–80, and the references cited therein provides an overview of the AAV life cycle. See also West et al. (1987), *Virology,* 160: 38–47; Carter et al. (1989), U.S. Pat. No. 4,797,368; Carter et al. (1993), WO 93/24641; Kotin (1994), *Human Gene Therapy,* 5:793–801; Muzyczka (1994), *J. Clin. Invest.,* 94: 1351 and Samulski, supra, for an overview of AAV vectors.

Plasmids designed for producing recombinant vaccinia, such as pGS62, (Langford, C. L. et al. (1986), *Mol. Cell. Biol.,* 6:3191–3199) may also be used. This plasmid consists of a cloning site for insertion of foreign nucleic acids, the P7.5 promoter of vaccinia to direct synthesis of the inserted nucleic acid, and the vaccinia TK gene flanking both ends of the foreign nucleic acid.

Whatever the vector is used, generally the vector is genetically engineered to contain, in expressible form, a gene of interest that encodes a gene product of interest. Suitable classes of gene products include, but are not limited to, cytotoxic/suicide genes, immunomodulators, cell receptor ligands, tumor suppressors, and anti-angiogenic genes. The particular gene selected will depend on the intended purpose or treatment. Examples of such genes of interest are described below and throughout the specification. Cytotoxic/suicide genes are those genes that are capable of killing cells, causing apoptosis, or arresting cells in the cell cycle. Such genes include, but are not limited to, genes for immunotoxins, thymidine kinase, a cytochrome P450 2B1, a deoxycytidine kinase, or a cytosine deaminase. Agents such as acyclovir and ganciclovir (for thymidine kinase), cyclophosphoamide (for cytochrome P450 2B1), 5-fluorocytosine (for cytosine deaminase), are typically administered systemically in conjunction (e.g., simulatenously or nonsimulatenously) with the lipid-nucleic compositions of the present invention to achieve the desired cytotoxic or cytostatic effect. Immunomodulator genes are genes that modulate one or more immune responses. Examples of immunomodulator genes include cytokines such as growth factors (e.g., TGF-α., TGF-β, EGF, FGF, IGF, NGF, PDGF, CGF, GM-CSF, SCF, etc.), interleukins (e.g., IL-2, IL-12, IL-15, IL-20, etc.), interferons (e.g., IFN-σ, IFN-β, IFN-γ, etc.) and TNF. Cell receptor ligands include ligands that are able to bind to cell surface receptors (e.g., insulin receptor, EPO receptor, G-protein coupled receptors, receptors with tyrosine kinase activity, cytokine receptors, growth factor receptors, etc.), to modulate (e.g,. inhibit, activate, etc.) the physiological pathway that the receptor is involved in (e.g., glucose level modulation, blood cell development, mitogenesis, etc.). Examples of cell receptor ligands include cytokines, growth factors, interleukins, interferons, erythropoietin (EPO), insulin, glucagon, G-protein coupled receptor ligands, etc.). Tumor suppressor genes are genes that are able to inhibit the growth of a cell, particularly tumor cells. Thus, delivery of these genes to tumor cells is useful in the treatment of cancers. Tumor suppressor genes include, but are not limited to, p53 (Lamb et al., *Mol. Cell. Biol.* 6:1379–1385 (1986), Ewen et al., *Science* 255:85–87 (1992), Ewen et al. (1991) *Cell* 66:1155–1164, and Hu et al., *EMBO J.* 9:1147–1155 (1990)), RB1 (Toguchida et al. (1993) *Genomics* 17:535–543), WT1 (Hastie, N. D., *Curr. Opin. Genet. Dev.* 3:408–413 (1993)), NF1 (Trofatter et al., *Cell* 72:791–800 (1993), Cawthon et al., *Cell* 62:193–201 (1990)), VHL (Latif et al., *Science* 260:1317–1320 (1993)) and APC (Gorden et al., *Cell* 66:589–600 (1991)). Anti-angiogenic genes are able to inhibit angiogenesis. These genes are particularly useful for treating those cancers in which angiogenesis plays a role in the pathological development of the disease. Examples of anti-angiogenic genes include, but are not limited to, endostatin (see e.g., U.S. Pat. No. 6,174,861) and angiostatin (see, e.g., U.S. Pat. No. 5,639,725).

The vectors further usually comprise selectable markers which result in nucleic acid amplification such as the sodium, potassium ATPase, thymidine kinase, aminoglycoside phosphotransferase, hygromycin B phosphotransferase, xanthine-guanine phosphoribosyl transferase, CAD (carbamyl phosphate synthetase, aspartate transcarbamylase, and dihydroorotase), adenosine deaminase, dihydrofolate reductase, and asparagine synthetase and ouabain selection. Alternatively, high yield expression systems not involving nucleic acid amplification are also suitable, such as using a baculovirus vector in insect cells, with the encoding sequence under the direction of the polyhedrin promoter or other strong baculovirus promoters.

When nucleic acids other than plasmids are used the nucleic acids can contain nucleic acid analogs, for example, the antisense derivatives described in a review by Stein, et al., *Science* 261:1004–1011 (1993) and in U.S. Pat. Nos. 5,264,423 and 5,276,019, the disclosures of which are incorporated herein by reference.

Unlike viral-based gene therapy vectors which can only incorporate a relatively small nonviral nucleic acid sequence into the viral genome because of size limitations for packaging virion particles, the lipid-nucleic acid complexes of the prtesent invention may be used to transfer large (e.g., 50–5,000 kilobase) exogenous nucleic acids into cells. This aspect of lipofection is particularly advantageous since many genes which may be targets for gene therapy span over 100 kilobases (e.g., amyloid precursor protein (APP) gene, Huntington's chorea gene) and large homologous targeting constructs or transgenes may be required for therapy.

Cells can be lipofected with an exogenous nucleic acid at high efficiency and with cell type specificity by contacting the cells with a receptor-recognition transfection complex comprising: (1) an exogenous nucleic acid, (2) a receptor-ligand protein ("rlp") which is covalently linked to a polycation, and (3) a cationic or neutral lipid. It has been found that a combination of a polycation-linked receptor-recognition protein and a suitable cationic (or neutral) lipid can be used to transfect nucleic acids, and that the combination retains cell type targeting specificity conferred by the receptor-recognition protein and also exhibits high efficiency transfection conferred, in part, by the inclusion of a cationic lipid, neutral lipid, or lipopolyarnine.

The exogenous nucleic acid is typically dsDNA, ssDNA, ssRNA, dsRNA; most typically the exogenous nucleic acid is dsDNA such as a cloned DNA sequence in a cloning vector such as a plasmid or viral genome. Multiple species of exogenous nucleic acid may be combined in a transfection complex, such as for co-transfection of unlinked nucleic acid sequences or to accomplish in vivo homologous recombination shuffling. Frequently, the exogenous nucleic acid(s) are not capable of autonomous replication in cells which incorporate the transfection complex, and are either transiently expressed or are stably integrated into a host cell chromosome by homologous recombination or nonhomologous integration. Often at least one selectable marker (e.g., a $neo^R$ expression cassette) is included in the exogenous nucleic acid(s) to facilitate selection of cells which have incorporated the exogenous nucleic acid(s). Typically, an exogenous nucleic acid comprises a structural gene encoding a polypeptide to be expressed in a target cell which has incorporated the exogenous nucleic acid, and the structural gene usually is operably linked to appropriate cis-acting regulatory elements (e.g., promoter, enhancer, polyadenylation site). Although gene therapy may be performed in a variety of ways, a typical receptor-recognition lipofection complex comprises a nucleic acid which comprises at least one transcriptional unit.

The lipid nucleic acid particles of the invention can be designed to contain, in addition to the species of nucleic acid, a receptor-recognition molecule (rlm), such as a protein. The rlm can be covalently bound to lipids that comprise the nucleic acid-lipid particle. Its presence on the particle increases the efficiency aand specificity with the particle contacts and enters target cells. For example, a suitable rlm is a nonimmunoglobulin protein that binds to a cell surface receptor of a target cell which mediates internalization of a transfection complex comprising the rlm-polycation conjugate by, for example, the process of endocytosis and/or membrane fusion. Additional suitable rim species typically are naturally-occurring physiological ligands which comprise a polypeptide portion (e.g., adhesion molecules such as ICAM-1, ICAM-2, ELAM-1, VCAM-1). Viral proteins (e.g., spike glycoproteins) which bind to viral receptors on eukaryotic cells and mediate virus internalization may also be used as rim species for forming rlm-polycation conjugates. Examples also include viral glycoproteins which attach to cell surface receptors and lead to internalization and/or membrane fusion include the gB, gC, gD, gE, gH, and gI virion glycoproteins of HSV-1, and gp120 of HIV-1.

Fragments and analogs of naturally-occurring proteins may be used as well as full-length mature proteins as rlm species in forming transfection complexes of the invention. For example, fragments, analogs, and fusion proteins comprising a portion of an adhesion molecule or virion attachment protein which mediates attachment to a target cell may be used as rlm species without other portions of the naturally-occurring full-length protein that are not essential for cell attachment and/or membrane fusion. Thus, for example, a cytoplasmic tail peptide portion of a virion glycoprotein usually may be omitted and the resultant protein may still serve as a suitable rlm.

The rim selected will vary with the particular target cell type. For specific targeting to hepatocytes, asialoglycoproteins (galactose-terminal) are preferred as rim species. Examples of asialoglycoproteins include asialoorosomucoid, asialofetuin, and desialylated vesicular stomatitis virus virion proteins. These can be formed by chemical or enzymatic desialylation of those glycoproteins that possess terminal sialic acid and penultimate galactose residues. Alternatively, rim species suitable for forming lipofection complexes that selectively target hepatocytes may be created by coupling lactose or other galactose-terminal carbohydrates (e.g., arabinogalactan) to nongalactose-bearing proteins by reductive lactosamination. Other useful galactose-terminal carbohydrates for hepatocyte targeting include carbohydrate trees obtained from natural glycoproteins, especially tri- and tetra-antennary structures that contain either terminal galactose residues or that can be enzymatically treated to expose terminal galactose residues. For targeting macrophages, endothelial cells, or lymphocytes, rim species comprising mannose or mannose-6-phosphate, or complex carbohydrates comprising these terminal carbohydrate structures may be used.

Since a variety of different cell surface receptors exist on the surfaces of mammalian cells, cell-specific targeting of nucleic acids to nonhepatic cells can involve lipofection complexes that comprise various rim species. For example, transferrin can be used as a suitable rim for forming receptor-recognition transfection complexes to cells expressing transferrin receptors. Other receptor ligands such as polypeptide hormones (e.g., growth hormone, PDGF, FGF, EGF, insulin, IL-2, IL-4, etc.) may be used to localize receptor-recognition transfection complexes to cells expressing the cognate receptor.

The nucleic acid-lipid particles may comprise multiple rIm species. Frequently, an agent having membrane fusion activity (e.g., influenza virus hemagglutinin, HSV-1 gB and gD) is used as an rlm for forming rlm-polycation complexes, either alone or in combination with other rlm species, typically with those which lack membrane fusion activity.

These transfection methods generally comprise the steps of: (1) forming a nucleic acid-lipid-rlm particle consisting essentially of an exogenous nucleic acid, a polycation conjugate consisting essentially of a polycation linked to a nonimmunoglobulin receptor-recognition molecule that binds to a predetermined cell surface receptor, and a lipid component consisting essentially of a neutral or cationic lipid (optionally including a quaternary ammonium detergent and/or a lipopolyamine), and (2) contacting cells expressing the predetermined cell surface receptor with a composition comprising the receptor-recognition transfection complex under physiological transfection conditions which permit uptake of the exogenous nucleic acid into said cells. In alternative embodiments, the rlm is attached to the polycation by covalent linkage, frequently by covalent linkage through a crosslinking agent or by peptide linkage.

III. Preparation of SPLPs and SPLP-CPLs and Sizing

In one embodiment, the present invention provides lipid-nucleic acid particles produced via hydrophobic nucleic acid-lipid intermediate complexes. The complexes are preferably charge-neutralized. Manipulation of these complexes in either detergent-based or organic solvent-based systems can lead to particle formation in which the nucleic acid is protected.

The present invention provides a method of preparing serum-stable plasmid-lipid particles in which the plasmid or other nucleic acid is encapsulated in a lipid bilayer and is protected from degradation. Additionally, the particles formed in the present invention are preferably neutral or negatively-charged at physiological pH. For in vivo applications, neutral particles are advantageous, while for in vitro applications the particles are more preferably negatively charged. This provides the further advantage of reduced aggregation over the positively-charged liposome formulations in which a nucleic acid can be encapsulated in cationic lipids.

The particles made by the methods of this invention have a size of about 50 to about 150 nm, with a majority of the particles being about 65 to 85 nm. The particles can be formed by either a detergent dialysis method or by a modification of a reverse-phase method which utilizes organic solvents to provide a single phase during mixing of the components. Without intending to be bound by any particular mechanism of formation, a plasmid or other nucleic acid is contacted with a detergent solution of cationic lipids to form a coated plasmid complex. These coated plasmids can aggregate and precipitate. However, the presence of a detergent reduces this aggregation and allows the coated plasmids to react with excess lipids (typically, noncationic lipids) to form particles in which the plasmid or other nucleic acid is encapsulated in a lipid bilayer. The methods described below for the formation of plasmid-lipid particles using organic solvents follow a similar scheme.

In some embodiments, the particles are formed using detergent dialysis. Thus, the present invention provides a method for the preparation of serum-stable plasmid-lipid particles, comprising:

(a) combining a plasmid with cationic lipids in a detergent solution to form a coated plasmid-lipid complex;

(b) contacting noncationic lipids with the coated plasmid-lipid complex to form a detergent solution comprising a plasmid-lipid complex and noncationic lipids; and (c) dialyzing the detergent solution of step (b) to provide a solution of serum-stable plasmid-lipid particles, wherein the plasmid is encapsulated in a lipid bilayer and the particles are serum-stable and have a size of from about 50 to about 150 nm.

An initial solution of coated plasmid-lipid complexes is formed by combining the plasmid with the cationic lipids in a detergent solution.

In these embodiments, the detergent solution is preferably an aqueous solution of a neutral detergent having a critical micelle concentration of 15–300 mM, more preferably 20–50 mM. Examples of suitable detergents include, for example, N,N'-((octanoylimino)-bis-(trimethylene))-bis-(D-gluconamide) (BIGCHAP); BRIJ 35; Deoxy-BIGCHAP; dodecylpoly(ethylene glycol) ether; Tween 20; Tween 40; Tween 60; Tween 80; Tween 85; Mega 8; Mega 9; Zwittergent® 3–08; Zwittergent® 3–10; Triton X-405; hexyl-, heptyl-, octyl- and nonyl-β-D-glucopyranoside; and heptylthioglucopyranoside; with octyl β-D-glucopyranoside and Tween-20 being the most preferred. The concentration of detergent in the detergent solution is typically about 100 mM to about 2 M, preferably from about 200 mM to about 1.5 M.

The cationic lipids and plasmid will typically be combined to produce a charge ratio (+/−) of about 1:1 to about 20:1, preferably in a ratio of about 1:1 to about 12:1, and more preferably in a ratio of about 2:1 to about 6:1. Additionally, the overall concentration of plasmid in solution will typically be from about 25 μg/mL to about 1 mg/mL, preferably from about 25 μg/mL to about 200 μg/mL, and more preferably from about 50 μg/mL to about 100 μg/mL. The combination of plasmids and cationic lipids in detergent solution is kept, typically at room temperature, for a period of time which is sufficient for the coated complexes to form. Alternatively, the plasmids and cationic lipids can be combined in the detergent solution and warmed to temperatures of up to about 37° C. For plasmids which are particularly sensitive to temperature, the coated complexes can be formed at lower temperatures, typically down to about 4° C.

In a preferred embodiment, the nucleic acid to lipid ratios (mass/mass ratios) in a formed SPLP will range from about 0.01 to about 0.08. The ratio of the starting materials also falls within this range because the purification step typically removes the unencapsulated nucleic acid as well as the empty liposomes. In another preferred embodiment, the SPLP preparation uses about 400 μg nucleic acid per 10 mg total lipid or a nucleic acid to lipid ratio of about 0.01 to about 0.08 and, more prederably, about 0.04, which corresponds to 1.25 mg of total lipid per 50 μg of nucleic acid.

The detergent solution of the coated plasmid-lipid complexes is then contacted with noncationic lipids to provide a detergent solution of plasmid-lipid complexes and noncationic lipids. The noncationic lipids which are useful in this step include, diacylphosphatidylcholine, diacylphosphatidylethanolamine, ceramide, sphingomyelin, cephalin, cardiolipin, and cerebrosides. In preferred embodiments, the noncationic lipids are diacylphosphatidylcholine, diacylphosphatidylethanolamine, ceramide or sphingomyelin. The acyl groups in these lipids are preferably acyl groups derived from fatty acids having $C_{10}$–$C_{24}$ carbon chains. More preferably the acyl groups are lauroyl, myristoyl, palmitoyl, stearoyl or oleoyl. In particularly preferred embodiments, the noncationic lipid will be 1,2-sn-dioleoylphosphatidylethanolamine (DOPE), palmitoyl oleoyl phosphatidylcholine (POPC) or egg phosphatidylcholine (EPC). In the most preferred embodiments, the plasmid-lipid particles will be fusogenic particles with enhanced properties in vivo and the noncationic lipid will be DOPE. In other preferred embodiments, the noncationic lipids will further comprise polyethylene glycol-based polymers such as PEG 2000, PEG 5000 and polyethylene glycol conjugated to ceramides, as described in co-pending U.S. Ser. No. 08/316,429, incorporated herein by reference.

The amount of noncationic lipid which is used in the present methods is typically about 2 to about 20 mg of total lipids to 50 μg of plasmid. Preferably the amount of total lipid is from about 5 to about 10 mg per 50 μg of plasmid.

Following formation of the detergent solution of plasmid-lipid complexes and noncationic lipids, the detergent is removed, preferably by dialysis. The removal of the detergent results in the formation of a lipid-bilayer which surrounds the plasmid providing serum-stable plasmid-lipid particles which have a size of from about 50 nm to about 150 nm. The particles thus formed do not aggregate and are optionally sized to achieve a uniform particle size.

The serum-stable plasmid-lipid particles can be sized by any of the methods available for sizing liposomes. The sizing may be conducted in order to achieve a desired size range and relatively narrow distribution of particle sizes.

Several techniques are available for sizing the particles to a desired size. One sizing method, used for liposomes and equally applicable to the present particles is described in U.S. Pat. No. 4,737,323, incorporated herein by reference. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles may be extruded through successively smaller-pore membranes, to achieve a gradual reduction in size.

In another group of embodiments, the present invention provides a method for the preparation of serum-stable plasmid-lipid particles, comprising;

(a) preparing a mixture comprising cationic lipids and noncationic lipids in an organic solvent;

(b) contacting an aqueous solution of nucleic acid with said mixture in step (a) to provide a clear single phase; and (c) removing said organic solvent to provide a suspension of plasmid-lipid particles, wherein said plasmid is encapsulated in a lipid bilayer, and said particles are stable in serum and have a size of from about 50 to about 150 nm.

The plasmids (or nucleic acids), cationic lipids and noncationic lipids which are useful in this group of embodiments are as described for the detergent dialysis methods above.

The selection of an organic solvent will typically involve consideration of solvent polarity and the ease with which the solvent can be removed at the later stages of particle formation. The organic solvent, which is also used as a solubilizing agent, is in an amount sufficient to provide a clear single phase mixture of plasmid and lipids. Suitable solvents include chloroform, dichloromethane, diethylether, cyclohexane, cyclopentane, benzene, toluene, methanol, or other aliphatic alcohols such as propanol, isopropanol, butanol, tert-butanol, iso-butanol, pentanol and hexanol. Combinations of two or more solvents may also be used in the present invention.

Contacting the plasmid with the organic solution of cationic and noncationic lipids is accomplished by mixing together a first solution of plasmid, which is typically an aqueous solution and a second organic solution of the lipids. One of skill in the art will understand that this mixing can take place by any number of methods, for example by mechanical means such as by using vortex mixers.

After the plasmid has been contacted with the organic solution of lipids, the organic solvent is removed, thus forming an aqueous suspension of serum-stable plasmid-lipid particles. The methods used to remove the organic solvent will typically involve evaporation at reduced pressures or blowing a stream of inert gas (e.g., nitrogen or argon) across the mixture.

The serum-stable plasmid-lipid particles thus formed will typically be sized from about 50 nm to 150 nm. To achieve further size reduction or homogeneity of size in the particles, sizing can be conducted as described above.

In other embodiments, the methods will further comprise adding nonlipid polycations which are useful to effect the transformation of cells using the present compositions. Examples of suitable nonlipid polycations include, hexadimethrine bromide (sold under the brandname POLYBRENE®, from Aldrich Chemical Co., Milwaukee, Wis., USA) or other salts of heaxadimethrine. Other suitable polycations include, for example, salts of poly-L-ornithine, poly-L-arginine, poly-L-lysine, poly-D-lysine, polyallylamine and polyethyleneimine.

In other embodiments, the polyoxyethylene conjugates which are used in the plasmid-lipid particles of the present invention can be prepared by combining the conjugating group (i.e. phosphatidic acid or phosphatidylethanolamine) with an appropriately finctionalized polyoxyethylene derivative. For example, phosphatidylethanolamine can be combined with polyoxyethylene bis(p-toluenesulfonate) to provide a phosphatidylethanolamine-polyoxyethylene conjugate. See, Woodle, et al., *Biochim. Biophys. Acta* 1105:193–200 (1992), incorporated herein by reference.

In certain embodiments, the formation of the lipid-nucleic acid complexes can be carried out either in a monophase system (e.g., a Bligh and Dyer monophase or similar mixture of aqueous and organic solvents) or in a two phase system with suitable mixing.

When formation of the complexes is carried out in a monophase system, the cationic lipids and nucleic acids are each dissolved in a volume of the monophase mixture. Combination of the two solutions provides a single mixture in which the complexes form. Alternatively, the complexes can form in two-phase mixtures in which the cationic lipids bind to the nucleic acid (which is present in the aqueous phase), and "pull" it in to the organic phase.

In another embodiment, the present invention provides a method for the preparation of lipid-nucleic acid particles, comprising:

(a) contacting nucleic acids with a solution comprising noncationic lipids and a detergent to form a nucleic acid-lipid mixture;

(b) contacting cationic lipids with the nucleic acid-lipid mixture to neutralize a portion of the negative charge of the nucleic acids and form a charge-neutralized mixture of nucleic acids and lipids; and (c) removing the detergent from the charge-neutralized mixture to provide the lipid-nucleic acid particles in which the nucleic acids are protected from degradation.

In one group of embodiments, the solution of noncationic lipids and detergent is an aqueous solution. Contacting the nucleic acids with the solution of noncationic lipids and detergent is typically accomplished by mixing together a first solution of nucleic acids and a second solution of the lipids and detergent. One of skill in the art will understand that this mixing can take place by any number of methods, for example by mechanical means such as by using vortex mixers. Preferably, the nucleic acid solution is also a detergent solution. The amount of noncationic lipid which is used in the present method is typically determined based on the amount of cationic lipid used, and is typically of from about 0.2 to 5 times the amount of cationic lipid, preferably about 0.5 to 2 times the amount of cationic lipid used.

The nucleic acid-lipid mixture thus formed is contacted with cationic lipids to neutralize a portion of the negative charge which is associated with the nucleic acids (or other polyanionic materials) present. The amount of cationic lipids used will typically be sufficient to neutralize at least 50% of the negative charge of the nucleic acid. Preferably, the negative charge will be at least 70% neutralized, more preferably at least 90% neutralized. Cationic lipids which are useful in the present invention, include, for example, DODAC, DOTMA, DDAB, DOTAP, DC-Chol and DMRIE. These lipids and related analogs have been described in co-pending U.S. Ser. No. 08/316,399; U.S. Pat. Nos. 5,208, 036, 5,264,618, 5,279,833 and 5,283,185, the disclosures of which are incorporated herein by reference. Additionally, a number of commercial preparations of cationic lipids are available and can be used in the present invention. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic lipids comprising DOGS in ethanol from Promega Corp., Madison, Wis., USA).

Contacting the cationic lipids with the nucleic acid-lipid mixture can be accomplished by any of a number of techniques, preferably by mixing together a solution of the cationic lipid and a solution containing the nucleic acid-lipid mixture. Upon mixing the two solutions (or contacting in any other manner), a portion of the negative charge associated with the nucleic acid is neutralized. Nevertheless, the nucleic acid remains in an uncondensed state and acquires hydrophilic characteristics.

After the cationic lipids have been contacted with the nucleic acid-lipid mixture, the detergent (or combination of detergent and organic solvent) is removed, thus forming the lipid-nucleic acid particles. The methods used to remove the detergent will typically involve dialysis. When organic solvents are present, removal is typically accomplished by evaporation at reduced pressures or by blowing a stream of inert gas (e.g., nitrogen or argon) across the mixture.

The particles thus formed will typically be sized from about 100 nm to several microns. To achieve further size reduction or homogeneity of size in the particles, the lipid-nucleic acid particles can be sonicated, filtered or subjected to other sizing techniques which are used in liposomal formulations and are known to those of skill in the art.

In other embodiments, the methods will further comprise adding nonlipid polycations which are useful to effect the lipofection of cells using the present compositions. Examples of suitable nonlipid polycations include, hexadimethrine bromide (sold under the brandname POLYBRENE®, from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine and polyethyleneimine. Addition of these salts is preferably after the particles have been formed.

In another aspect, the present invention provides methods for the preparation of lipid-nucleic acid particles, comprising:

(a) contacting an amount of cationic lipids with nucleic acids in a solution; the solution comprising of from about 15–35% water and about 65–85% organic solvent and the amount of cationic lipids being sufficient to produce a +/− charge ratio of from about 0.85 to about 2.0, to provide a hydrophobic, charge-neutralized lipid-nucleic acid complex;

(b) contacting the hydrophobic, charge-neutralized lipid-nucleic acid complex in solution with noncationic lipids, to provide a lipid-nucleic acid mixture; and (c) removing the organic solvents from the lipid-nucleic acid mixture to provide lipid-nucleic acid particles in which the nucleic acids are protected from degradation.

The nucleic acids, noncationic lipids, cationic lipids and organic solvents which are useful in this aspect of the invention are the same as those described for the methods above which used detergents. In one group of embodiments, the solution of step (a) is a monophase. In another group of embodiments, the solution of step (a) is two-phase.

In preferred embodiments, the cationic lipids are DODAC, DDAB, DOTMA, DOSPA, DMRIE, DOGS or combinations thereof. In other preferred embodiments, the noncationic lipids are ESM, DOPE, polyethylene glycol-based polymers (e.g., PEG 2000, PEG 5000, PEG-modified phospholipids or PEG-modified ceramides) or combinations thereof. In still other preferred embodiments, the organic solvents are methanol, chloroform, methylene chloride, ethanol, diethyl ether or combinations thereof.

In a particularly preferred embodiment, the nucleic acid is a plasmid; the cationic lipid is DODAC, DDAB, DOTMA, DOSPA, DMRIE, DOGS or combinations thereof; the noncationic lipid is ESM, DOPE, polyethylene glycol-based polymers or combinations thereof, and the organic solvent is methanol, chloroform, methylene chloride, ethanol, diethyl ether or combinations thereof.

As above, contacting the nucleic acids with the cationic lipids is typically accomplished by mixing together a first solution of nucleic acids and a second solution of the lipids, preferably by mechanical means such as by using vortex mixers. The resulting mixture contains complexes as described for one aspect of the invention above. These complexes are then converted to particles by the addition of noncationic lipids and the removal of the organic solvent. The addition of the noncationic lipids is typically accomplished by simply adding a solution of the noncationic lipids to the mixture containing the complexes. A reverse addition can also be used. Subsequent removal of organic solvents can be accomplished by methods known to those of skill in the art and also described above.

The amount of noncationic lipids which is used in this aspect of the invention is typically an amount of from about 0.2 to 5 times the amount (on a mole basis) of cationic lipids which was used to provide the charge-neutralized lipid-nucleic acid complex. Preferably, the amount is from 0.5 to 2 times the amount of cationic lipids used.

In yet another aspect, the present invention provides lipid-nucleic acid particles which are prepared by the methods described above. In these embodiments, the lipid-nucleic acid particles are either net charge neutral or carry an overall charge which provides the particles with greater gene lipofection activity. Preferably, the nucleic acid component of the particles is a nucleic acid which encodes a desired protein or blocks the production of an undesired protein. In particularly preferred embodiments, the nucleic acid is a plasmid, the noncationic lipid is egg sphingomyelin and the cationic lipid is DODAC.

A variety of general methods for making SPLP-CPLs (CPL-containing SPLPs) are discussed herein. Two general techniques include "post-insertion" technique, that is, insertion of a CPL into for example, a pre-formed SPLP, and the "standard" technique, wherein the CPL is included in the lipid mixture during for example, the SPLP formation steps. The post-insertion technique results in SPLPs having CPLs mainly in the external face of the SPLP bilayer membrane, whereas standard techniques provide SPLPs having CPLs on both internal and external faces.

In particular, "post-insertion" involves forming SPLPs (by any method), and incubating the pre-formed SPLPs in the presence of CPL under appropriate conditions (preferably 2–3 hours at 60° C.). Between 60–80% of the CPL can be inserted into the external leaflet of the recipient vesicle, giving final concentrations up to about 5 to 10 mol %

(relative to total lipid). The method is especially useful for vesicles made from phospholipids (which can contain cholesterol) and also for vesicles containing PEG-lipids (such as PEG-Ceramide).

In an example of a "standard" technique, the CPL-SPLPs of the present invention can be formed by extrusion. In this embodiment, all of the lipids including the CPL, are co-dissolved in chloroform, which is then removed under nitrogen followed by high vacuum. The lipid mixture is hydrated in an appropriate buffer, and extruded through two polycarbonate filters with a pore size of 100 nm. The resulting SPLPs contain CPL on both of the internal and external faces. In yet another standard technique, the formation of CPL-SPLPs can be accomplished using a detergent dialysis or ethanol dialysis method, for example, as discussed in U.S. Patent Nos. 5,976,567 and 5,981,501, both of which are incorporated herein by reference.

IV. Pharmaceutical Preparations The nucleic acid-lipid particles of the present invention can be administered either alone or in mixture with a physiologically-acceptable carrier (such as physiological saline or phosphate buffer) selected in accordance with the route of administration and standard pharmaceutical practice. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc.

The pharmaceutical carrier is generally added following particle formation. Thus, after the particle is formed, the particle can be diluted into pharmaceutically acceptable carriers such as normal saline.

The concentration of particles in the pharmaceutical formulations can vary widely, i.e., from less than about 0.05%, usually at or at least about 2–5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration.

As described above, it is often desirable to include PEG-lipid conjugates, such as PEG-ceramides or PEG-PE, ganglioside $G_{M1}$-modified lipids or ATTA-lipids to the particles. Addition of such components prevents particle aggregation and provides a means for increasing circulation lifetime and increasing the delivery of the lipid-nucleic acid particles to the target tissues. Typically, the concentration of the component in the particle will be about 1–20 % and, more preferably from about 3–10 %.

The pharmaceutical compositions may be sterilized by conventional, well known sterilization techniques. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

In another example of their use, lipid-nucleic acid particles can be incorporated into a broad range of topical dosage forms including but not limited to gels, oils, emulsions and the like. For instance, the suspension containing the nucleic acid-lipid particles can be formulated and administered as topical creams, pastes, ointments, gels, lotions and the like.

The present invention also provides lipid-nucleic acid particles in kit form. The kit will typically be comprised of a container which is compartmentalized for holding the various elements of the lipid-nucleic acid particles and the endosomal membrane destabilizer (e.g., calcium ions). The kit will contain the compositions of the present inventions, preferably in dehydrated form, with instructions for their rehydration and administration. In still other embodiments, the particles and/or compositions comprising the particles will have a targeting moiety attached to the surface of the particle. Methods of attaching targeting moieties (e.g., antibodies, proteins) to lipids (such as those used in the present particles) are known to those of skill in the art.

V. Administration of Lipid-Nucleic Acid Particle Formulations

The serum-stable nucleic acid-lipid particles of the present invention are useful for the introduction of nucleic acids into cells. Accordingly, the present invention also provides methods for introducing a nucleic acids (e.g., a plasmid) into a cell. The methods are carried out in vitro or in vivo by first forming the particles as described above, then contacting the particles with the cells for a period of time sufficient for transfection to occur.

The nucleic acid-lipid particles of the present invention can be adsorbed to almost any cell type with which they are mixed or contacted. Once adsorbed, the particles can either be endocytosed by a portion of the cells, exchange lipids with cell membranes, or fuse with the cells. Transfer or incorporation of the nucleic acid portion of the particle can take place via any one of these pathways. In particular, when fusion takes place, the particle membrane is integrated into the cell membrane and the contents of the particle combine with the intracellular fluid.

1. In Vitro Gene Transfer

For in vitro applications, the delivery of nucleic acids can be to any cell grown in culture, whether of plant or animal origin, vertebrate or invertebrate, and of any tissue or type. In preferred embodiments, the cells will be animal cells, more preferably mammalian cells, and most preferably human cells.

Contact between the cells and the lipid-nucleic acid particles, when carried out in vitro, takes place in a biologically compatible medium. The concentration of particles varies widely depending on the particular application, but is generally between about 1 μmol and about 10 mmol. Treatment of the cells with the nucleic acid-lipid particles is generally carried out at physiological temperatures (about 37° C.) for periods of time of from about 1 to 48 hours, preferably of from about 2 to 4 hours.

In one group of preferred embodiments, a lipid-nucleic acid particle suspension is added to 60–80% confluent plated cells having a cell density of from about $10^3$ to about $10^5$ cells/mL, more preferably about $2\times10^4$ cells/mL. The concentration of the suspension added to the cells is preferably of from about 0.01 to 0.2 μg/mL, more preferably about 0.1 μg/mL.

2. In Vivo Gene Transfer

Alternatively, the compositions of the present invention can also be used for the in vivo gene transfer, using methods which are known to those of skill in the art. In particular, Zhu, et al., *Science* 261:209–211 (1993), incorporated herein by reference, describes the intravenous delivery of cytomegalovirus (CMV)-chloramphenicol acetyltransferase (CAT) expression plasmid using DOTMA-DOPE complexes. Hyde, et al., *Nature* 362:250–256 (1993), incorporated herein by reference, describes the delivery of the cystic fibrosis transmembrane conductance regulator (CFTR) gene to epithelia of the airway and to alveoli in the lung of mice, using liposomes. Brigham, et al., *Am. J. Med. Sci.* 298: 278–281 (1989), incorporated herein by reference, describes the in vivo transfection of lungs of mice with a functioning prokaryotic gene encoding the intracellular enzyme chloramphenicol acetyltransferase (CAT).

For in vivo administration, the pharmaceutical compositions are preferably administered parenterally, i.e., intraarticularly, intravenously, intraperitoneally, subcutaneously, or intramuscularly. More preferably, the pharmaceutical compositions are administered intravenously or intraperitoneally by a bolus injection. For example, see Stadler, et al., U.S. Pat. No. 5,286,634, which is incorporated herein by reference. Intracellular nucleic acid delivery has also been discussed in Straubringer, et al., *METHODS IN ENZYMOLOGY*, Academic Press, New York. 101:512–527 (1983); Mannino, et al., *Biotechniques* 6:682–690 (1988); Nicolau, et al., *Crit. Rev. Ther. Drug Carrier Syst.* 6:239–271 (1989), and Behr, *Acc. Chem. Res.* 26:274–278 (1993). Still other methods of administering lipid-based therapeutics are described in, for example, Rahman et al., U.S. Pat. No. 3,993,754; Sears, U.S. Pat. No. 4,145,410; Papahadjopoulos et al., U.S. Pat. No. 4,235,871; Schneider, U.S. Pat. No. 4,224,179; Lenk et al., U.S. Pat. No. 4,522,803; and Fountain et al., U.S. Pat. No. 4,588,578.

In certain embodiments, the pharmaceutical preparations may be contacted with the target tissue by direct application of the preparation to the tissue. The application may be made by topical, "open" or "closed" procedures. By "topical", it is meant the direct application of the pharmaceutical preparation to a tissue exposed to the environment, such as the skin, oropharynx, external auditory canal, and the like. "Open" procedures are those procedures which include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or metrazamide imaging of the spinal cord. Alternatively, the preparations may be administered through endoscopic devices.

The lipid-nucleic acid particles can also be administered in an aerosol inhaled into the lungs (see, Brigham, et al., *Am. J. Sci.* 298(4):278–281 (1989)) or by direct injection at the site of disease (Culver, *HUMAN GENE THERAPY*, MaryAnn Liebert, Inc., Publishers, New York. pp.70–71 (1994)).

The methods of the present invention may be practiced in a variety of hosts. Preferred hosts include mammalian species, such as humans, nonhuman primates, dogs, cats, cattle, horses, sheep, and the like.

The amount of particles administered will depend upon the the ratio of nucleic acid to lipid; the particular nucleic acid used, the disease state being diagnosed; the age, weight, and condition of the patient and the judgement of the clinician; but will generally be between about 0.01 and about 50 mg per kilogram of body weight; preferably between about 0.1 and about 5 mg/kg of body weight or about $10^8$–$10^{10}$ particles per injection.

3. Insertion of Functional Copy of a Gene

Some methods of gene therapy serve to compensate for a defect in an endogenous gene by integrating a functional copy of the gene into the host chromosome. The inserted gene replicates with the host DNA and is expressed at a level to compensate for the defective gene. Diseases amendable to treatment by this approach are often characterized by recessive mutations. That is, both copies of an endogenous gene must be defective for symptoms to appear. Such diseases include cystic fibrosis, sickle cell anemia, β-thalassemia, phenylketonuria, galactosemia, Wilson's disease, hemochromatosis, severe combined immunodeficiency disease, alpha-1-antitrypsin deficiency, albinism, alkaptonuria, lysosomal storage diseases, Ehlers-Danlos syndrome, hemophilia, glucose-6-phosphate dehydrogenase deficiency, agammaglobulimenia, diabetes insipidus, Lesch-Nyhan syndrome, muscular dystrophy, Wiskott-Aldrich syndrome, Fabry's disease, fragile X-syndrome, and the like. Other recessive mutations are known in the art, and the use of the methods of the present invention to treat them is contemplated herein.

There are several methods for introducing an exogenous functional gene to compensate for the above genetic defects. In one approach, cells are removed from a patient suffering from the disease and contacted with a lipid-vector complex in vitro. Cells should be removed from a tissue type in which disease symptoms are manifested. If the cells are capable of replication, and the vector used includes a selective marker, cells having internalized and expressed the marker can be selected. Particularly if selection is not performed, it is important that the frequency of gene transfer into cells be high, for example, at least about 1, 5, 10, 25 or 50% of cells.

After integration of the vector into the cellular genome, and optionally, selection, cells are reintroduced into the patient. In this application, and others discussed below (except site-specific recombination to correct dominant mutations), it is not necessary that the gene supplied by the lipid-nucleic acid particle be delivered to the same site as is occupied by the defective gene for which it is compensating.

Alternatively, the lipid-vector complex can be introduced directly into a patient as a pharmaceutical composition. The complex is delivered to the tissue(s) affected by the genetic disorder being treated in a therapeutically effective dose. In this and other methods, a therapeutically effective dose is an amount sufficient to cure, or at least partially arrest, the symptoms of the disease and its complications. Effective doses of the compositions of the present invention, for the treatment of the above described conditions will vary depending upon many different factors, including means of administration, target site, physiological state of the patient, and other medicants administered. Thus, treatment dosages will need to be titrated to optimize safety and efficacy. Doses ranging from about 10 ng to 1 g, 100 ng to 100 mg, 1 μg to 10 mg, or 30–300 μg DNA per patient are typical. Routes of administration include oral, nasal, gastric, intravenous, intradermal and intramuscular.

The nucleic acid-lipid complexes can also be used to transfect embryonic stem cells or zygotes to achieve germline alterations. See Jaenisch, *Science,* 240:1468–1474 (1988); Gordon et al., *Methods Enzymol.* 101, 414 (1984); Hogan et al., *Manipulation of the Mouse Embryo: A Laboratory Manual*, C.S.H.L. N.Y. (1986); and Hammer et al., *Nature* 315:680 (1985); Gandolfi et al., *J. Reprod. Fert.* 81:23–28 (1987); Rexroad et al., *J. Anim. Sci.* 66:947–953 (1988) and Eyestone et al., *J. Reprod. Fert.* 85:715–720 (1989); Camous et al., *J. Reprod. Fert.* 72:779–785 (1984); Heyman et al., *Theriogenology* 27:5968 (1987). However, these methods are presently more suitable for veterinary applications that human treatment due to ethical and regulatory constraints in manipulating human embryos.

As an example, cystic fibrosis (CF) is a usually fatal recessive genetic disease, having a high incidence in Caucasian populations. The gene responsible for this disease was isolated by Riordan et al, *Science* 245:1059–1065 (1989). It encodes a protein called the cystic fibrosis transmembrane conductance regulator (CFTR) which is involved in the transfer of chloride ions ($Cl^-$) through epithelial cell membranes. Mutations in the gene cause defects of $Cl^-$ secretion in epithelial cells leading to the various clinical manifestations. Although CF has a number of symptoms including thickened exocrine gland secretions, pancreatic deficiency, intestinal blockage and malabsorption of fat, the most serious factor affecting mortality is chronic lung disease. Accordingly, to treat a CF patient, a vector containing a coding sequence for a functional CFTR gene product can be complexed with lipid, and optionally, a pharmaceutical excipient and introduced into the patient via nasal administration so that the vector-lipid composition reaches the lungs. The dose of vector-lipid complex is preferably about $10^8$–$10^{10}$ particles.

As another example, defects in the α or γ globin genes (see McDonagh & Nienhuis in *Hematology of Infancy and Childhood* (eds. Nathan & Oski, Saunders, Pa., 1992) at pp. 783–879) can be compensated for by ex vivo treatment of hemopoietic stem cells with an nucleic acid-lipid complex containing a functional copy of the gene. The gene integrates into the stem cells which are then reintroduced into the patient. Defects in the gene responsible for Fanconi Anemia Complement Group C can be treated by an analogous strategy (see Walsh et al., *J. Clin. Invest.* 94:1440–1448 (1994)).

Other applications include the introduction of a functional copy of a tumor suppressor gene into cancerous cell or cells at risk of becoming cancerous. Individuals having defects in one or both copies of an endogenous tumor suppressor gene are particularly at risk of developing cancers. For example, Li-Fraumeni syndrome is a hereditary condition in which individuals receive mutant p53 alleles, resulting in the early onset of various cancers (Harris, *Science* 262:1980–1981 (1993) Frebourg et al., *PNAS* 89:6413–6417 (1992); Malkin et al., *Science* 250:1233 (1990)). Expression of a tumor suppressor gene in a cancerous cell or a cell at risk of becoming cancerous is effective to prevent, arrest and/or reverse cellular proliferation and other manifestations of the cancerous state. Suitable tumor suppressor genes for use in the invention include p53 (Buchman et al., *Gene* 70:245–252 (1988)), APC, DCC, Rb, WT1, and NF1 (Marx, *Science* 260:751–752 (1993); Marshall, *Cell* 64:313–326 (1991)). Lipid-nucleic acid complexes bearing a functional copy of a tumor suppressor gene are usually administered in vivo by the route most proximal to the intended site of action. For example, skin cancers can be treated by topical administration and leukemia by intravenous administration.

4. Suppression of Gene Expression

Methods of gene therapy using the nucleic acid-lipid complexes of the invention can also be used for prophylactic or therapeutic treatment of patients or cells, infected with or at risk of being infected with, a pathogenic microorganism, such as HIV. The effectiveness of antisense molecules in blocking target gene functions of impeding virus replication has been demonstrated in a number of different systems (Friedman et al., *Nature* 335:452–54 (1988), Malim et al., *Cell* 58:205–14 (1989) & Trono at al., *Cell* 59:113–20 (1989)). The vector used includes a DNA segment encoding an antisense transcript, which is complementary to a segment of the genome from the pathogenic microorganism. The segment should preferably play an essential role in the lifecycle of the microorganism, and should also be unique to the microorganism (or at least absent from the genome of the natural genome of a patient undergoing therapy). For example, suitable sites for inhibition on the HIV virus includes TAR, REV or nef (Chatterjee et al., *Science* 258: 1485–1488 (1992)). Rev is a regulatory RNA binding protein that facilitates the export of unspliced HIV pre MRNA from the nucleus. Malim et al., *Nature* 338:254 (1989). Tat is thought to be a transcriptional activator that functions by binding a recognition sequence in 5' flanking mRNA. Karn & Graeble, *Trends Genet.* 8:365 (1992). The nucleic acid-lipid complex is introduced into leukocytes or hemopoietic stem cells, either ex vivo or by intravenous injection in a therapeutically effective dose. The treatment can be administered prophylactically to HIV-persons, or to persons already infected with HIV.

Analogous methods are used for suppressing expression of endogenous recipient cell genes encoding adhesion proteins. Suppression of adhesion protein expression in useful in aborting undesirable inflammatory responses. Adhesion proteins that can be suppressed by antisense segments present in seelcted vectors include integrins, selectins, and immunoglobulin (Ig) superfamily members (see Springer, *Nature* 346:425–433 (1990). Osbom, *Cell* 62:3 (1990); Hynes, Cell 69:11 (1992)). Integrins are heterodimeric transmembrane glycoproteins consisting of an a chain (120–180 kDa) and a β chain (90–110 kDa), generally having short cytoplasmic domains. The three known integrins, LFA-1, Mac-1 and P150,95, have different alpha subunits, designated CD11a, CD11b and CD11c, and a common beta subunit designated CD 18. LFA-1 ($\alpha_L\beta_2$) is expressed on lymphocytes, granulocyte and monocytes, and binds predominantly to an Ig-family member counter-receptor termed ICAM-1 (and perhaps to a lesser extent ICAM-2). ICAM-1 is expressed on many cells, including leukocytes and endothelial cells, and is up-regulated on vascular endothelium by cytokines such as TNF and IL-1. Mac-1 ($\alpha_M\beta_2$) is distributed on neutrophils and monocytes, and also binds to ICAM-1 (and possibly ICAM-2). The third β2 integrin, P150,95 ($\alpha_X\beta_2$), is also found on neutrophils and monocytes. The selectins consist of L-selectin, E-selectin and P-selectin.

5. Cells to be Transformed

The compositions and methods of the present invention are used to treat a wide variety of cell types, in vivo and in vitro. Among those most often targeted for gene therapy are hematopoietic precursor (stem) cells. Other cells include those of which a proportion of the targeted cells are nondividing or slow dividing. These include, for example, fibroblasts, keratinocytes, endothelial cells, skeletal and smooth muscle cells, osteoblasts, neurons, quiescent lymphocytes, terminally differentiated cells, slow or noncycling primary cells, parenchymal cells, lymphoid cells, epithelial cells, bone cells, etc. The methods and compositions can be employed with cells of a wide variety of vertebrates, including mammals, and especially those of veterinary importance, e.g, canine, feline, equine, bovine, ovine, caprine, rodent, lagomorph, swine, etc., in addition to human cell populations.

To the extent that tissue culture of cells may be required, it is well known in the art. Freshney (1994) (*Culture of Animal Cells, a Manual of Basic Technique*, third edition Wiley-Liss, New York), Kuchler et al. (1977) *Biochemical Methods in Cell Culture and Virology*, Kuchler, R. J., Dowden, Hutchinson and Ross, Inc., and the references cited therein provides a general guide to the culture of cells. Cultured cell systems often will be in the form of monolayers of cells, although cell suspensions are also used.

Gene therapy relies on the efficient delivery of therapeutic genes to target cells. Most of the somatic cells that have been targeted for gene therapy, e.g., hematopoietic cells, skin fibroblasts and keratinocytes, hepatocytes, endothelial cells, muscle cells and lymphocytes, are normally nondividing. Retroviral vectors, which are the most widely used vectors for gene therapy, unfortunately require cell division for effective transduction (Miller et al., *Mol. Cell. Biol.* 10:4239–4242 (1990)). This is also true with other gene therapy vectors such as the adeno-associated vectors (Russell et al., *Proc. Natl. Acad. Sci. USA* 91:8915–8919 (1994); Alexander et al., *J. Virol.* 68:8282–8287 (1994); Srivastrava, *Blood Cells* 20:531–538 (1994)). Recently, HIV-based vectors has been reported to transfect nondividing cells. Nonetheless, the majority of stem cells, a preferred target for many gene therapy treatments, are normally not proliferating. Thus, the efficiency of transduction is often relatively low, and the gene product may not be expressed in therapeutically or prophylactically effective amounts. This has led investigators to develop techniques such as stimulating the stem cells to proliferate priot to or during gene transfer (e.g., by treatment with growth factors) pretreatment with 5-fluorouracil, infection in the presence of cytokines, and extending the vector infection period to increase the likelihood that stem cells are dividing during infection, but these have met with limited success.

6. Detection of Foreign Nucleic Acids

After a given cell is transduced with a nucleic acid construct that encodes a gene of interest, it is important to detect which cells or cell lines express the gene product and to assess the level of expression of the gene product in engineered cells. This requires the detection of nucleic acids that encode the gene products.

Nucleic acids and proteins are detected and quantified herein by any of a number of means well known to those of skill in the art. These include analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like. The detection of nucleic acids proceeds by well known methods such as Southern analysis, northern analysis, gel electrophoresis, PCR, radiolabeling, scintillation counting, and affinity chromatography.

The selection of a nucleic acid hybridization format is not critical. A variety of nucleic acid hybridization formats are known to those skilled in the art. For example, common formats include sandwich assays and competition or displacement assays. Hybridization techniques are generally described in "*Nucleic Acid Hybridization, A Practical Approach*," Ed. Hames, B. D. and Higgins, S. J., IRL Press, 1985.

The sensitivity of the hybridization assays may be enhanced through use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as Mullis et al. (1987), U.S. Pat. No. 4,683,202; *PCR Protocols A Guide to Methods and Applications* (Innis et al. eds) Academic Press Inc. San Diego, Calif. (1990) (Innis); Amheim & Levinson (Oct. 1, 1990), *C&EN* 36–47; *The Journal Of NIH Research,* 3:81–94 (1991); (Kwoh et al., *Proc. NatL Acad. Sci. USA,* 86:1173 (1989); Guatelli et al., *Proc. Natl. Acad. Sci. USA,* 87:1874 (1990); Lomell et al., *J. Clin. Chem.,* 35:1826 (1989); Landegren et al., *Science,* 241:1077–1080 (1988); Van Brunt, *Biotechnology,* 8:291–294 (1990); Wu and Wallace, *Gene,* 4:560 (1989); Barringer et al., *Gene,* 89:117 (1990), and Sooknanan and Malek, *Biotechnology,* 13:563–564 (1995). Improved methods of cloning in vitro amplified nucleic acids are described in Wallace et al., U.S. Pat. No. 5,426,039. Other methods recently described in the art are the nucleic acid sequence based amplification (NASBA™, Cangene, Mississauga, Ontario) and Q Beta Replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation.

Oligonucleotides for use as probes, e.g., in in vitro amplification methods, for use as gene probes, or as inhibitor components are typically synthesized chemically according to the solid phase phosphoramidite triester method described by Beaucage and Caruthers, *Tetrahedron Letts.,* 22(20): 1859–1862 (1981), e.g., using an automated synthesizer, as described in Needham-VanDevanter et al., *Nucleic Acids Res.,* 12:6159–6168 (1984). Purification of oligonucleotides, where necessary, is typically performed by either native acrylamide gel electrophoresis or by anion-exchange HPLC as described in Pearson and Regnier, *J. Chrom.,* 255:137–149 (1983). The sequence of the synthetic oligonucleotides can be verified using the chemical degradation method of Maxam and Gilbert (1980) in Grossman and Moldave (eds.) Academic Press, New York, *Methods in Enzymology,* 65:499–560.

An alternative means for determining the level of expression of the gene is in situ hybridization. In situ hybridization assays are well known and are generally described in Angerer et al., *Methods Enzymol.,* 152:649–660 (1987). In an in situ hybridization assay cells are fixed to a solid support, typically a glass slide. If DNA is to be probed, the cells are denatured with heat or alkali. The cells are then contacted with a hybridization solution at a moderate temperature to permit annealing of specific probes that are labelled. The probes are preferably labelled with radioisotopes or fluorescent reporters.

7. Detection of Foreign Gene Products

The expression of the gene of interest to produce a product may be detected or quantified by a variety of methods. Preferred methods involve the use of specific antibodies.

Methods of producing polyclonal and monoclonal antibodies are known to those of skill in the art. See, e.g., *Coligan (*1991), *CURRENT PROTOCOLS IN IMMUNOLOGY*, Wiley/Greene, NY; and Harlow and Lane (1989), *ANTIBODIES: A LABORATORY MANUAL*, Cold Spring Harbor Press, NY; Stites et al. (eds.) *BASIC AND CLINICAL IMMUNOLOGY* (4th ed.) Lange Medical Publications, Los Altos, Calif., and references cited therein; Goding (1986), *MONOCLONAL ANTIBODIES: PRINCIPLES AND PRACTICE* (2d ed.) Academic Press, New York, N.Y.; and Kohler and Milstein, *Nature,* 256:495–497 (1975). Such techniques include antibody preparation by selection of antibodies from libraries of recombinant antibodies in phage or similar vectors. See, Huse et al., *Science,* 246:1275–1281 (1989); and Ward et al., *Nature,* 341:544–546 (1989). Specific monoclonal and polyclonal antibodies and antisera will usually bind with a $K_D$ of at least about 0.1 mM, more usually at least about 1 μM, preferably at least about 0.1 μM or better, and most typically and preferably, 0.01 μM or better.

The presence of a desired polypeptide (including peptide, transcript, or enzymatic digestion product) in a sample may be detected and quantified using Western blot analysis. The technique generally comprises separating sample products by gel electrophoresis on the basis of molecular weight, transferring the separated proteins to a suitable solid support, (such as a nitrocellulose filter, a nylon filter, or derivatized nylon filter), and incubating the sample with labeling antibodies that specifically bind to the analyte protein. The labeling antibodies specifically bind to analyte on the solid support. These antibodies are directly labeled, or alternatively are subsequently detected using labeling agents such as antibodies (e.g., labeled sheep anti-mouse antibodies where the antibody to an analyte is a murine antibody) that specifically bind to the labeling antibody.

V. EXAMPLES

Example I

The Effect of Calcium on the Transfection Potency of SPLP

A. Materials and Methods

1. Materials. N,N-dioleyl-N,N-dimethylammonium chloride (DODAC) as obtained from Dr. S. Ansell and 1-O-(2-(ω-methoxyethyleneglycol)succinoyl)-2-N-arachidoylsphingosine (PEG-Cer$C_{20}$) was synthesized by Dr. Z. Wang at Inex Pharmaceuticals Corporation (Burnaby, BC). 1,2-dioleoyl-sn-glycero-3-phosphoethanolamine (DOPE) and 1,2-dioleoyl-sn-glycero-3-phosphocholine (DOPC) were obtained from Northern Lipids (Vancouver, BC). 1,2-dioleoyl-sn-glycero-3-(phospho-L-serine) (DOPS) and 1,2-dioleoyl-sn-glycero-3-phosphoethanolamine-N-(Lissamine Rhodarnine B Sulfonyl) (Rh-DOPE) were purchased from Avanti Polar Lipids (Alabaster, Ala.). Cholesterol (Chol), octylglucopyranoside (OGP), HEPES, $MgCl_2$, and NaCl were obtained from Sigma Chemical Co. (St. Louis, Mo.). DEAE Sepharose CL-6B anionic-exchange column and Sepharose CL-4B sizing column materials were obtained from Sigma Chemical Co. (St. Louis, Mo.). The luciferase assay kit was purchased from Promega Corp. (Madison, Wis.). Picogreen dsDNA detection reagent was obtained from Molecular Probes (Eugene, Oreg.). Plasmid DNA (pCMVLuc) coding for the luciferase reporter gene under the control of the human CMV immediate early promoter-enhancer element was obtained from Inex Pharmaceuticals Corporation (Burnaby, BC). Bovine hamster kidney (BHK) cells were obtained from the American Tissue Culture Collection (ATCC CCL-10, Rockville, Md.) and cultured in Dulbecco modified Eagle medium (DMEM) supplement with 10% fetal bovine serum (FBS), 100 U/ml of penicillin and 100 μg/ml of streptomycin. BHK cells were maintained as a monolayer at 37° C. in a humidified atmosphere containing 5.0% $CO_2$.

2. Preparation of SPLP. SPLP were prepared as described by Wheeler, et al., *Gene Therapy* 6:271–281 (1999)) with some modifications. Briefly, a total of 10 μmoles of DODAC, DOPE, PEG-Cer$C_{20}$ (7:83:10; mol/mol/mol) were dissolved in chloroform and dried under a stream of nitrogen gas. Residual solvent was removed under high vacuum for 2 h. The resulting lipid film was hydrated in 1 ml of HBS buffer (20 mM HEPES and 150 mM NaCl, pH 7.5) containing 0.2 M OGP with continuous vortexing. Plasmid DNA (400 μg/ml) was added to the hydrated lipids and the mixtures were dialysed against HBS buffer for 36 to 48 h with 2 buffer changes. Nonencapsulated plasmid was removed by DEAE anion exchange chromatography and empty lipid vesicles were removed by employing a sucrose density gradient as previously described (Mok, et al., *Biochimica et Biophysica Acta* 1419:137–150 (1999)). For the high DODAC content formulation (DODAC/DOPE/PEG-Cer$C_{20}$, 14:76:10, mol/mol/mol), SPLP were initially prepared in HBS buffer containing 30 mM sodium citrate as described previously (Zhang, et al., *Gene Therapy* 6:1438–1447 (1999)). SPLP were characterized with respect to plasmid entrapment using a previously described Picogreen assay (Zhang, et al., *Gene Therapy* 6:1438–1447 (1999)) and sized using quasielastic light scattering.

3. Transfection in the presence of $Ca^{2+}$. Prior to transfection, BHK cells were plated at a density of $1\times10^4$ cells per well in a 96-well plate overnight. 200 mM $CaCl_2$ stock solution was prepared in $dH_2$ and sterilized by filtering. 0.5 μg plasmid DNA encapsulated in SPLP was used per well of transfection. SPLP were first added to appropriate concentrations of $Ca^{2+}$ as required by the experiment, after which culture media was added to the mixtures to obtain the final transfection volume of 100 μl/well. $Ca^{2+}$ concentration was calculated with respect to the final volume of the transfection medium applied to cells. The final volume contained 20% vol $Ca^{2+}$ and SPLP mixtures and 80% vol culture media. Cells were incubated with the transfection complexes for the appropriate time 5 periods before assaying for gene expression as described previously (Wheeler, et al., *Gene Therapy* 6:271–281 (1999)). Relative luciferase activity was normalized against total cellular protein determined by using the Micro BCA protein assay reagent kit (Pierce, Ill.).

4. Determination of cellular lipid uptake. BHK cells were plated at $1\times10^5$ cells per well of 12-well plates the day prior to the experiment. SPLP were prepared with 0.5 mol % Rh-DOPE incorporated into the lipid formulations. SPLP mixed with increasing concentrations of $Ca^{2+}$ (0 to 14 mM) were added to cells at a lipid dose of 80 nmoles in complete media (1 ml final volume). After incubation at 37° C. for 4, 8, and 24 h, cells were washed with PBS and lysed by the addition of buffer containing 0.1% TX-100 in 250 mM phosphate buffer (pH 8.0). Rhodamine fluorescence of the lysate was measured on a Perkin Elmer Luminescence Spectrophotometer using $\lambda_{ex}$ of 560 nm and $\lambda_{em}$ of 590 nm with slit widths of 10 and 10 nm, respectively. Lipid uptake was determined by comparing lysate fluorescence to that of a lipid standard normalizing it to the total cellular protein. To determine the intracellular SPLP localization, fluorescence microscopy was employed. Cells were transfected with vesicles labeled with 4 mol % Rh-DOPE. The transfection media was replaced with complete media prior to analysis under the fluorescence microscope. Fluorescence micrographs were taken on an Axiovert 100 Zeiss Fluorescent microscope (Carl Zeiss Jena GmbH) using a rhodamine filter from Omega Opticals (Brattleboro, Vt.) with the following specifications, $\lambda_{ex}$=560±20 nm, 600 µm LP, and DC 590 nm.

5. $^{31}P$ NMR spectroscopy. Solid-state $^{31}P$ NMR spectra were recorded with broad-band decoupling at 81.02 MHz on a Bruker MSL 200 spectrometer, using a 3.8-µs 60° pulse and a 1.5-s repeat time. The free induction decay (FID) was accumulated over 2500–3000 scans and was Fourier transformed with 50-Hz line broadening. Phospholipid mixtures (25 µmol of total phospholipid) were dispersed by vortex mixing in 2 ml of buffer (20 mM HEPES buffer, pH 7.4). Increasing concentrations of $Ca^{2+}$ were titrated into the vesicles by adding aliquots of 200 mM $CaCl_2$ stock. $Ca^{2+}$ equilibration was ensured by performing three cycles of freeze-thawing. The temperature was maintained at 25 ° C. with a Bruker variable temperature unit. A mixture of phosphoric acid/$D_2O$ was used as the reference for chemical shifts in all $^{31}P$ NMR spectra.

6. Intracellular processing of plasmid DNA. BHK cells were plated at $3\times10^5$ cells per well of 6-well plates the day prior to the experiment. 2.5 µg plasmid DNA encapsulated in SPLP were incubated with cells for 2, 4, and 8 h, in the absence or presence (8 mM) of $Ca^{2+}$. At the appropriate time points, cells were washed with PBS and external SPLP were removed by trypsinization. Trypsinized cells were pelleted by centrifugation and cells were resuspended and washed with isotonic buffer (250 mM sucrose, 3 mM $MgCl_2$, 50 mM HEPES, pH 7.2). Subsequently, pelleted cells were lysed by incubating with 250 µl of lysis buffer (10 mM Tris, pH 7.5, 0.5% SDS, 1 mM EDTA) containing Pronase E at 1 mg/ml (Sigma) overnight at 37° C. DNA (genomic DNA and delivered plasmid DNA) were extracted as described previously (Sambrook, et al., In *Molecular Cloning: A Laboratory Manual* I, 1.21–1.52 (1989). Cold Spring Harbor, N.Y., C. Nolan, editor. Cold Spring Harbor Laboratory). DNA recovery was determined by measuring the absorbance at 260 nm. 6 µg of total DNA from each sample was either dot blotted onto a nylon transfer membrane (Amersham) with a set of pCMVLuc standards (0 to 5 pg) or loaded into a 1% agarose gel and size fractionated at 60 V for 2 h for the Southern analysis. Both blots were hybridized overnight at 68° C. to a $^{32}P$-labeled plasmid DNA probe, which was prepared with PstI cut-pCMVLuc plasmid using the $^{T7}$QuickPrime™ Kit (Pharmacia Biotech). Blots were washed 3 times with 2×SSC containing 0.1% SDS, and were then exposed on a Phospholmager screen which was subsequently scanned (Molecular Dynamics—Phospholmager™SI).

7. Entrapment of $Ca^{2+}$ inside SPLP. SPLP (DODAC/DOPE/PEG-CerC20/Rd-DOPE, 10:79.5:10:0.5, mol/mol/mol) were initially prepared in citrate buffer (150 mM sodium citrate and 150 mM citric acid) at pH 4. Nonencapsulated plasmid was removed by DEAE anion exchange chromatography equilibrated in HBS buffer (pH 7.5) and empty lipid vesicles were removed by employing a sucrose density gradient as previously described (Mok, et al., *Biochimica et Biophysica Acta* 1419:137–150 (1999)). $Ca^{2+}$ loading was performed by incubation of the DNA-loaded vesicles with 2.5 mM $CaCl_2$ and the ionophores A23187 (0.1 µg/µmole lipids) for 30 min at room temperature. Unloaded $Ca^{2+}$ and ionophores were removed by dialysis in HBS buffer with 2 buffer changes. Internal $Ca^{2+}$ concentrations were determined in the absence and presence of TX-100 (0.2%) by employing the membrane nonpermeant absorbant indicator Asenazo III (0.1 mM in 10 mM HEPES buffer, pH 7), against a $CaCl_2$ standard curves (0 to 50 nmoles). Absorbances at 650 nm were measured as an indicator of $Ca^{2+}$ presence. SPLP were characterized with respect to plasmid entrapment using a previously described Picogreen assay (Zhang, et al., *Gene Therapy* 6:1438–1447 (1999)) and sized using quasielastic light scattering. Internal concentrations of $Ca^{2+}$ were found to be ~175 mM.

8. Insertion of CPL. Prior to CPL insertion, SPLP were prepared as described in the previous section with some modification. SPLP containing total of 10 µmoles of DODAC, DOPE, PEG-$CerC_{20}$, and Rd-DOPE (7:82.5:10:0.5; mol/mol/mol/mol) were hydrated in 1 ml of HBS buffer (20 mM HEPES and 150 mM NaCl, pH 7.5) containing 0.2 M OGP with continuous vortexing. Plasmid DNA (400 µg/ml) was added to the hydrated lipids and the mixtures were dialysed against HBS buffer for 36 to 48 h with 2 buffer changes. Nonencapsulated plasmid was removed by DEAE anion exchange chromatography. CPL stocks in methanol labeled with a dansyl fluorescence marker were added to the SPLP to give the desired molar ratio (up to 4 mol % CPL relative to vesicle lipid). CPL and SPLP were incubated for up to 3 h at 60° C., and cooled on ice to room temperature. Both empty lipid vesicles and noninserted CPL were removed by employing a sucrose density gradient. The insertion levels of CPL were quantitated by using the Perkin Elmer Luminescence Spectrophotometer. Briefly, initial dansyl/rhodamine ($D/R_i$) fluorescence ratio prior to sucrose density gradient and the final D/R ($D/R_f$) ratio of the isolated CPL-SPLP were measured. Rhodamine flouresence was assayed at $\lambda_{ex}$=560 nm and $\lambda_{em}$=590 nm, while dansyl fluorescence was assayed at $\lambda_{ex}$=340 nm and $\lambda_{em}$=510 nm, with slit widths of 10 and 10 nm. The %-insertion was calculated as follows:

$$\%\text{-insertion}=([D/R]_f)*\ 100/(D/R)_i$$

CPL-SPLP were further characterized with respect to plasmid entrapment using a previously described Picogreen assay (Zhang et al., 1999) and sized using quasielastic light scattering.

B. Results

1. The transfection potencies of SPLP are dramatically enhanced in the presence of $Ca^{2+}$. Previous work has shown that SPLP, particularly SPLP stabilized by PEG-$CerC_{20}$, can exhibit lower levels of transfection in vitro (Wheeler, et al., *Gene Therapy* 6:271–281 (1999); Mok et al., *Biochimica et Biophysica Acta,* 1419:137–150 (1999)). Here, the effects of $Ca^{2+}$ on the transfection potency of SPLP were examined. SPLP prepared from DOPE/DODAC/PEG-$CerC_{20}$ (84:6:10; mol:mol:mol) lipid mixture and pCMVLuc employing the detergent dialysis method were purified from empty vesicles and unencapsulated plasmid as described in the above Materials and Methods. Appropriate amounts of $CaCl_2$ were then added to the SPLP preparation to give rise to the desired $Ca^{2+}$ concentrations following dilution into the media before applying to the BHK cells. The BHK cells and the SPLP were incubated together for 24 h, after which the transfected cells were assayed for luciferase expression.

As shown in FIG. 1, the presence of $Ca^{2+}$ resulted in dramatic enhancements in luciferase expression levels, with a ~600-fold increase in SPLP transfection potency observed at the optimal $Ca^{2+}$ concentrations. This $Ca^{2+}$-mediated increase in transfection is significantly greater for the SPLP system than previously observed for plasmid DNA-cationic lipid complexes. The optimal concentrations of $Ca^{2+}$ required for stimulating SPLP transfection potencies were in the range of 8 to 10 mM, somewhat lower than that required (5–25 mM) for optimal stimulation of the transfection potencies of plasmid DNA-cationic lipid complexes. Further, the ability of $Ca^{2+}$ to stimulate the transfection potency of SPLP was highly specific. As shown in FIG. 1, if $MgCl_2$ or NaCl was substituted for $CaCl_2$ no enhancement in transfection potency was observed.

2. SPLP are stable in the presence of $Ca^{2+}$. SPLP with PEG-$CerC_{20}$ are highly stable systems that exhibit extended circulation times in vivo, protect encapsulated plasmid from external nucleases, and do not interact readily with cells (Wheeler, et al., *Gene Therapy* 6:271–281 (1999); Mok, et al., *Biochimica et Biophysica Acta* 1419:137–150 (1999); Monck, et al., *Journal of Drug Targeting* 7:439–452 (2000)). It was therefore important to demonstrate that the enhanced transfection properties of SPLP in the presence of $Ca^{2+}$ was not due to destabilization or aggregation of the SPLP leading to enhanced cell uptake. The stability of the SPLP in the presence of $Ca^{2+}$ was examined employing quasi-elastic light scattering (QELS) to detect changes in size and the Picogreen fluorophore assay to detect DNA leakage. For the QELS experiments, $CaCl_2$ was added to the SPLP suspension to achieve concentrations as high as 50 mM. No change in the SPLP size or size distribution was observed. For the plasmid release experiments, SPLP were incubated at 37° C. in HBS buffer containing 10% FBS in the presence or absence of 8 mM $Ca^{2+}$. Plasmid release was assayed over 24 h employing the Picogreen assay. No plasmid release was observed.

Figure 2:
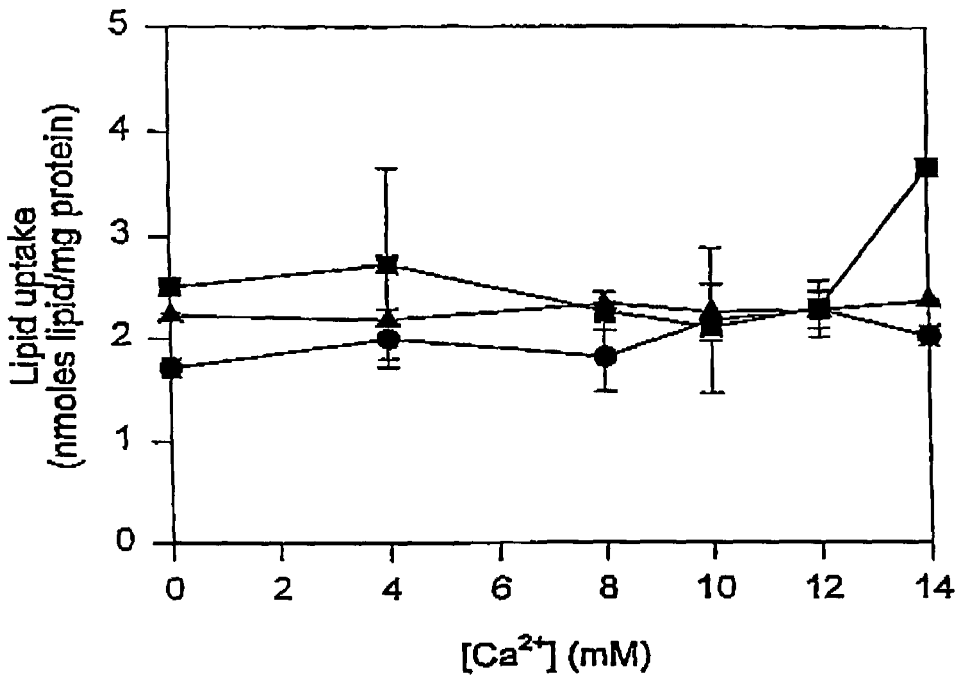
FIG. 2. Effect of $Ca^{2+}$ on the cellular uptake of SPLP. SPLP containing 0.5 mol % Rd-labeled DOPE (DODAC/DOPE/PEG-CerC20/Rh-DOPE; 7:82.5:10:0.5 mol/mol/mol/mol) were employed to monitor cellular lipid uptake. 80 nmoles of lipid vesicles prepared in the presence of $Ca^{2+}$ (0 to 14 mM) were incubated on cells until the appropriate time periods. Levels of lipid uptake were determined by measuring Rd fluorescence at 4 h (●), 8 h (■), or 24 h (▲) as described in Materials and Methods, Example I. All experiments were performed in triplicate.

3. $Ca^{2+}$ does not influence the cellular uptake of SPLP. The ability of $Ca^{2+}$ to enhance the transfection activity of plasmid DNA-cationic lipid complexes has been attributed to an increase in the uptake of the complexes into cells in the presence of $Ca^{2+}$ (Lam, et al., *Biochim Biophys Acta* 1463: 279–290 (2000)). In this regard, the low transfection potencies of SPLP as compared to complexes arise, at least in part, from very low levels of cellular uptake of SPLP (Mok, et al., *Biochimica et Biophysica Acta* 1419:137–150 (1999)). It was therefore of interest to determine whether $Ca^{2+}$ stimulated SPLP transfection potencies by increasing SPLP uptake into cells. SPLP containing 0.5 mol % Rh-DOPE were employed to determine SPLP uptake into BHK cells in the presence of up to 12 mM $Ca^{2+}$ as described in the above Materials and Methods. The SPLP were incubated with cells for 4, 8, and 24 h and the levels of intracellular lipid determined. Lipid uptake at each time-point was normalized against total cell protein in order to account for cell growth. As shown in FIG. 2, the results indicate that $Ca^{2+}$ did not significantly increase the cellular uptake of SPLP even though the transfection potencies of the SPLP varied by several hundred-fold over the range of $Ca^{2+}$ concentrations tested.

Figure 3:
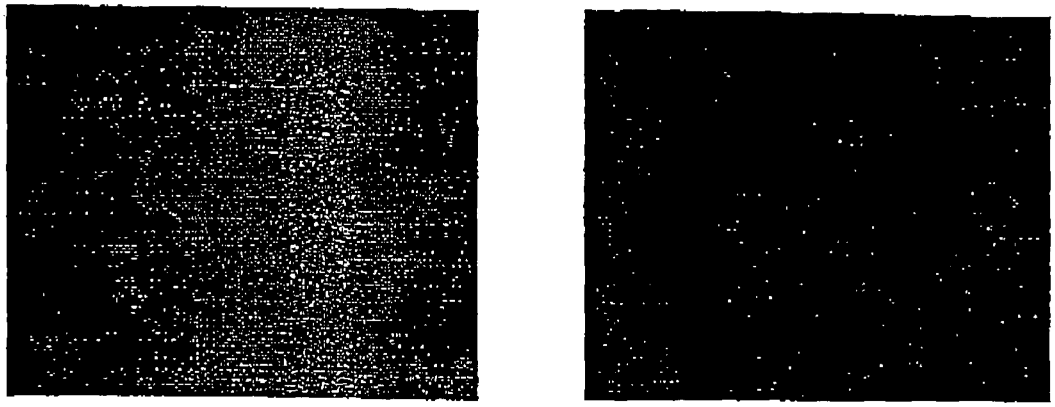
FIG. 3. Fluorescence micrographs of the cellular localization of SPLP. 100 nmoles of 4 mol % Rh-DOPE labeled vesicles were incubated on cells (plated at $1\times10^5$ cells per well of a 12-well plate) in the absence (A) or presence (B) of calcium (10 mM). At 8 h time point, transfecting media was replaced with complete DMEM media and cells were examined using fluorescence microscopy. Fluorescence micrographs were taken on an Axiovert 100 Zeiss Fluorescence microscope (Carl Zeiss Jena GmbH) using a rhodamine filter from Omega Opticals (Brattleboro, Vt.) with the following specifications, $\lambda_{ex}$=560±20 nm, 600 nm LP, and DC 590 nm.

4. Fluorescence studies indicate enhanced endosomal destabilization following SPLP uptake in the presence of $Ca^{2+}$. The fact that uptake of SPLP is not stimulated by addition of $Ca^{2+}$ suggests that the $Ca^{2+}$-dependent enhancement of transfection must arise from more efficient utilization of SPLP that are accumulated. One possibility is that $Ca^{2+}$ somehow facilitates destabilization of endosomes following uptake of SPLP, thus enhancing intracellular delivery of plasmid. Previous work has shown that endosomal destabilization following uptake of vesicles containing fluorescently-labeled lipids can be detected by fluorescence microscopy as a diffuse intracellular fluorescence, whereas uptake into stable endosomes gives rise to a localized "punctate" appearance (Felgner, et al., *Proc. Natl. Acad. Sci. USA* 84:7413–7417 (1987)). In order to be able to visualize the cellular distribution of SPLP, a higher level of Rh-DOPE (4 mol %) was incorporated with the vesicle formulation. Such Rh-labeled SPLP were incubated on BHK cells in the presence and absence of 10 mM $Ca^{2+}$ and the cell morphology was examined at 8 h by fluorescence microscopy. Similar levels of rhodamine fluorescence were detected in the absence or presence of $Ca^{2+}$, in agreement with the quantitative measurements of SPLP uptake noted in the previous section. However, as shown in FIG. 3, the appearance of the cells as detected by fluorescence microscopy was quite different in the presence or absence of $Ca^{2+}$. Although some punctate structures are observed, BHK cells containing the fluorescently-labeled SPLP exhibited a more diffuse pattern when $Ca^{2+}$ was included. In the absence of $Ca^{2+}$, the fluorescence pattern was largely punctate, consistent with SPLP retention in the endosomal compartments.

Figure 4:
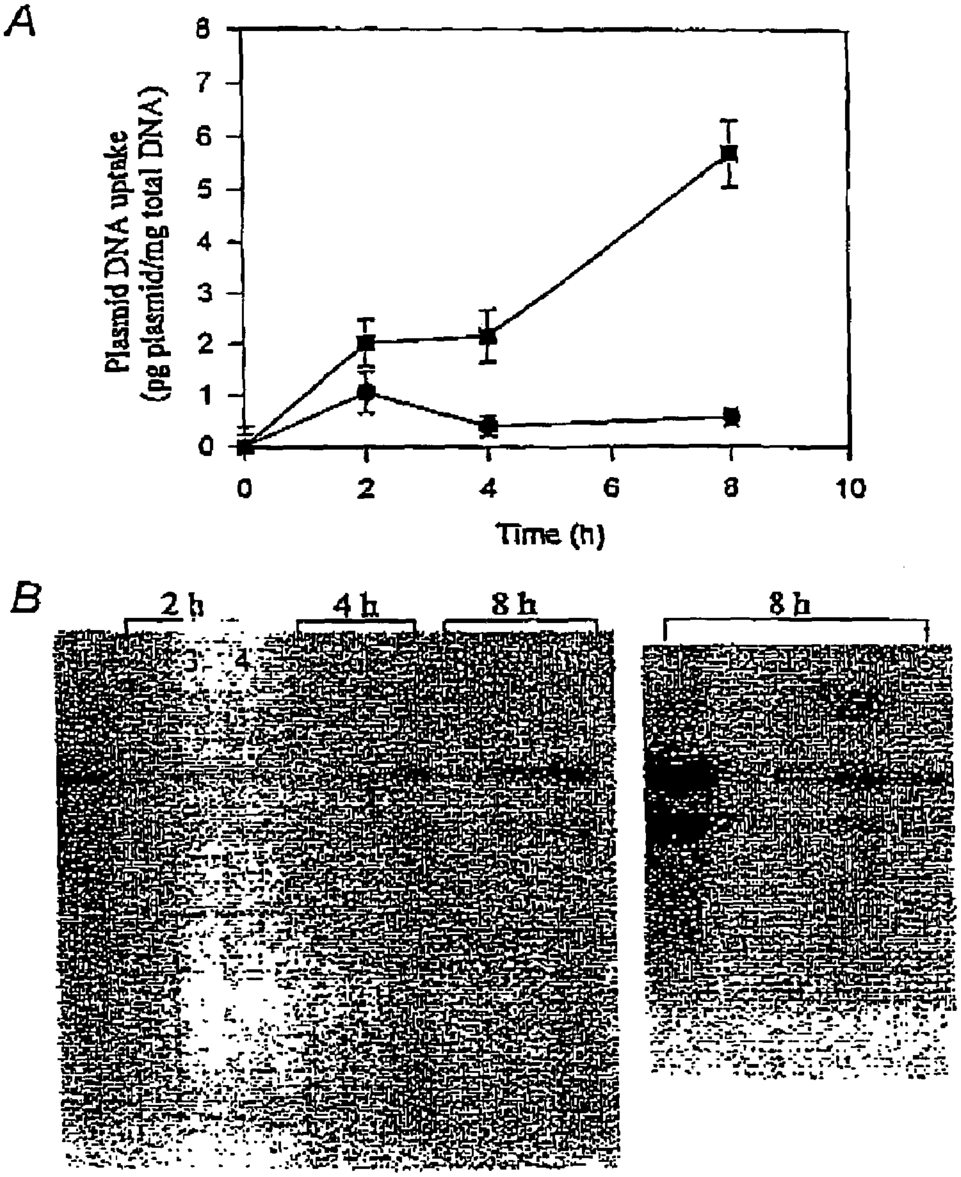
FIG. 4. Intracellular processing of plasmid DNA was affected by the presence of $Ca^{2+}$. SPLP containing 2.5 μg plasmid DNA was used to transfect BHK cells in the absence (●) or presence (■) of 8 mM $Ca^{2+}$ as described in Materials and Methods, Example I. At appropriate time points (2 h, 4 h, and 8 h), DNA was extracted from the cells and intracellular DNA was detected by hybridization to a specific $^{32}$P-labeled plasmid DNA probe. (A) Levels of plasmid DNA uptake determined by dot blot analysis as described in Materials and Methods. (B) Integrity of intracellular plasmid DNA determined by Southern blot analysis. Lanes 1 and 11: pCMVLuc control; lanes 2, 5, 8 and 12: untransfected control; lanes 3, 6, 9 and 13: cells transfected with SPLP; lanes 4, 7, 10 and 14: cells transfected with SPLP and 8 mM $Ca^{2+}$; and lane 15: cells transfected with SPLP and 8 mM $Mg^{2+}$. All experiments were performed in triplicate.

5. Intracellular processing of plasmid DNA. The preceding fluorescent microscopy results suggest that $Ca^{2+}$ enhances transfection by destabilizing the endosomal compartments, thus enhancing cytoplasmic delivery of the SPLP-associated plasmid. If SPLP plasmid can escape from the endosome more readily in the presence of $Ca^{2+}$, it will avoid breakdown in the lysosomal pathway and more intact intracellular plasmid DNA should be present. A dot blot assay was employed to measure intracellular delivery of plasmid DNA, and the integrity of the plasmid was examined by using the Southern blot analysis. Cells were incubated with SPLP in the absence or presence of 8 mM $Ca^{2+}$ for 2, 4, and 8 h. The levels of intact, intracellular plasmid DNA for the different systems were compared after isolation of DNA from the cells as described in the above Materials and Methods, and the results are shown in FIG. 4. As shown in FIG. 4A, when cells were transfected with the SPLP in the presence of $Ca^{2+}$, the amount of intact plasmid in the BHK cells was increased by approximately 10-fold after an 8 h incubation period. This is also reflected by a Southern analysis which showed that more intact plasmid DNA was present in cells transfected with SPLP prepared in the presence of $Ca^{2+}$ (FIG. 4B). Such enhanced levels of intact plasmid DNA were not observed when Mg+was substituted for $Ca^{2+}$, demonstrating the specificity of $Ca^{2+}$ (FIG. 4B).

6. $Ca^{2+}$ destabilizes bilayer lipid structures in a manner consistent with an ability to destabilize endosomal membranes. Recent work suggests that cationic lipids stimulate intracellular delivery of macromolecules such as plasmid DNA by combining with anionic lipids and forming ion pairs that destabilize bilayer membranes by inducing non-bilayer ($H_{II}$ phase) structure. In this regard, it is well known that $Ca^{2+}$ can destabilize lipid bilayers containing acidic lipids such as phosphatidylserine (PS) in combination with unsaturated PEs by inducing the nonbilayer hexagonal $H_{II}$ phase structure (Hope, et al., *FEBS Letters* 107:323–326 (1979); Tilcock, et al., *Biochimica et Biophysica Acta* 641: 189–201 (1981)). It has also been shown that $Ca^{2+}$ can induce $H_{II}$ phase structure in related systems containing phosphatidylcholine (PC) and cholesterol. For example, addition of $Ca^{2+}$ to mixtures of DOPC/DOPE/DOPS/Cholesterol (1:1:1:3; molar ratios) also triggers bilayer to hexagonal $H_{II}$ phase transitions (Tilcock, et al., *Biochemistry* 23:2696–2703 (1984)). It is thus possible that $Ca^{2+}$ stimulates SPLP transfection by acting in concert with the cationic lipid in the SPLP to destabilize the lipid bilayer of endosomal membranes.

Figure 5:
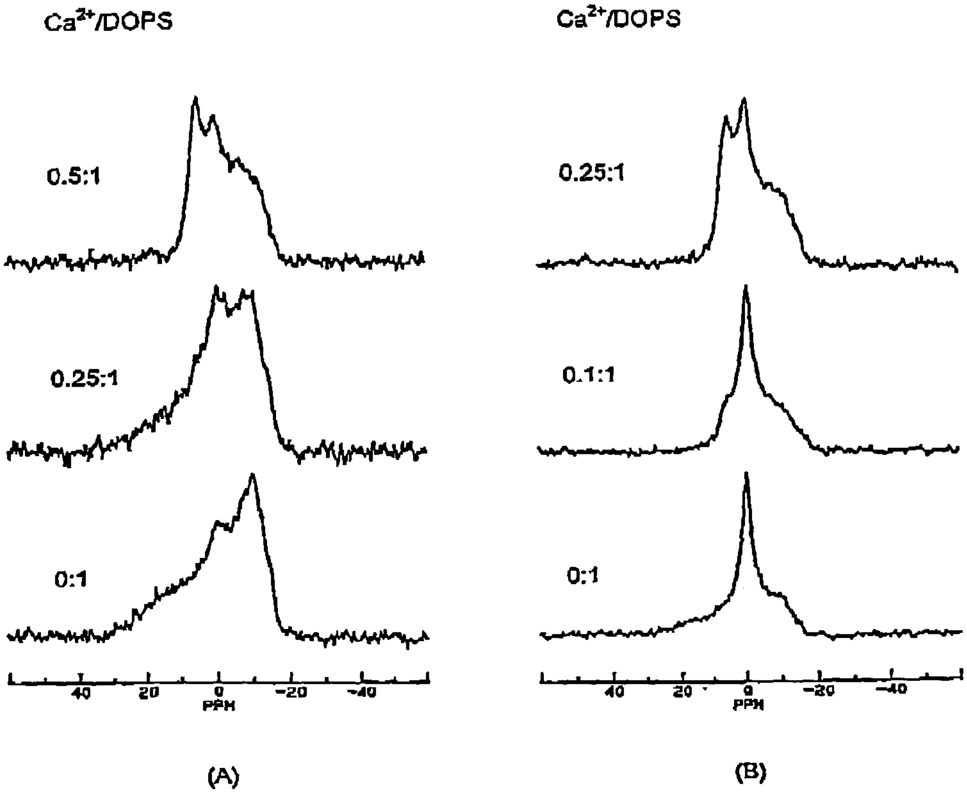
FIG. 5. $^{31}$P NMR spectra of various model membrane systems in the presence of $CaCl_2$. (A) $Ca^{2+}$ was titrated into the vesicles (DOPE/DOPS/DOPC/Chol, 1:1:1:3) at $Ca^{2+}$/DOPS ratios ranging from 0:1 to 0.5:1 (molar ratios). (B) $Ca^{2+}$ was titrated into the vesicles (DOPE/DOPS/DOPC/Chol/DODAC, 1:1:1:3:0.25) at $Ca^{2+}$/DOPS ratios ranging from 0:1 to 0.25:1 (molar ratios). Equilibration of the cations across the lipid bilayers was ensured by three cycles of freeze-thawing. Spectra have been scaled to the same peak height. Experiments were carried out as described in Materials and Methods, Example I.

In order to investigate this possibility, the $Ca^{2+}$-dependent polymorphism of MLV composed of DOPC/DOPE/DOPS/Chol (1:1:1:3; molar ratios) was investigated in the absence and presence of small amounts of DODAC employing $^{31}$p NMR. Considerable previous work has shown that phospholipids in the bilayer organization give rise to asymmetric $^{31}$P NMR line shapes with a low field shoulder and high field peak, whereas phospholipids in the hexagonal $H_{II}$ phase give rise to a line shape with reversed asymmetry that is a factor of two narrower (Cullis, et al., *Biochimica et Biophysica Acta* 559:399–420 (1979)). As shown in FIG. 5A, in the absence of DODAC, $Ca^{2+}$ is able to stimulate a transition from the bilayer to the hexagonal $H_{II}$ phase as reported by $^{31}$P NMR at the $Ca^{2+}$-to-DOPS ratio of 0.5:1. Alternatively, in MLV containing small amounts of DODAC (DOPC/DOPE/DOPS/Cholesterol/DODAC; 1:1:1:3:0.25; molar ratios), $Ca^{2+}$-to-DOPS ratios of only 0.25:1 are required to induce predominantly $H_{II}$ phase structure (FIG. 5B). The narrow central peak may arise from small lamellar structures or lipid in nonbilayer structures such the as cubic phase in which component phospholipids experience isotropic motional averaging.

Figure 6:
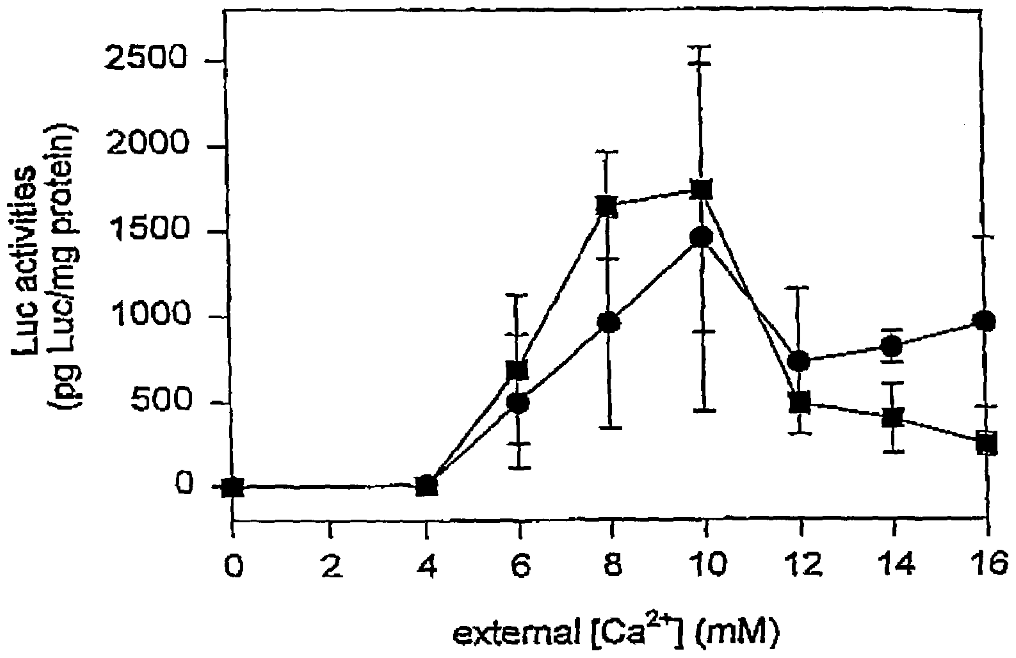
FIG. 6. Effect of $Ca^{2+}$-containing SPLP on transfection. $Ca^{2+}$ was loaded employing A23187 in the presence of a pH gradient as described in Materials and Methods. Increasing concentrations of $Ca^{2+}$ (0 to 14 mM) were added to both SPLP (■) and $Ca^{2+}$-containing SPLP (●) prior to DMEM dilution. 0.5 μg of pCMVLuc plasmid encapsulated in SPLP were used to transfect cells plated at $1\times10^4$ cells/well of 96-well plates. Luc activity was measured as described in Materials and Methods, Example I. All experiments were performed in triplicate.

7. External $Ca^{2+}$ is required to enhance SPLP transfection potency. A final set of experiments was conducted to determine whether $Ca^{2+}$ encapsulated within the SPLP could stimulate transgene expression. As detailed elsewhere (Felgner, et al., *Journal of Biological Chemistry* 269:2550–2561 (1994)), $Ca^{2+}$ can be loaded into large unilamellar vesicles (LUV) in response to a pH gradient (inside acidic) when the $Ca^{2+}$ ionophore A23187 is present. Internal $Ca^{2+}$ concentrations as high as 200 mM can be achieved. As described in the above Materials and Methods, SPLP could be readily prepared at pH 4 in the presence of a citrate buffer and then the external pH could be raised to pH 7.5 following the detergent dialysis procedure. Addition of external $CaCl_2$ and ionophore then resulted in loading of $Ca^{2+}$ into the SPLP to achieve internal concentrations of ~175 mM. As shown in FIG. 6, although the presence of encapsulated $Ca^{2+}$ result in enhancement of SPLP transfection potency, it appears that external levels of $Ca^{2+}$ play the dominant roles in stimulating the transfection process.

8. Effect of $Ca^{2+}$ on improved SPLP systems. One limitation of SPLP is that the system is not optimally taken by cells as a result of limited cationic lipid and presence of PEG on the vesicles (Mok, et al., *Biochimica et Biophysica Acta* 1419:137–150 (1999)). One straightforward way to increase the positive charges is by increasing the cationic content (Zhang, et al., *Gene Therapy* 6:1438–1447 (1999)). However, transfection efficiencies increased with SPLP increased DODAC concentrations, and such systems are thus compromised with lower DNA encapsulation. Recently, a new class of cationic lipid known as cationic poly(ethylene glycol) lipid conjugates (CPL) has been synthesized (Chen, et al., *Bioconjugate Chem.* 11:433–437 (2000)). A typical CPL employed in this study contains a hydrophobic ceramide anchor, which is attached to a hydrophilic PEG spacer that is linked to a cationic headgroup made of four lysine residues. It has been shown that SPLP w/ CPL inserted onto its surface show enhanced interaction between the liposomes and cell plasma membrane (Chen, et al., *Bioconjugate Chem.* 11:433–437 (2000)).

Figure 7:
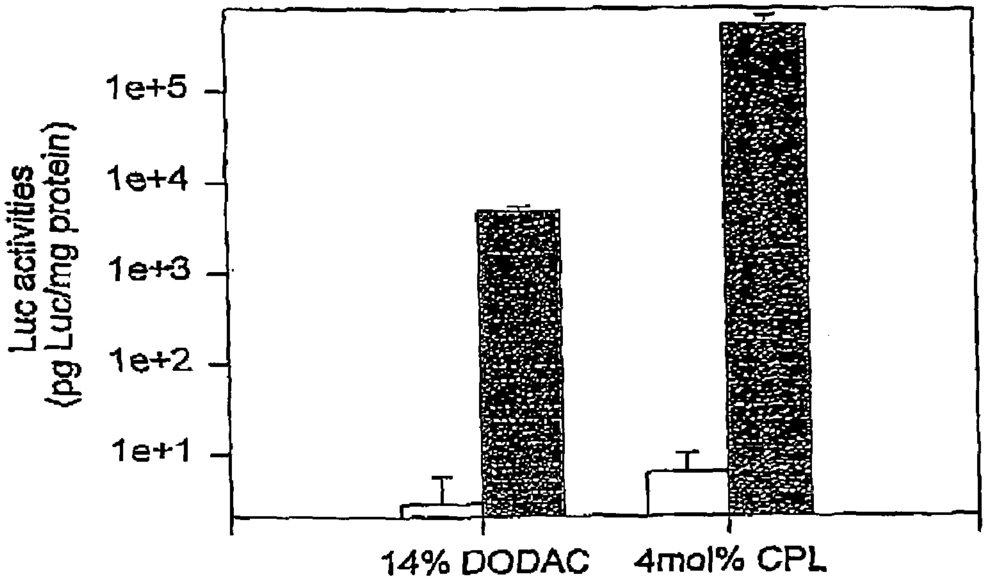
FIG. 7. Effect of $Ca^{2+}$ on improved SPLP systems. SPLP containing higher DODAC content (14 mol %) or CPL (4 mol %) were used to transfection cells in the presence (dashed bars) or absence (open bars) of 8 mM $Ca^{2+}$. 0.5 μg of pCMVLuc was used in each formulation in each transfection experiment. Cells were exposed to the vesicles for 24 h before assaying for Luc expression, as outlined in Materials and Methods, Example I. Experiments were performed in triplicate.

Experiments were carried out to determine the influence of $Ca^{2+}$ on the CPL-SPLP system. SPLP containing higher DODAC content (14 mol %) was also included. For the CPL-SPLP preparation, plasmid DNA was loaded into liposomes using the previously described detergent dialysis method and CPL were inserted into the preformed SPLP using a characterized insertion method. CPL were inserted to obtain a final 4 mol % insertion efficiency, as this level has been shown to provide optimal cellular binding and uptake. $Ca^{2+}$ at 8 mM was added to the SPLP and CPL-SPLP preparations, diluted into the media before applying to the BHK cells. Gene expression was determined by assaying for luciferase, 24 h after incubation of the BHK cells together with the transfecting liposomes. As shown in FIG. 7, a ~2000-fold increase and a $10^5$-fold increase in transfection were detected for the SPLP containing either higher DODAC content or CPL, respectively.

C. Discussion

This example demonstrates that $Ca^{2+}$ gives rise to a large enhancement of SPLP transfection potency in vitro.

The mechanism whereby $Ca^{2+}$ stimulates the transfection potency of SPLP must account for several observations. First, the enhanced transfection appears to result from higher intracellular levels of intact plasmid in the presence of $Ca^{2+}$; these higher levels of plasmid do not appear to arise from increased uptake of SPLP into cells, however. Second, the process is associated with a reduction in the "punctate" appearance of cells following uptake of fluorescently labeled SPLP. Finally, the effect is $Ca^{2+}$ specific. The first two observations are clearly consistent with enhanced endosomal destabilization of the BHK cells following endocytosis of SPLP. The question thus remaining is how $Ca^{2+}$ could promote this destabilization in a specific manner. In this regard, there is presently no consensus as to how endosomes can be destabilized to enhance release of their contents, however a number of leading observations have been made. Chief amongst these is the observation that cationic lipids can dramatically enhance the intracellular delivery of macromolecules such as plasmids and antisense oligonucleotides (Bennett, et al., *Mol. Pharmacol.* 41:1023–1033 (1992); Barron, et al., *Gene Ther.* 6:1179–1183 (1999)) and that this process appears to rely on an ability of cationic lipids to destabilize endosomal membranes, thus facilitating intracellular release of endosomal contents (Wattiaux, et al., *FEBS Letters* 417:199–202 (1997); Xu, et al., *Biochemistry* 35:5616–5623 (1996)). Recent work has shown that cationic lipids exhibit as a general property the ability to combine with anionic lipids to form nonbilayer hexagonal $H_{II}$ phase structure, leading to the proposal that the mechanism whereby cationic lipids destabilize endosomes relies on an ability to disrupt the bilayer organization of the endosomal membrane. In the same vein, if $Ca^{2+}$ could disrupt bilayer organization and induce $H_{II}$ phase structure similar enhancements in intracellular delivery would be expected.

There is considerable evidence that $Ca^{2+}$ can induce $H_{II}$ phase structure in previously bilayer lipid systems containing anionic lipids, and that this effect is $Ca^{2+}$-specific, as other cations such as $Mg^{2+}$ either cannot induce $H_{II}$ structure or require higher concentrations to produce similar effects (Tilcock, et al., *Biochemistry,* 23:2696–2703 (1984)). As shown in the present example, $Ca^{2+}$ can induce $H_{II}$ phase structure in bilayers composed ofDOPC:DOPE:DOPS:Chol and can act in synergy with low levels of the cationic lipid DODAC to trigger $H_{II}$ phase formation. While it is difficult to directly relate the model membrane behaviour to the behaviour inside the endosome, it is known that the anionic lipid content of endosomes increases as they move from "early" to "late" stages due to formation of a novel acidic lipid (lysobisphosphatidic acid; LBPA) and that mixtures of LBPA with cationic lipids such as DODAC adopt the $H_{II}$ phase. These results therefore support the theory that $Ca^{2+}$ enhances transfection by promoting endosomal destabilization in synergy with cationic lipid. Such a proposal is also in agreement with the observation that the addition of $Ca^{2+}$ to LBPA results in formation of the $H_{II}$ phase. Other workers have suggested that $Ca^{2+}$ plays a role in mediating endosomal release during calcium phosphate ($CaP_i$) mediated transfection (Loyter, et al., *Proc. Natl. Acad. Sci. USA* 79:422–426 (1982); Orrantia, et al., *Experimental Cell Research* 190:170–174 (1990)), as well as in polycation-mediated gene transfer (Bottger, et al., *Biochimica et Biophysica Acta* 1395:78–87 (1998); Haberland, et al., *Biochimica et Biophysica Acta* 1445:21–30 (1999)).

A surprising aspect of the present study concerns the discrepancy between the influence of $Ca^{2+}$ on the transfection properties of plasmid DNA-cationic lipid complexes previously reported (Lam, et al., *Biochim. Biophys. Acta* 1463:279–290 (2000)) and the results reported here for SPLP. In particular, the previous work demonstrated that $Ca^{2+}$ could enhance the transfection potency of complexes by up to 20-fold and that this could be attributed to enhanced uptake of the complexes into the cells, rather than enhanced endosomal release. The surprising aspect is that the increased transfection potency of SPLP in the presence of $Ca^{2+}$ could not be related to increased uptake of SPLP by the cells, whereas $Ca^{2+}$ caused at least a 2-fold increase in uptake of complexes as evidenced by uptake of both lipid and plasmid (Lam, et al., *Biochim Biophys Acta* 1463: 279–290 (2000)). It is likely that this discrepancy is related to the much different physical properties of SPLP as compared to complexes. Complexes are large, positively charged systems containing high (equimolar) levels of cationic lipid, whereas SPLP are small, stable, essentially neutral vesicles with a PEG coating that contain low levels of cationic lipid. The low levels of cationic lipid in SPLP as compared to complexes may be directly related to enhanced sensitivity to $Ca^{2+}$, as the cationic lipid present in the SPLP may be insufficient to combine with all available anionic lipid in the endosome, thus requiring the additional presence of $Ca^{2+}$ to achieve maximum destabilization.

The final topic of discussion concerns extension of the results presented here to generate SPLP that exhibit enhanced transfection potencies in vivo. As emphasized elsewhere (Wheeler, et al., *Gene Therapy* 6:271–281 (1999); Zhang, et al., *Gene Therapy* 6:1438–1447 (1999)), a preferred method of SPLP delivery is by systemic application, where long circulation lifetimes and accumulation at disease sites such as tumour sites is required. The present results suggest that $Ca^{2+}$ is preferably outside the SPLP in order to give rise to enhanced transfection. To achieve this, strategies aimed at increasing surface $Ca^{2+}$ concentrations by attachment of $Ca^{2+}$-chelating agents to SPLP should give rise to enhanced in vivo transfection. In addition, a local increase in calcium concentration can be produced at the site of transfection, e.g., by local (e.g., intratumoral) delivery of the SPLP along with a high concentration of calcium, or by systemic delivery of the SPLP combined with local delivery of calcium to the desired site of transfection.

Example II

Stabilized Plasmid-Lipid Particles Containing Cationic PEG Lipids Exhibit Enhanced Transfection Potencies A. Materials and Methods 1. Materials. DOPE was obtained from Northern Lipids Inc. (Vancouver, BC). Rh-PE, and PicoGreen were obtained from Molecular Probes (Eugene, Oreg.). DODAC was synthesized and supplied by Dr. S. Ansell of Inex Pharmaceuticals (Vancouver, BC). PEG-$CerC_{20}$ was synthesized as indicated elsewhere (Webb, et al., *Biochim. Biophys. Acta* 1372:272–282 (1998)) and was supplied by Dr. Z. Wang of Inex Pharmaceuticals (Vancouver, BC). The pCMVLuc plasmid encodes the *Photinus pyralis* luciferase gene under the control of the human CMV early promoter and was supplied by Dr. P. Tam of Inex Pharmaceuticals (Vancouver, BC). The pCMVGFP plasmid contains the gene for the green fluorescent protein from Aequorea Victoria and was supplied by Dr. P. Tam of Inex Pharmaceuticals (Vancouver, BC). DEAE-Sepharose CL-6B, Sepharose CL-4B, octyl-β-D-galactoside, and HEPES were obtained from Sigma-Aldrich (Oakville, ON). Lipofectin was obtained from Gibco BRL (Burlington, ON). BHK cells were obtained from Dr. R. MacGillivray of the Department of Biochemistry and Molecular Biology, UBC.

2. Preparation of SPLP-$CPL_4$. SPLP composed of DOPE:DODAC:PEG-$CerC_{20}$ (84:6:10) and containing the plasmid pCMVLuc (or pCMVGFP) were prepared according to the method of Wheeler, et al. (*Gene Therapy* 6:271–281 (1999)) using purification by anion exchange (DEAE-Sepharose CL-6B) chromatography and sucrose density gradient centrifugation to remove unencapsulated plasmid and empty vesicles, respectively. SPLP containing Rh-PE were prepared by dissolving Rh-PE with other component lipids in $CHCl_3$ at a molar ratio of 83.5:10:6:0.5 (DOPE:DODAC:PEG-$CerC_2$0:Rh-PE) prior to forming the lipid film.

$CPL_4$ was inserted into preformed SPLP by incubating SPLP (500 nmol lipid) with $CPL_4$ (12.5, 19, and 30 nmol) at 60° C. for 2 to 3 h in Hepes buffered saline (HBS), pH 7.5, unless otherwise indicated. Unincorporated $CPL_4$ was removed by gel filtration chromatography on a Sepharose CL-4B column equilibrated in HBS. Fractions (1 ml) were collected and assayed for $CPL_4$, phospholipid and DNA content. Fractions containing all three components were pooled and concentrated. $CPL_4$ content was determined by the fluorescence of the dansyl labeled CPL at $\lambda_{em}$=510 nm following excitation at $\lambda_{ex}$=340 nm employing a Perkin Elmer LS52 Luminescence spectrophotometer with excitation and emission slit widths of 10 and 20 nm, respectively. A standard curve was derived from a stock solution of dansylated CPL in HBS. For SPLP containing Rh-PE the phospholipid content was determined from the fluorescence of the Rh label measured at $\lambda_{em}$=590 nm following excitation at $\lambda_{ex}$=560 nm, using excitation and emission slit widths of 10 and 20 nm, respectively. For SPLP that did not contain the Rh label, phospholipid was determined using the method of Fiske-Subbarow (*J. Biol. Chem.* 66:375–400 (1925)) following lipid extraction according to Bligh and Dyer (*Can. J Biochem. Physiol.* 37:911–917 (1959)). Plasmid DNA was determined using the PicoGreen Assay kit (Molecular Probes, Eugene, Oregon) as previously described (Mok, et al., *Biochim. Biophys. Acta* 1419:137–150 (1999)).

For the Rh-PE containing systems, the incorporation of $CPL_4$ was determined by dividing the dansyl to rhodamine ratio before the Sepharose column by that after the column multiplied by 100%. For the other systems, incorporation was determined by dividing the $CPL_4$ content by the total lipid content and multiplying by 100%.

Lipoplexes were prepared at a charge ratio of 1.5:1 (positive-to-negative) by adding 25 μL of 88 μg/mL plasmid DNA (pCMVLuc or pCMVGFP) with 25 μL of DOPE: DODAC (0.8 mM) while vortexing followed by incubation at room temperature for 30 min prior to addition to cells. Lipofectin lipoplexes were similarly prepared.

Quasi-elastic light scattering (QELS) studies were conducted employing a Nicomp Model 270 Submicron Particle Sizer operating in the vesicle mode. Freeze-fracture electron microscopy studies were performed as described by Wheeler et al., supra.

DNA for Southern analysis was extracted using a phenol: chloroform extraction following incubation of SPLP systems with 50% mouse serum. The resulting DNA was then subjected to electrophoresis through a 1% agarose gel, transferred to a nylon membrane (Amersham) and subjected to Southern analysis. The membrane was exposed to random-primed $^{32}P$-labelled PvuII restriction fragment from the luciferase gene according to current protocols. Hybridization intensities were quantified using a Phosphorimager™ SI from Molecular Dynamics. The data were converted to give amounts of intact DNA relative to undigested DNA.

Levels of PEG-$CerC_{20}$ and DOPE were determined by HPLC analyses performed by Northern Lipids, Inc, Vancouver, B.C.

3. Uptake and transfection studies. A transformed BHK cell line ($tk^-$) was used for all uptake and transfection studies. To determine the cellular uptake of SPLP, $1\times10^5$ BHK cells were seeded in each well of a 12-well plate and incubated overnight in 2 ml of complete media (DMEM containing 10% FBS) at 37° C. in 5% $CO_2$. SPLP, SPLP-$CPL_4$ in media containing 40 mM $CaCl_2$, or DOPE:DODAC lipoplexes in a volume of 200 μL were mixed with 800 μL of complete media at a final lipid dose of 20 μM and was added to the cells. Plasmid DNA concentrations corresponded to 1.4 μg/mL and 2.2 μg/mL for the SPLP systems and the lipoplexes, respectively. Cells were incubated at 37° C. for indicated periods, washed twice with PBS and lysed with 600 μL of lysis buffer (0.1% Triton X-100 in PBS). Rhodamine fluorescence was determined using a $\lambda_{ex}$ of 560 nm and a $\lambda_{em}$ of 600 nm with slit widths of 10 and 20 nm, respectively. An emission filter of 530 nm was also used. Lipid uptake was determined by comparison of the fluorescence in the lysate to that of a lipid standard and normalized to the cell number as determined by the BCA protein assay (Pierce, Rockford, Ill.). Where indicated, fluorescence micrographs were obtained using an Axiovert 100 Zeiss Fluorescent microscope (Carl Zeiss Jena GmbH) using a rhodamine filter from Omega Opticals (Brattleboro, Vt.) with the following specifications: excitation 560±20/dichroic filter 590/long pass emission 600.

The effect of $Ca^{2+}$ and $Mg^{2+}$ on lipid uptake was determined as described above with the following exceptions. BHK cells ($5\times10^4$ per well) were seeded in a 24-well plate in 1 mL of complete media and incubated overnight at 37° C. SPLP-$CPL_4$ (40 nmol) were mixed with $CaCl_2$ or $MgCl_2$ in a total volume of 100 μL. Complete media (400 μL) was added to the SPLP-$CPL_4$ resulting in final cation concentrations of 4 to 14 mM. This mixture was then added to the cells and incubated for 4 h at 37° C. Cells were then washed twice with PBS and lysed in 600 μL of lysis buffer (0.1% Triton X-100 in PBS).

Unless otherwise indicated, transfection studies were performed employing $1\times10^4$ BHK cells plated in each well of a 96-well plate in 150 μL complete media prior to overnight incubation at 37° C. in 5% $CO_2$. SPLP and SPLP-$CPL_4$ corresponding to 0.5 μg of pCMVLuc in 20 μL HBS (SPLP), or HBS containing 40 mM $CaCl_2$ (SPLP-$CPL_4$) were added to 80 μL of complete media for a plasmid concentration of 5.0 μg/mL. A transfection time of 4 h with a total incubation time of 24 h was used routinely. The transfection time is defined as the time the cells are incubated with the plasmid-containing particles whereas the total incubation time is the transfection time (after which the transfection media is replaced) plus the subsequent time the cells are incubated for prior to assaying for transgene expression. After 24 h, the cells were lysed with 100 μL of lysis buffer, and 40 μL of the lysate was transferred to a 96-well luminescence plate. Luciferase activity was determined using a Luciferase reaction kit (Promega, Madison, Wis.), a luciferase standard (Boehringer-Manheim), and a ML3200 microtiter plate luminometer from Molecular Dynamics (Chantilly, Va.). Activity was normalized to the number of cells as determined by the BCA protein assay (Pierce, Rockford, Ill.).

The transfection time course study included SPLP, SPLP-CPL, and Lipofectin (Gibco BRL, Burlington, ON) and DOPE/DODAC lipoplexes containing pCMVLuc. The lipoplexes were prepared as described earlier. After transfection times of 4, 8, and 24 h the transfection media was removed and in the case of the 4 and 8 h transfections, was replaced with complete media for a total incubation time of 24 h. At 24 h, all cells were lysed and assayed for luciferase activity and protein content (BCA assay), as described above.

SPLP-$CPL_4$, DOPE:DODAC lipoplexes and Lipofectin lipoplexes containing pCMVGFP were prepared as described for pCMVLuc. The transfections were performed as described above at a plasmid DNA dose of 5.0 μg/mL. Following incubation of the samples for 24 and 48 h, the transfection media was removed, the cells were washed, and fresh media was added to the cells. The cells were then viewed under a Zeiss fluorescence microscope. The number of cells expressing GFP were counted using a fluorescein filter (Omega Opticals) with the following specifications: excitation 475±20/dichroic filter 500/emission 535±22.5. The transfection efficiency was expressed as percentage of cells expressing GFP.

B. Results

1. Cationic PEG lipids can be inserted into preformed SPLP. Previous work has shown that SPLP exhibit lower uptake into cells and lower transfection potencies than lipoplexes (Mok, et al., *Biochim. Biophys. Acta* 1419:137–150 (1999)). It has also been shown that surface-associated cationic PEG lipids (CPL), particularly those containing four charges at the end of the PEG molecule ($CPL_4$; for structure see FIG. 8A), can dramatically enhance the uptake of LUV into cells. Further, CPL can be inserted into preformed LUV with lipid compositions similar to SPLP employing a straightforward incubation protocol. It was thus examined whether a similar procedure could be developed to insert $CPL_4$ into SPLP. SPLP containing pCMVLuc were prepared by the detergent dialysis procedure of Wheeler et al. (Gene Therapy 6:271–281 (1999)) from a lipid mixture containing 6 mol % of the cationic lipid N,N-dioleoyl-N,N-dimethyl ammonium chloride (DO- DAC), 84 mol % of the "fusogenic" helper lipid dioleoyl phosphatidylethanolamine (DOPE) and 10 mol % of a stabilizing lipid consisting of $PEG_{2000}$ attached to a ceramide (Cer) anchor (PEG-Cer). The ceramide anchor of the PEG-Cer contained a $C_{20}$ acyl chain (PEG-Cer$C_2$0) that does not readily exchange out of the vesicle, thus contributing to a highly stable SPLP system (Wheeler, et al, *Gene Therapy* 6:271–281 (1999)). The detergent dialysis procedure results in the formation of a mixture of SPLP containing one plasmid per vesicle, free plasmid, and empty vesicles. SPLP were purified by removing free plasmid and empty vesicles by DEAE column chromatography and density centrifugation, respectively, as described elsewhere (Wheeler, et al, *Gene Therapy* 6:271–281 (1999)).

Figure 8:
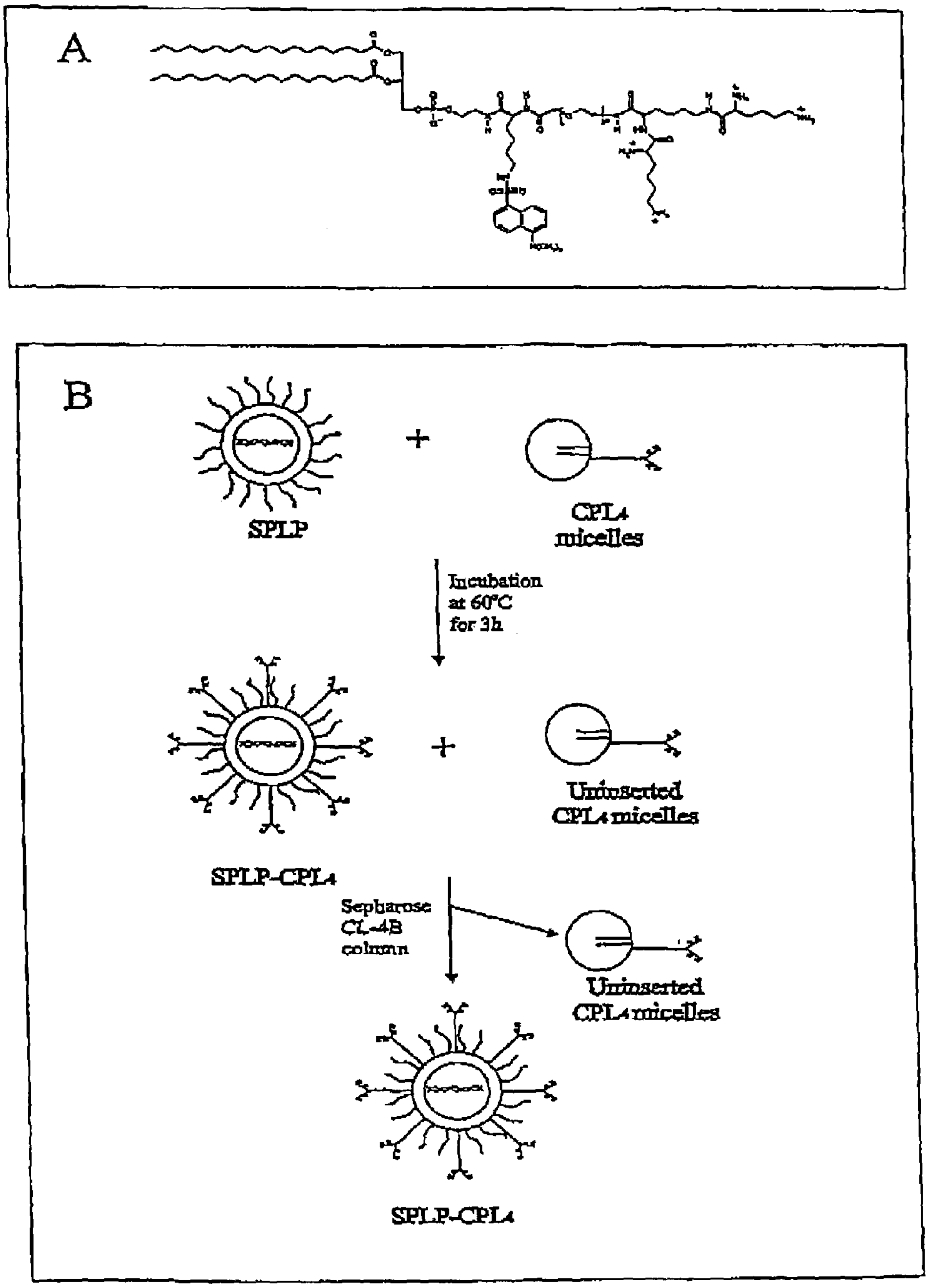
FIG. 8. Production of SPLP-$CPL_4$. A. Structure of dansylated $CPL_4$. $CPL_4$ possesses four positive charges at the end of a $PEG_{3400}$ molecule attached to a lipid achor, DSPE. B. Protocol for insertion of $CPL_4$ into preformed SPLP. The SPLP and $CPL_4$ are incubated together at 60° C. for 3 h, and unincorporated $CPL_4$ is removed using Sepharose CL-4B column chromatography. For further details see Materials and Methods, Example II.
Figure 9:
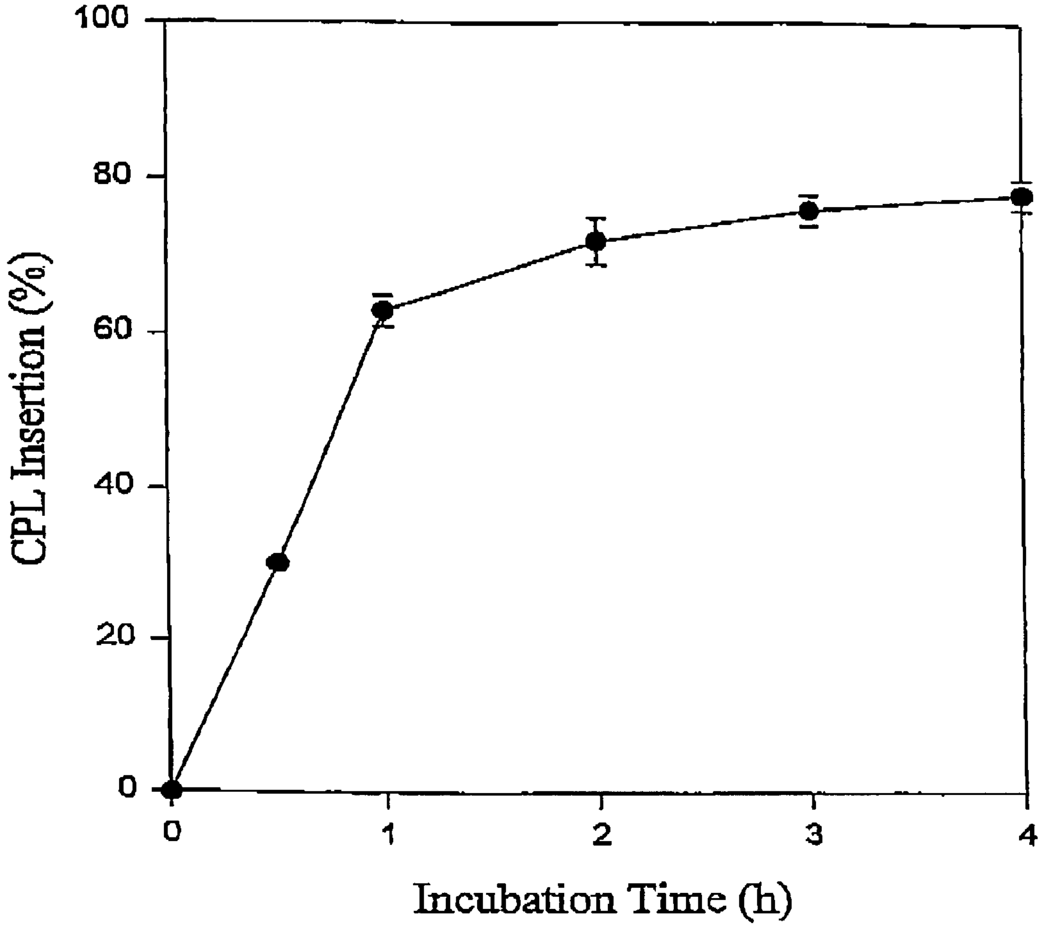
FIG. 9. Time course for the insertion of $CPL_4$ into SPLP at 60° C. Dansylated $CPL_4$ (0.3 μmol) was added to SPLP composed of 6 μmol DOPE:PEG-$CerC_{20}$:DODAC:Rh-PE (83.5:10:6:0.5; mol %) containing 360 μg pCMVLuc in a total volume of 1.5 mL and incubated at 60° C. Aliquots (250 μL) of the mixture were taken at the times indicated and unincorporated $CPL_4$ was removed employing Sepharose CL-4B column chromatography. $CPL_4$ incorporation was determined as described in Materials and Methods, Example II.

The procedure for post-insertion of $CPL_4$ into the preformed SPLP is illustrated in FIG. 8B. Purified SPLP were incubated with $CPL_4$ (~5 mol %) at 60° C. for up to 3 h and then separated from nonincorporated $CPL_4$ by column chromatography. As shown in FIG. 9, this resulted in association of up to 80% of the available $CPL_4$ with the SPLP, corresponding to 4 mol % of the total lipid in the SPLP-$CPL_4$ system.

Figure 10:
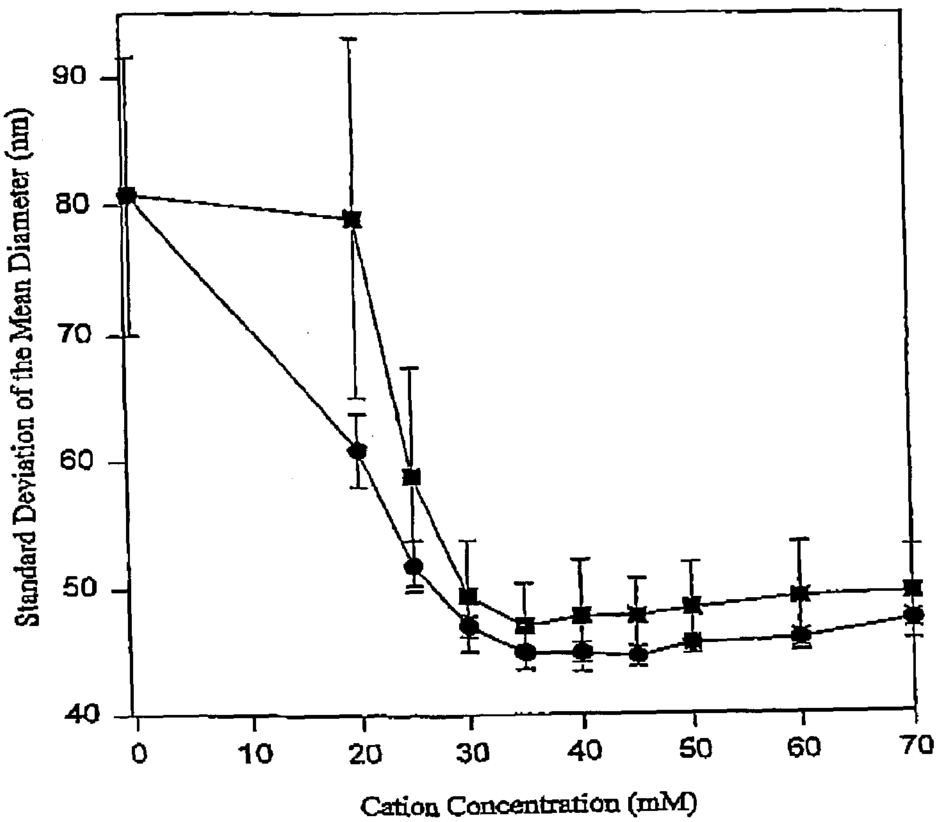
FIG. 10. Effect of cation concentration on the de-aggregation of SPLP following insertion of $CPL_4$. SPLP were prepared and 4 mol % $CPL_4$ was inserted as described in Materials and Methods, Example II. The mean diameter and standard deviation of the mean diameter of the SPLP-$CPL_4$ in the presence of increasing concentrations of $Ca^{2+}$ (●) and $Mg^{2+}$ (■) was determined by QELS. $CaCl_2$ or $MgCl_2$ from 500 mM stock solutions was added to SPLP-$CPL_4$ (180 nmol in 400 μL). The addition of $Ca^{2+}$ or $Mg^{2+}$ results in a more monodisperse preparation as indicated by a reduction in the standard deviation of the mean diameter at cation concentrations above 30 mM.
Figure 11:
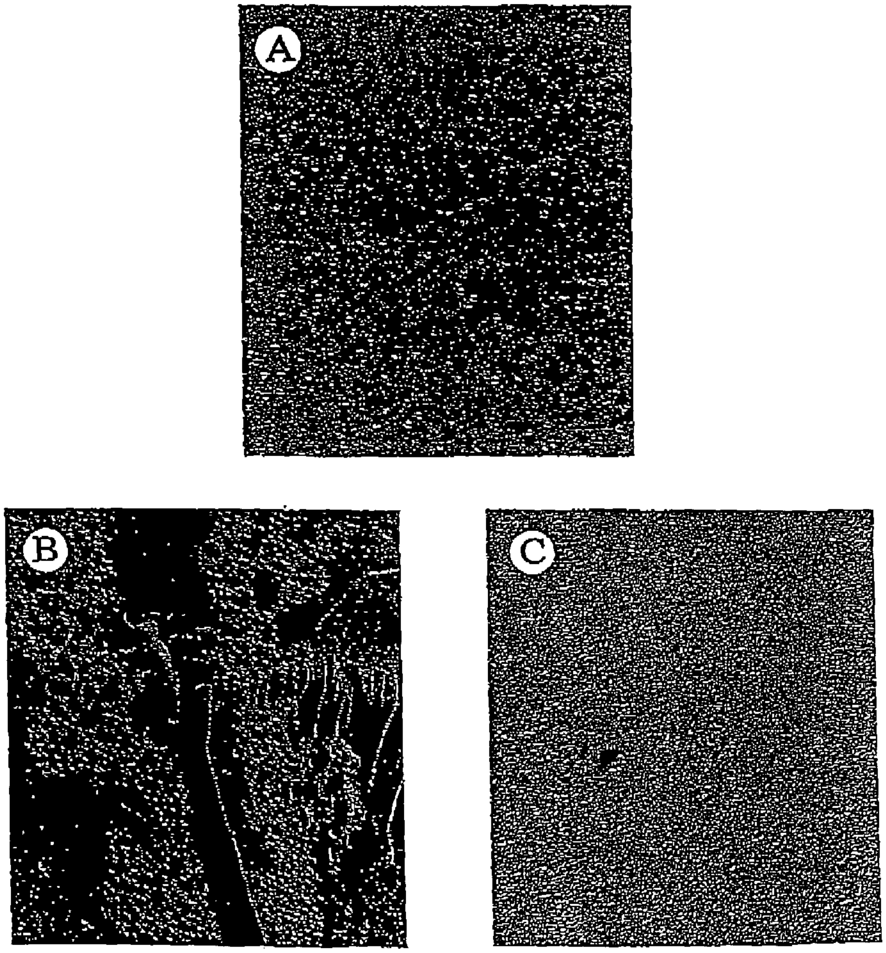
FIG. 11. Freeze-fracture electron micrographs of (A) SPLP, (B) SPLP-$CPL_4$ and (C) SPLP-$CPL_4$ in the presence of 40 mM $CaCl_2$. The SPLP-$CPL_4$ were prepared as described in Materials and Methods, Example II, and contained 4 mol % $CPL_4$. The bar in plate A corresponds to 200 nm.

2. SPLP-$CPL_4$ aggregate following insertion of $CPL_4$ and de-aggregate following addition of divalent cations. Previous work has shown that LUV containing CPL tend to aggregate and that this aggregation can be inhibited by increasing the ionic strength of the medium. It was found that SPLP-$CPL_4$ were also susceptible to aggregation, and that this aggregation could be reversed by adding NaCl, $CaCl_2$ or $MgCl_2$ to the SPLP-$CPL_4$ formulation. This effect is illustrated in FIG. 10 which shows the effect of the addition of $CaCl_2$ and $MgCl_2$ on aggregation of SPLP-$CPL_4$ as monitored by the change in the standard deviation of the mean diameter of the particles measured by quasi-elastic light scattering (QELS). For both cations the standard deviation decreased with increasing cation concentration with optimal de-aggregation occurring above 30 mM. This behaviour could also be visualized by freeze-fracture electron microscopy. As shown in FIG. 11A, freeze-fracture micrographs of SPLP reveal small monodisperse particles, whereas SPLP-$CPL_4$ prepared in the absence of $CaCl_2$ are highly aggregated (FIG. 11B). As shown in FIG. 11C, the addition of 40 mM $CaCl_2$ reverses this aggregation to produce monodisperse particles similar to the SPLP preparation.

The sizes of SPLP and SPLP-$CPL_4$ in the presence of $CaCl_2$ were compared using QELS and freeze-fracture electron microscopy. QELS studies revealed the mean diameter of SPLP and SPLP-$CPL_4$ to be 80±19 nm and 76±15 nm, respectively, whereas the freeze-fracture studies indicated diameters of 68±11 nm and 64±14 nm. These values for SPLP diameters are in close agreement with previous studies (Wheeler, et al., *Gene Therapy* 6:271–281 (1999)).

3. PEG-Cer$C_{20}$ content and stability of SPLP-$CPL_4$. The observation that $CPL_4$ can be inserted to achieve levels as high as 4 mol % of the total SPLP lipid indicates that the level of $CPL_4$ in the outer monolayer of the SPLP-$CPL_4$ is 8 mol %. Given that the initial concentration of PEG-Cer$C_{20}$ is 10 mol %, this suggests that the total levels of PEG-lipids in the outer monolayer of the SPLP-$CPL_4$ can approach 18 mol %. These levels are higher than the levels of PEG-lipids that can usually be incorporated into lipid vesicles (Woodle, et al., *Biochim. Biophys. Acta* 1113:171–199 (1992)) leading to the possibility that some of the PEG-Cer$C_{20}$ in the outer monolayer exchanged out as $CPL_4$ was inserted. This was examined by measuring the ratio of PEG-Cer$C_{20}$-to-DOPE for the SPLP before and after insertion of $CPL_4$ employing HPLC. $CPL_4$ was inserted into SPLP as described previously. Analysis following removal of nonincorporated material determined that 4 mol % $CPL_4$ (normalized to the total SPLP lipid) was inserted into the SPLP. Prior to insertion of the $CPL_4$ the PEG-Cer$C_{20}$-to-DOPE ratio was 0.091, corresponding to a PEG-Cer$C_{20}$ content of 7.6 mol %, assuming that the DOPE constituted 84 mol % of the lipid content. Following insertion of the $CPL_4$ the PEG-Cer$C_{20}$-to-DOPE ratio was found to be 0.072, indicating a PEG-Cer$C_{20}$ content of 6.0 mol %. Assuming that all of the PEG-Cer$C_{20}$ lost from the SPLP during insertion of the $CPL_4$ is lost from the outer monolayer, this indicates that the PEG-Cer$C_{20}$ content of the outer monolayer decreases from 7.6 mol % to 4.4 mol % during the insertion process. The total PEG-lipid content in the outer monolayer of the SPLP-$CPL_4$ can then be estimated to be 12.4 mol % of the outer monolayer lipid.

Figure 12:
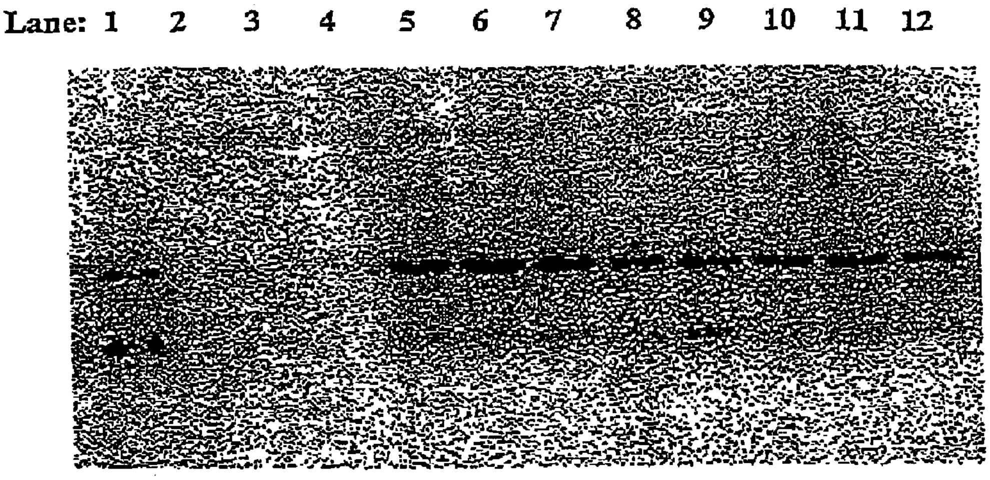
FIG. 12. Serum stability of SPLP-$CPL_4$ as assayed by Southern analysis of encapsulated plasmid. SPLP were prepared as indicated in the legend to FIG. 9 and 4 mol % of $CPL_4$ inserted using the post-insertion protocol. SPLP-$CPL_4$ containing 5 μg pCMVLuc were incubated in the presence of 50% mouse serum at 37° C. for the times indicated, an aliquot of the mixture corresponding to 1 μg of plasmid DNA was removed and plasmid DNA was extracted and subjected to Southern analysis, as described in the Materials and Methods. Lanes 1–4 indicate the behaviour of naked plasmid DNA following 0, 1, 2, and 4 h incubation times respectively; lanes 5–8 indicate the behaviour of plasmid extracted from SPLP following 0, 1, 2, and 4 h incubation times; and lanes 9–12 show the behaviour of plasmid DNA extracted from SPLP containing 4 mol % $CPL_4$ following 0, 1, 2, and 4 h incubation times.

The stability of SPLP and SPLP-$CPL_4$ following incubation in 50% mouse serum for up to 4 h is illustrated in FIG. 12. In all cases, the encapsulated plasmid DNA was fully protected from serum degradation. In contrast, essentially complete degradation of the plasmid in lipoplexes was observed within 30 min of incubation in serum.

Figure 13A:
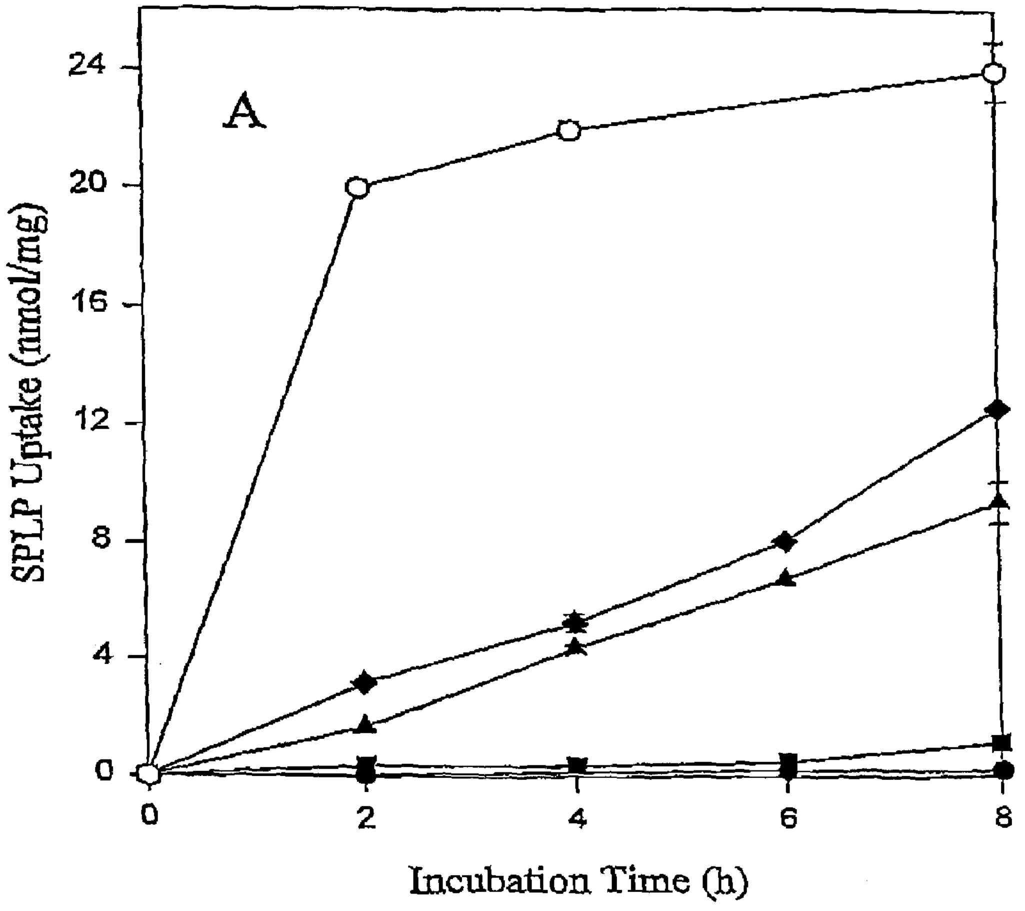
FIG. 13A. Influence of the amount of $CPL_4$ incorporated into SPLP on the uptake of SPLP-$CPL_4$ into BHK cells. Uptake of SPLP containing 0 (●), 2 (■), 3 (←), or 4 (♦) mol % $CPL_4$ was investigated; the uptake of DOPE:DODAC lipoplexes (∓) is given for comparison. The insertion of $CPL_4$ into SPLP and the preparation of lipoplexes was performed as described in Materials and Methods, Example II. The SPLP-$CPL_4$ media contained 40 mM $CaCl_2$ to prevent aggregation, addition to the BHK cells resulted in dilution of the $CaCl_2$ concentration to 8 mM. The uptake protocol involved incubation of SPLP-$CPL_4$ (20 μM total lipid) with $10^5$ BHK cells in DMEM containing 10% FBS. Following incubation, the cells were lysed and uptake of rhodamine-PE was measured as described in Materials and Methods, Example II.
Figure 13B:
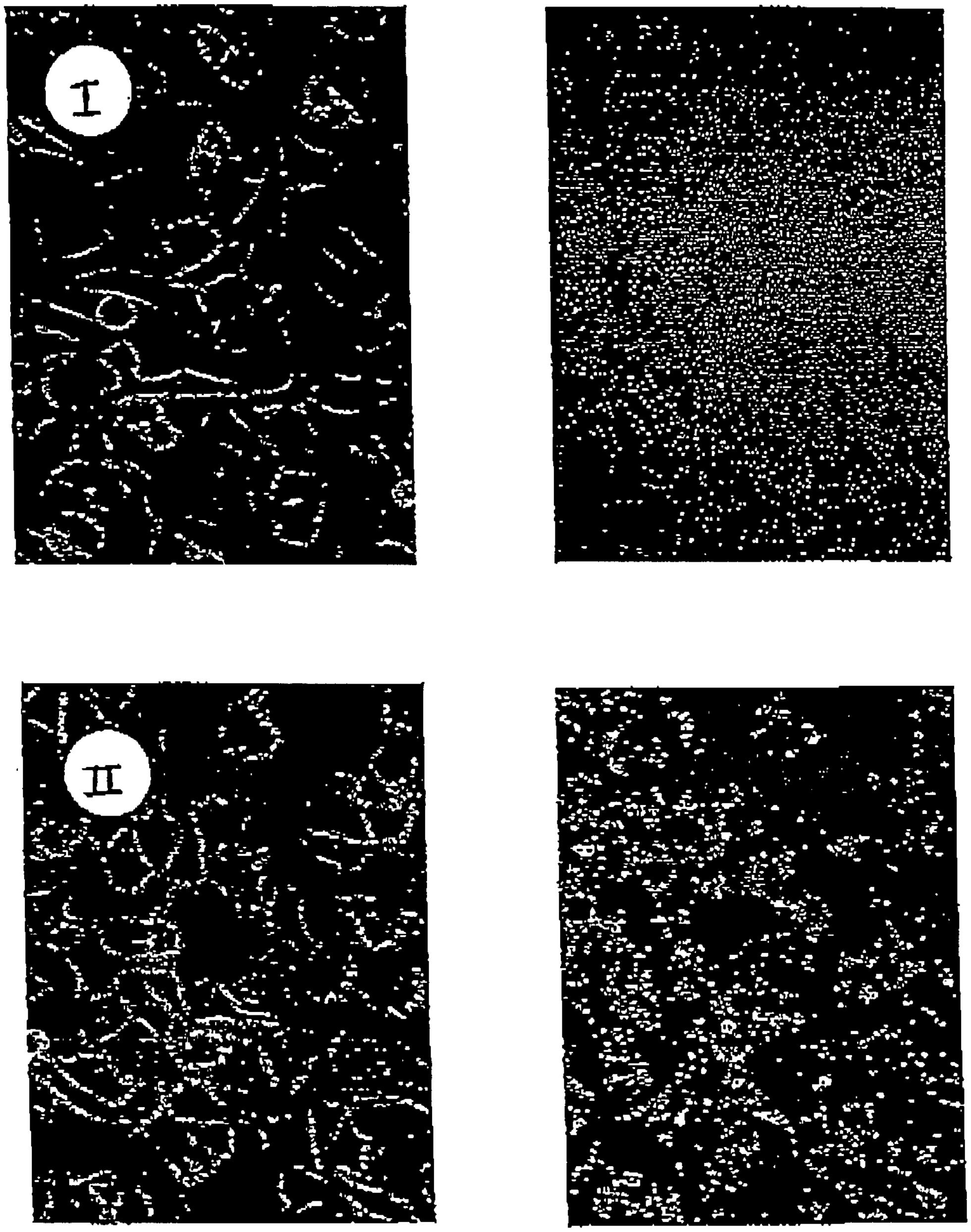
FIG. 13B. Fluorescence micrographs of BHK cells following uptake of SPLP (Panel I) and SPLP containing 4 mol % $CPL_4$ (Panel II) following a 4 h incubation. The micrographs on the left were taken in the phase contrast mode and those on the right in the (rhodamine) fluorescence mode.

4. SPLP-$CPL_4$ exhibit enhanced uptake into BHK cells and dramatically enhanced transfection potency. The next set of experiments was aimed at determining the influence of incorporated $CPL_4$ on the uptake of SPLP into BHK cells and the resulting transfection potency of the SPLP-$CPL_4$ system. SPLP containing up to 4 mol % $CPL_4$ were prepared in the presence of 40 mM $CaCl_2$ and were added to BHK cells (final $CaCl_2$ concentration 8 mM) and incubated for varying times. The cells were then assayed for associated SPLP-$CPL_4$ as indicated in the above Materials and Methods. As shown in FIG. 13A, while uptake of SPLP that contain no $CPL_4$ is minimal even after 8 h of incubation, uptake is dramatically improved for SPLP containing 3 mol % or higher levels of $CPL_4$. For example, SPLP containing 4 mol % $CPL_4$ exhibit accumulation levels at 8 h that are approximately 50-fold higher than achieved for SPLP in the absence of CPL. This enhanced uptake is visually illustrated in FIG. 13B, which shows fluorescence micrographs of BHK cells following incubation with rhodamine-labeled SPLP and SPLP-$CPL_4$ for 4 h.

Figure 14:
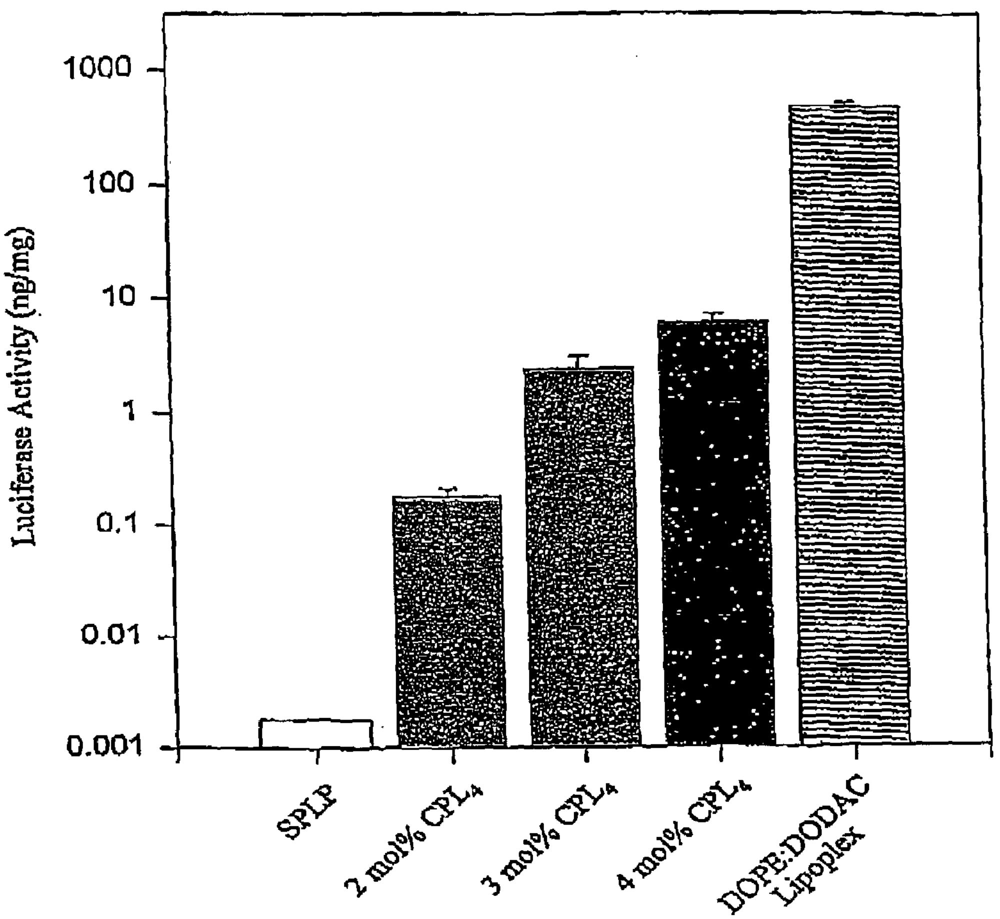
FIG. 14. Luciferase expression in BHK cells following transfection by SPLP containing various amounts of $CPL_4$. SPLP containing 2, 3 and 4 mol % $CPL_4$ were prepared employing the post-insertion process. BHK cells ($10^4$) were transfected with SPLP, SPLP-$CPL_4$ and DOPE:DODAC (1:1) lipoplexes containing 5.0 μg/mL pCMVLuc using a transfection time of 4 h and a complete incubation time of 24 h, as described in Materials and Methods, Example II. The $CaCl_2$ concentration in the SPLP-$CPL_4$-containing systems following dilution with media and addition to the BHK cells was 8 mM. After transfection the cells were lysed and the luciferase and BCA assays performed as described in Materials and Methods.

The transfection properties of SPLP, SPLP-$CPL_4$ and plasmid DNA-cationic liposome lipoplexes (DODAC/DOPE; 1:1) were examined using the transfection protocol described in the above Materials and Methods. This protocol involves incubation of BHK cells with SPLP or lipoplexes for 4 h (the transfection time) followed by replacement of media and further incubation to maximize transgene expression. The total incubation time (transfection time plus time of incubation following the media change) was kept constant at 24 h. As shown in FIG. 14, the presence of increasing amounts of $CPL_4$ resulted in dramatic increases in the transfection potency for the SPLP system. SPLP-$CPL_4$ containing 4 mol % $CPL_4$ exhibited luciferase expression levels some $3\times10^3$ higher than achieved with SPLP.

Figure 15:
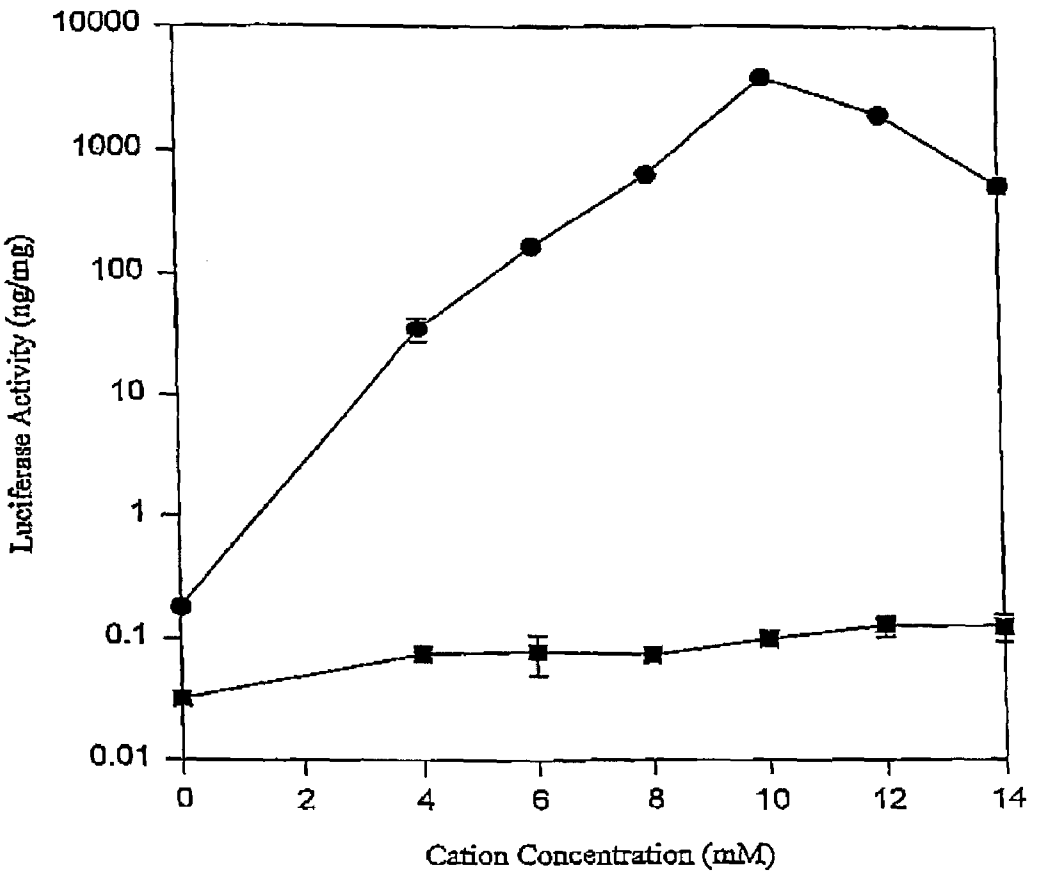
FIG. 15. Influence of $Ca^{2+}$ (●) and $Mg^2$+(■) on the transfection potency of SPLP-$CLP_4$. SPLP-$CPL_4$ containing 4 mol % $CPL_4$ were prepared by the post-insertion process as described in Materials and Methods, Example II. Increasing concentrations of $CaCl_2$ or $MgCl_2$ were added to the SPLP-$CPL_4$ (5.0 μg pCMVLuc/mL), transferred to BHK cells and incubated for 48 h in DMEM containing 10% FBS. The cells were then lysed and the luciferase activity and protein content were measured as described in Materials and Methods, Example II.

5. $Ca^{2+}$ is required for transfection activity of SPLP-$CPL_4$. Example I, supra, demonstrates that the transfection potency of SPLP is highly sensitive to the presence of $Ca^{2+}$, where the presence of 10 mM $Ca^{2+}$ enhances transfection potency several hundred-fold. It was therefore of interest to determine the influence of $Ca^{2+}$ on the transfection activity of SPLP-$CPL_4$. SPLP containing 4 mol % $CPL_4$ were incubated with BHK cells for 48 h in the presence of varying amounts of $MgCl_2$ and $CaCl_2$, and the luciferase activities were determined. As shown in FIG. 15, the transfection activity was primarily dependent on the presence of $Ca^{2+}$ in the transfection medium. At the optimum $CaCl_2$ concentration of 10 mM, SPLP-$CPL_4$ exhibited transfection potencies that were more than $10^5$ times higher than if the corresponding amount of $MgCl_2$ was present.

Figure 16:
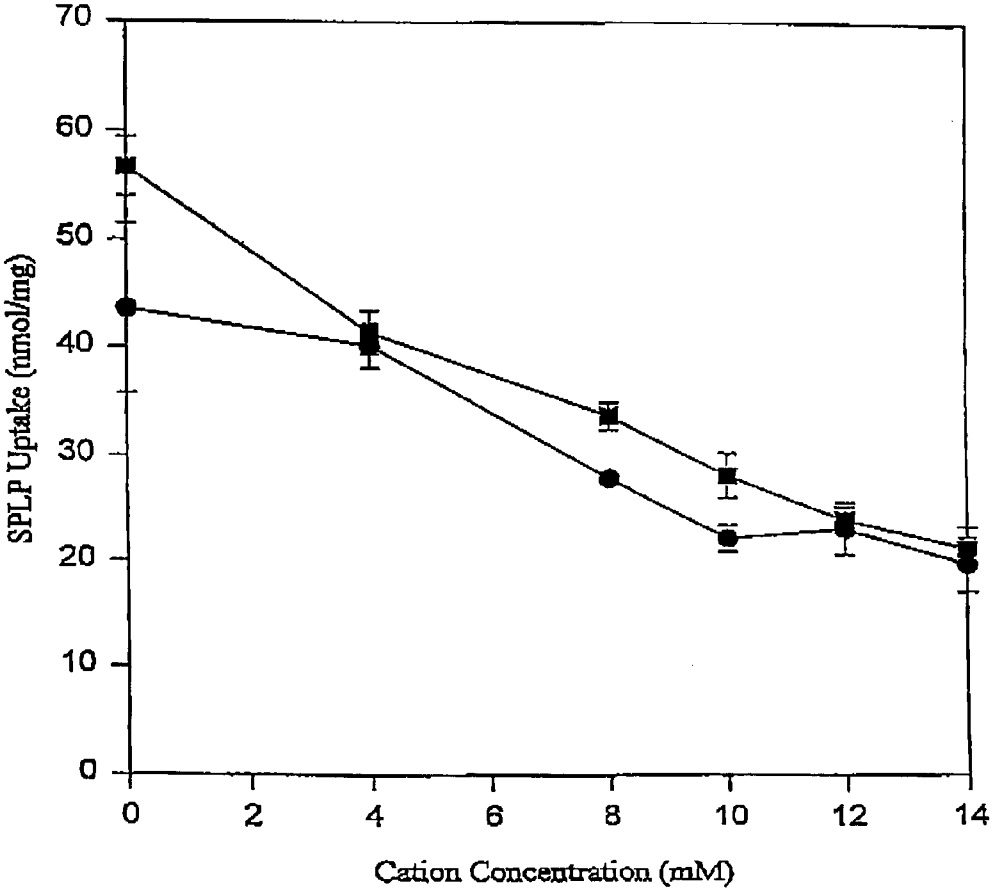
FIG. 16. Effect of $Ca^{2+}$ (●) and $Mg^2$+(■) on the uptake of SPLP-$CPL_4$ by BHK cells. SPLP-$CPL_4$ were prepared with increasing cation concentrations as indicated for FIG. 8 and incubated with BHK cells (~80 μM lipid and ~5.0 μg pCMVLuc/mL per well) for 4 h in DMEM containing 10% FBS. The cells were then lysed and the SPLP-$CPL_4$ content (as indicated by the Rh-PE lipid label) and cellular protein measured as described in Materials and Methods, Example II.

In order to determine whether the different transfection properties of SPLP-$CPL_4$ in the presence of $Ca^{2+}$ or $Mg^2$+ could be accounted for by differences in uptake into cells, the accumulation of SPLP-$CPL_4$ into BHK cells was monitored following a 4 h incubation in the presence of $MgCl_2$ or $CaCl_2$. As shown in FIG. 16, uptake of SPLP-$CPL_4$ into BHK cells is the same for both $Ca^{2+}$ and $Mg^2$+. It may be noted that SPLP-$CPL_4$ uptake decreases slightly as the concentration of divalent cations increases, likely due to the shielding of the negatively charged $CPL_4$ binding sites on the surface of BHK cells. These results are consistent with a previous study indicating that $Ca^{2+}$ has little effect on the cellular uptake of SPLP.

Figure 17:
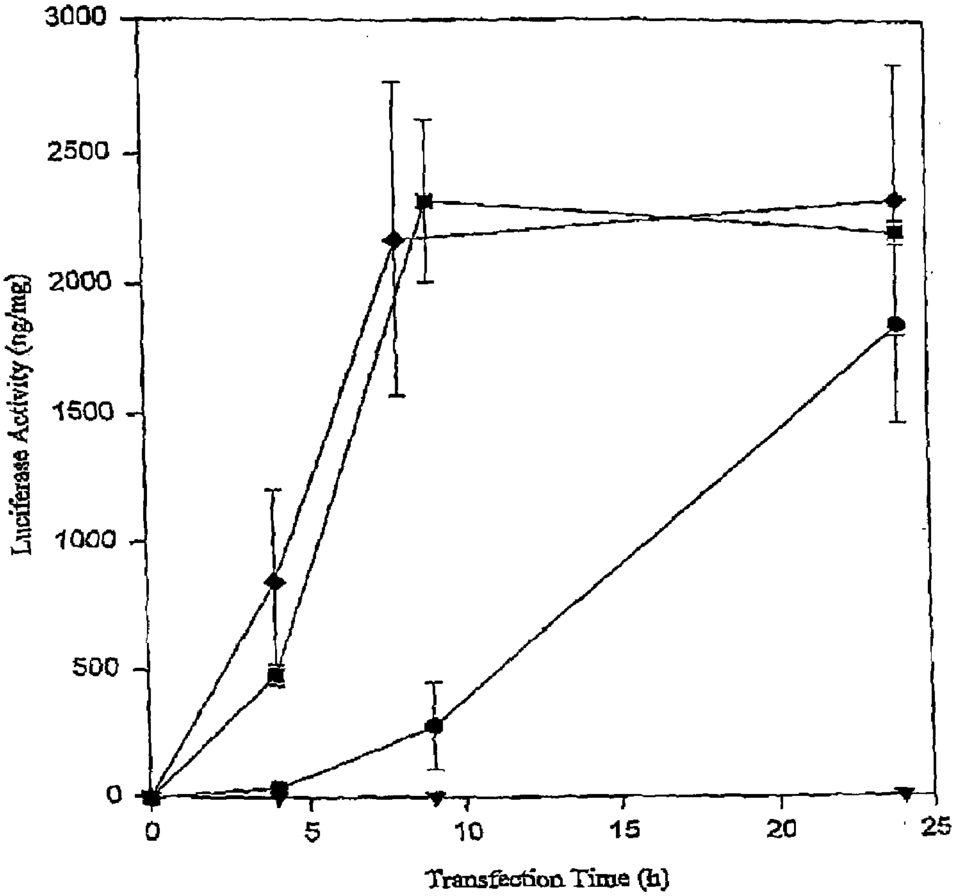
FIG. 17. Luciferase expression in BHK cells as a function of transfection time for SPLP, SPLP-$CPL_4$ and lipoplexes. SPLP-$CPL_4$ containing 4 mol % $CPL_4$ were prepared by the post-insertion process. BHK cells in DMEM and 10% FBS were incubated with SPLP, SPLP-$CPL_4$ and lipoplexes (5.0 μg/mL pCMVLuc) employing transfection times of 4, 8 and 24 h and total incubation times of 24 h. The final $CaCl_2$ concentration following addition of media was 8 mM. The cells were then assayed for luciferase activity and protein content. Luciferase activity following transfection with SPLP-$CPL_4$ (●), SPLP (▼), DOPE:DODAC lipoplexes (■), and Lipofectin lipoplexes (♦) is plotted as a function of transfection time. Lipoplexes were prepared at a charge ratio of 1.5:1.

SPLP-$CPL_4$ exhibit transfection potencies in vitro that are comparable to or greater than the transfection potencies of lipoplexes. The data presented in FIG. 14 indicate that DOPE/DODAC lipoplexes yield ~100-fold higher levels of gene expression than SPLP-$CPL_4$ when applied to BHK cells for a period of 4 h. Given that SPLP-$CPL_4$ are stable systems, uptake can conceivably continue over extended time periods. The transfection levels achieved when SPLP-$CPL_4$ or the lipoplexes were applied to BHK cells for transfection times of 4, 8 and 24 h were thus examined. Two types of lipoplexes were used, namely DOPE:DODAC (1:1) lipoplexes (charge ratio 1.5) and lipoplexes generated using the transfection reagent Lipofectin, consisting of DOPE/DOTMA (1: 1) lipoplexes at a charge ratio of 1.5. As shown in FIG. 17, the potency of SPLP-$CPL_4$ increases markedly with increased transfection times, suggesting that the rate of uptake of the SPLP-$CPL_4$ system may be a limiting factor for transfection. For the 24 h transfection time, where the cells are assayed for luciferase expression immediately after the transfection period, transfection levels are comparable to those achieved by Lipofectin or the DOPE/DODAC lipoplexes.

Figure 18A:
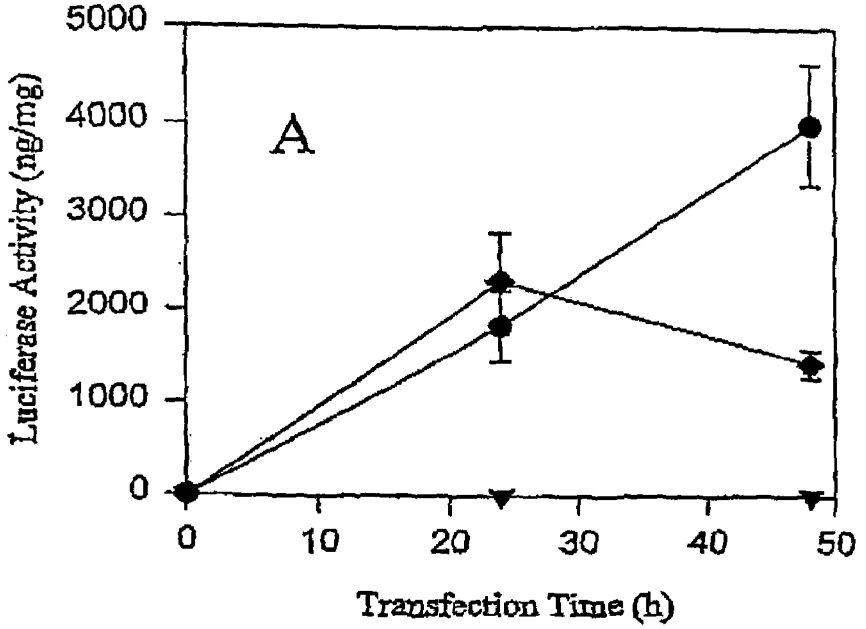
FIG. 18A. The transfection potency of SPLP-$CPL_4$ (●) containing 4 mol % $CPL_4$ and and Lipofectin lipoplexes (♦) following extended transfection times with BHK cells. SPLP-$CPL_4$ and lipoplexes were generated as indicated for FIG. 10. BHK cells were transfected in DMEM containing 10% FBS for 24 and 48 h with SPLP-$CPL_4$ and Lipofectin lipoplexes (charge ratio of 1.5:1) containing 5.0 μg/mL pCMVLuc. Following transfection the luciferase expression levels and cell protein levels were determined in the cell lysate. The luciferase activity was normalized for protein content in the lysate and plotted as a function of transfection time.

Further experiments were conducted to determine transfection levels after transfection times of 24 and 48 h with SPLP-$CPL_4$ and lipoplexes where luciferase activities were assayed immediately following the transfection period. As shown in FIG. 18A the activity of Lipofectin (DOPE:DOTMA) lipoplexes leveled off at ~2000 ng luciferase per mg of cell protein after 24 h. Similar results were obtained for the DOPE:DODAC lipoplexes. In contrast, the activity of the SPLP-$CPL_4$ formulation continued to increase as the incubation time was increased, achieving luciferase expression levels corresponding to 4000 ng per mg of cell protein at 48 h. This activity is approximately 106 times higher than observed for SPLP (in the absence of $Ca^{2+}$ ) and almost double the levels that can be achieved by Lipofectin lipoplexes.

Figure 18B:
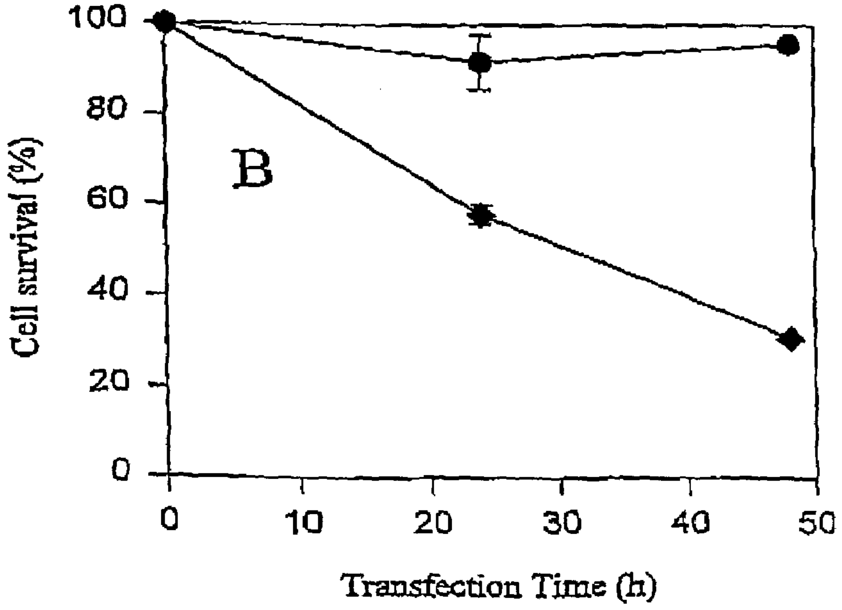
FIG. 18B. The toxicity of SPLP-$CPL_4$ (●) containing 4 mol % $CPL_4$ and and Lipofectin lipoplexes (♦) as a function of transfection time, as assayed by cell survival based on the protein concentration in the cell lysate.

6. SPLP-$CPL_4$ are nontoxic and efficient transfection agents. It is well known that lipoplexes can be toxic to cells. The SPLP-$CPL_4$ contain low levels of cationic lipid and are potentially less toxic than lipoplexes. The toxicities of SPLP-$CPL_4$ and lipoplexes were assayed by determining cell viability following a 24 h and 48 h exposure to levels of SPLP-$CPL_4$ and lipoplexes corresponding to 5.0 μg/mL plasmid, corresponding to total lipid doses of approximately 80 μM and 45 μM for SPLP-$CPL_4$ and lipoplexes, respectively. As shown in FIG. 18B, SPLP-$CPL_4$ exhibited little toxicity, whereas lipoplexes were highly toxic. Cell survival was only 30% after a 48 h incubation with Lipofectin lipoplexes, whereas 95% of the cells were viable following a 48 h incubation with SPLP-$CPL_4$.

Figure 19:
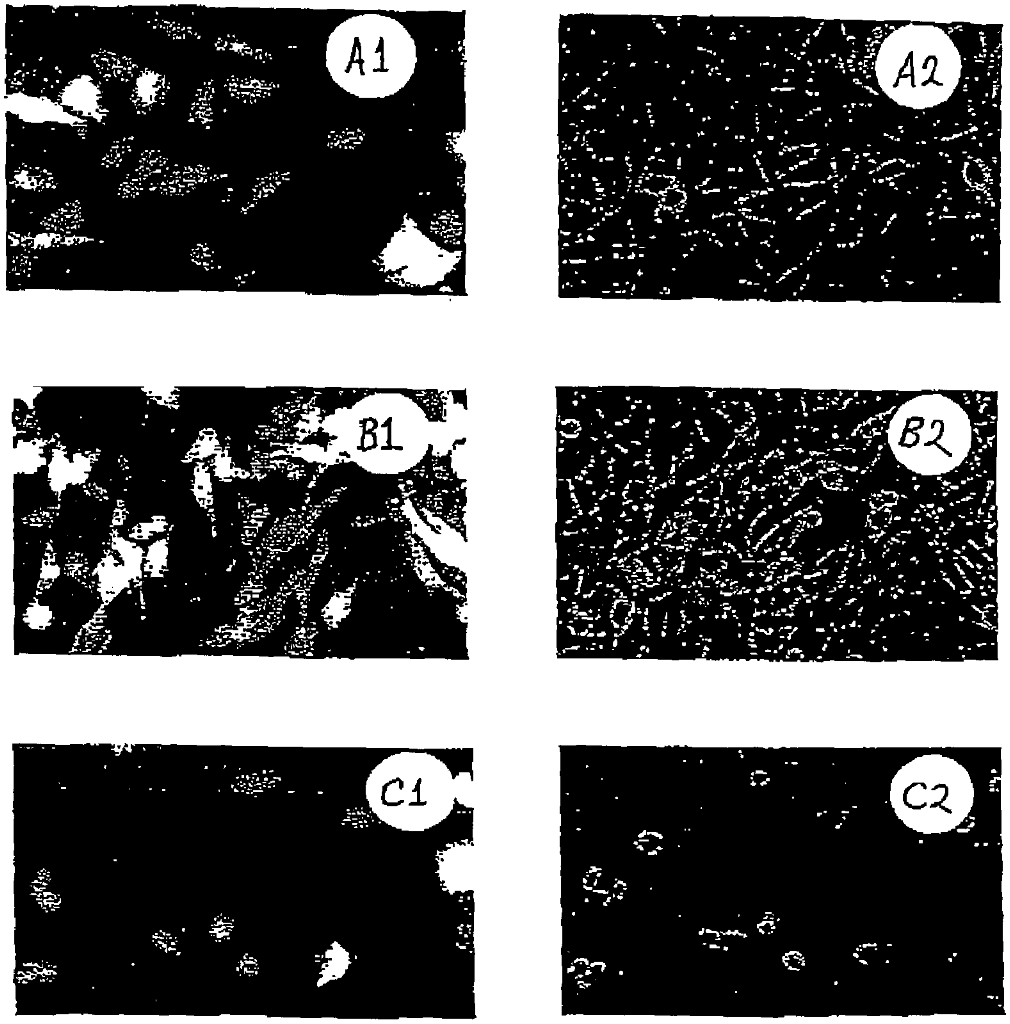
FIG. 19. Fluorescence and phase contrast micrographs of BHK cells transfected with SPLP-$CPL_4$ and lipoplexes containing a plasmid coding for GFP. Cells were transfected with SPLP-$CPL_4$ for 24 h (A1, A2) and 48 h (B1, B2) and with lipofectin for 24 h (C1, C2). SPLP and lipoplexes were prepared with pCMVGFP as described in Materials and Methods, Example II. SPLP-$CPL_4$ containing 4 mol % CPL was prepared by the post-insertion process and contained $CaCl_2$, resulting in an 8 mM $CaCl_2$ concentration in the transfection medium. BHK cells ($10^5$) were incubated with SPLP-$CPL_4$ or Lipofectin (5.0 μg/mL) in DMEM containing 10% FBS for the 24 and 48 h transfection times and examined immediately after the transfection period.
Figure 20:
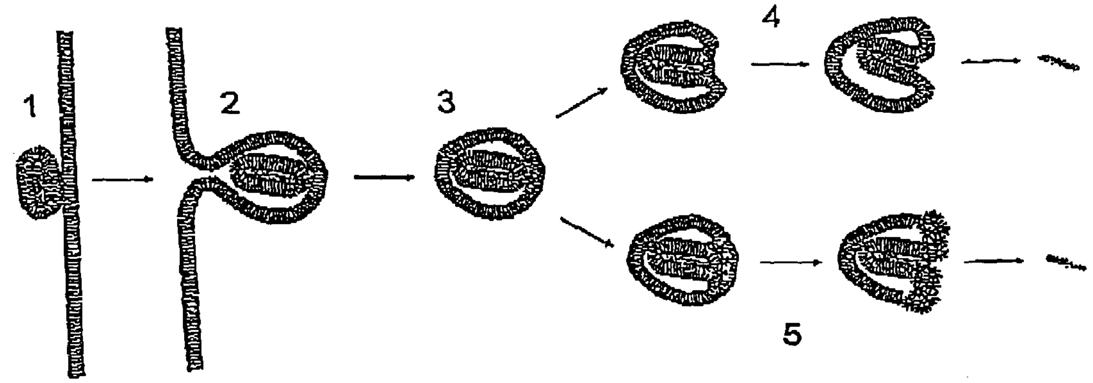
FIG. 20. Mechanism for disruption of cellular membranes mediated by cationic lipoplexes. Following binding (Step 1) and endocytosis (Step 2) into a target cell, cationic lipoplexes are transferred to late endosomal compartments (Step 3). Cationic lipids induce destabilization of the endosomal membrane leading to fusion (Step 4) of the lipoplex with the endosomal membrane, or complete remodeling of the endosomal membrane into a nonbilayer phase (Step 5).

Studies were also conducted to determine the efficiency of transfection as indicated by the proportion of cells transfected by SPLP-$CPL_4$. The proportion of transfected cells was determined by employing plasmid containing the green fluorescent protein (GFP) gene. GFP expression was detected by fluorescence microscopy. As shown in FIGS. 19A and 19B, approximately 35% of the cells at 24 h and 50% at 48 h were transfected by SPLP-$CPL_4$, with no apparent cell death. In contrast, Lipofectin lipoplexes exhibit maximum transfection efficiencies of less than 35% and only ~50% cell survival after the 24 h transfection period (FIG. 19C). Similar low transfection efficiencies and high toxicities were also seen with DOPE:DODAC lipoplexes.

C. Discussion

These results demonstrate that the incorporation of $CPL_4$ into SPLP results in improved uptake into BHK cells and dramatically enhanced transfection potencies of SPLP when $Ca^{2+}$ is present. There are three points of interest. The first concerns the chemical composition and structure of the SPLP-$CPL_4$ system and the generality of the post-insertion procedure for modifying the trophism and transfection potency of SPLP. The second concerns the relation between enhanced uptake of SPLP, the presence of $Ca^{2+}$ and the transfection activities observed. Finally, it is of interest to compare the properties of the SPLP-$CPL_4$ system with lipoplexes. Each of these areas is addressed below in turn.

The results presented here demonstrate that the cationic PEG lipid $CPL_4$ can be inserted into preformed SPLP employing a simple process involving incubation at 60° C. The ability to insert $CPL_4$ to levels corresponding, for example, to about 8 mol % of the total lipid in the SPLP outer monolayer is consistent with results of other workers demonstrating that PEG-PE can be inserted into preformed LUV employing a similar incubation protocol, resulting in systems exhibiting extended circulation lifetimes (Uster, et al., *FEBS Lett.* 386:243–246 (1996)). It is also consistent with previous results showing that $CPL_4$ can be inserted into preformed LUV with a lipid composition similar to the SPLP system. The total levels of PEG-lipids achieved in the outer monolayer (12.4 mol %) are high given that maximum levels of incorporation of PEG-lipids into LUV are commonly 7–10 mol % (Woodle, et al., *Biochim. Biophys. Acta* 1113:171–199 (1992)). However, a number of authors have reported that PEG-lipids can be incorporated into LUV to levels as high as 15 mol % before lytic effects are observed (Edwards, et al., *Biophys. J.* 73:258–266 (1997); Kenworthy, et al., *Biophys. J.* 68:1903–1920 (1995); Hristova, et al., *Macromolecules* 28:7693–7699 (1995)). These include cryo-electron microscopy studies which indicate that structural changes (from spheres to discs) are only observed for distearoylphosphatidylcholine (DSPC) liposomes at PEG-PE levels above 12 mol %, with lytic effects observed above 15 mol % (Edwards, et al., *Biophys. J* 73:258–266 (1997)). Similarly, X-ray studies indicate that nonbilayer micellar structures are only observed for PEG-lipid levels above 15 mol % (Kenworthy, et al., *Biophys. J.* 68:1903–1920 (1995); Hristova, et al., *Macromolecules* 28:7693–7699 (1995)).

The tendency for the SPLP-$CPL_4$ system to aggregate following insertion of the $CPL_4$ is consistent with previous observations that LUV containing $CPL_4$ also aggregate. The reason for this aggregation is not currently understood, although two general points can be made. First, the interaction is likely due to electrostatic interactions between vesicles given the inhibition of aggregation at higher ionic strengths. Second, the aggregation is not a consequence of the post-insertion process itself as such aggregation is also observed for LUV containing $CPL_4$, where the $CPL_4$ was present in the lipid mixture from which the LUV were formed. It is possible that the cationic headgroup interacts with opposed membranes at the level of the phospholipid phosphate group. Alternatively, the aggregation phenomenon may be related to the ability of PEG coatings to adopt a conformation that is able to bind proteins such as streptavidin (Sheth, et al., *Proc. Natl. Acad. Sci. USA* 94:8399–8404 (1997)).

The second point of discussion concerns the mechanism whereby $CPL_4$ increases the transfection potency of the SPLP system. A number of studies have indicated that the cationic lipids contained in lipoplex systems play a direct role in stimulating uptake into cells (Miller, et al., *Biochemistry* 37:12875–12883 (1998)) and that this uptake arises due to the positive charge on the lipoplexes (van der Woude, et al., *Biochim Biophys Acta* 1240:34–40 (1995)). It has been suggested that heparin sulfonated proteoglycans on the cell surface play a primary role in this process (Mislick, et al., *Proc. Natl. Acad. Sci. USA* 93:12349–12354 (1996); Mounkes, et al., *J. Biol. Chem.* 273:26164–26170 (1998)). Enhanced uptake of SPLP following addition of the $CPL_4$ could be due to similar mechanisms, although the increase in transfection potency is largely dependent on the additional presence of $Ca^{2+}$. Example I shows that the presence of $Ca^{2+}$ results in an increase in SPLP transfection potency of 600 fold, and that this increase results from an ability of $Ca^{2+}$ to assist in destabilizing the endosomal membrane following uptake, rather than from an increase in uptake. It is therefore possible that the observed improvements in transfection potency for SPLP-$CPL_4$ over SPLP result from improvements in uptake mediated by the $CPL_4$ coupled with enhanced abilities to destabilize the endosomal membrane due to the presence of $Ca^{2+}$. In this regard, the transfection potency of SPLP-$CPL_4$ (in the presence of $Ca^{2+}$) is increased by a factor of ~$10^4$ (FIG. 14) in comparison to the transfection potency of SPLP in the absence of $Ca^{2+}$. This could be accounted for by an increase in uptake of SPLP into BHK cells by approximately 50-fold due to the presence of 4 mol % $CPL_4$ (FIG. 13A, 4 h incubation) multiplied by a factor of ~600 due to the presence of $Ca^{2+}$.

The final area of discussion concerns the advantages of the SPLP-$CPL_4$ system over other nonviral vectors, which include the well-defined modular nature of the SPLP-$CPL_4$ system as well as toxicity and potency issues. First, SPLP-$CPL_4$ are small, homogeneous, stable systems containing one plasmid per particle (Wheeler, et al., *Gene Therapy* 6:271–281 (1999)), in contrast with other nonviral systems such as lipoplexes, which are large, heterogeneous, unstable systems containing ill-defined numbers of plasmids per particle. An important point is that SPLP are basic components of more sophisticated systems, such as SPLP-$CPL_4$, that can be constructed in a modular fashion. For example, post-insertion of PEG-lipids containing specific targeting ligands in place of the cationic groups of CPL should result in SPLP that are specifically targeted to particular cells and tissues. With regard to toxicity, SPLP-$CPL_4$ are markedly less toxic to BHK cells in tissue culture than are lipoplexes. This is presumably related to the low proportions of cationic lipid contained in SPLP as compared to lipoplexes. Finally, SPLP without $CPL_4$ or $Ca^{2+}$ exhibit transfection properties in vivo following systemic administration that are already superior to the transfection properties of plasmid DNA-cationic lipid complexes or naked plasmid DNA. The results presented here suggest that further significant gains can be expected through the use of ligands that encourage SPLP uptake into cells and methods leading to local increases in $Ca^{2+}$ concentrations.

In summary, the results presented here demonstrate that a cationic PEG lipid can be post-inserted into SPLP, resulting in well-defined SPLP-$CPL_4$ systems that exhibit improved uptake into BHK cells in vitro. In the presence of $Ca^{2+}$ SPLP-$CPL_4$ systems give rise to transfection potencies that are increased by up to 1 $0^6$-fold as compared to SPLP in the absence of $Ca^{2+}$. These results indicate that the SPLP system is a nontoxic, highly transfection potent entity following uptake into cells and indicates that SPLP targeted to cell-surface ligands that undergo endocytosis should lead to significant enhancement of transfection potency in vivo.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A nucleic acid-lipid particle composition for introducing a nucleic acid into a cell, said particle composition comprising:

(a) a nucleic acid-lipid particle comPrising a cationic lipid, a conjugated lipid that inhibits aggregation of particles, and a nucleic acid, wherein said nucleic acid is encapsulated in a lipid bilayer of said nucleic acid-lipid particle, and wherein said conjugated lipid that inhibits aggregation of particles is a member selected from the group consisting of a PEG-lipid, an ATTA-lipid and a cationic-polymer-lipid conjugate having the formula $$A\text{-}W\text{-}Y \qquad I$$

wherein:

A is a lipid moiety;

W is a hydrophilic polymer; and

Y is a polycationic moiety; and (b) an endosomal membrane destabilizer, wherein said endosomal membrane destabilizer is $Ca^{++}$ ion.

2. The nucleic acidlipid particle composition of claim 1, wherein said endosomal membrane destabilizer is outside said nucleic acid-lipid particle.

3. The nucleic acid-lipid particle composition of claim 1, wherein said endosomal membrane destabilizer is both outside and inside said nucleic acid-lipid particle.

4. The nucleic acid-lipid particle composition of claim 1, wherein the concentration of $Ca^{++}$ ion is from about 1mM to about 20 mM.

5. The nucleic acid-lipid particle composition of claim 4, wherein the concentration of $Ca^{++}$ ion is from about 1 mM to about 20 mM.

6. The nucleic acid-lipid particle composition of claim 1, wherein said particle has a median diameter of less than about 150 nm.

7. The nucleic acid-lipid particle composition of claim 1, wherein said cationic lipid is a member selected from the group consisting of N,N-dioleyl-N,N-dimethylammonium chloride (DODAC), N,N-distearyl-N,N-dimethylammonium bromide (DDAB), N-(1-(2,3-dioleoyloxyl)propyl)-N,N,N-trimethylammonium chloride (DOTAP), N-(1-(2,3-dioleyloxy)propyl)-N,N,N-trimethylammonium chloride (DOTMA), and N,N-dimethyl-2,3-dioleyloxy)propylamine (DODMA), and combinations thereof.

8. The nucleic acid-lipid particle composition of claim 1, wherein said particle further comprises an additional noncationic lipid.

9. The nucleic acid-lipid particle composition of claim 8, wherein said noncationic lipid is selected from the group consisting of DOPE, POPC, and EPC.

10. The nucleic acid-lipid particle composition of claim 1, wherein said particle comprises a functional group that facilitates $Ca^{++}$ ion chelation.

11. The nucleic acid-lipid particle composition of claim 1, wherein said conjugated lipid that inhibits aggregation of particles has the formula $$A\text{-}W\text{-}Y \qquad \text{I}$$

wherein:

A is a lipid moiety;

W is a hydrophilic polymer; and

Y is a polycationic moiety.

12. The nucleic acid-lipid particle composition of claim 11, wherein W is a polymer selected from the group consisting of PEG, polymide, polylactic acid, polyglycolic acid, polylactic acid/polyglycolic acid copolymers and combinations thereof, said polymer having a molecular weight of about 250 to about 7000 daltons.

13. The nucleic acid-lipid particle composition of claim 11, wherein Y has at least 4 positive charges at a selected pH.

14. The nucleic acid-lipid particle composition of claim 11, wherein Y is a member selected from the group consisting of lysine, arginine, asparagine, glutamine, derivatives thereof and combinations thereof.

15. The nucleic acid-lipid particle composition of claim 11, wherein A is a member selected from the group consisting of a diacylglycerolyl moiety, a dialkylglycerolyl moiety, a N-N-dialkylamino moiety, a 1,2-diacyloxy-3-aminopropane moiety and a 1,2-dialkyl-3-aminopropane moiety.

16. The nucleic acid-lipid particle composition of claim 11, wherein W is PEG.

17. The nucleic acid-lipid particle composition of claim 11, wherein W is a polyamide polymer.

18. The nucleic acid-lipid particle composition of claim 11, wherein W has a molecular weight of about 250 to about 2000 daltons.

19. The nucleic acid-lipid particle composition of claim 16, having the general structure of Formula II:

$$A-(X-(CH_2-CH_2-O)_n-Z)-Y \qquad \text{II}$$

wherein

X is a member selected from the group consisting of a single bond or a functional group covalently attaching said lipid to at least one ethylene oxide unit;

Z is a member selected from the group consisting of a single bond or a functional group covalently attaching said at least one ethylene oxide unit to a cationic group; and n is an integer having a value of between about 6 to about 50.

20. The nucleic acid-lipid particle composition of claim 19, wherein X is a member selected from the group consisting of a single bond, phosphatidylethanolamino, phosphatidylethanolamido, phosphoro, phospho, phosphatidylethanolamino, phosphoethanolamido, carbonyl, carbamate, carboxyl, carbonate, amido, thioamido, oxygen, sulfur and NR, wherein R is a hydrogen or alkyl group.

21. The nucleic acid-lipid particle composition of claim 19, wherein

Z is a member selected from the group consisting of a single bond, phosphatidylethanolamino, phosphatidylethanolamido, phosphoro, phospho, phosphoethanolamino, phosphoethanolamido, carbonyl, carbamate, carboxyl, carbonate, amido, thioamido, oxygen, sulfur and NR, wherein R is a hydrogen or alkyl group.

22. The nucleic acid-lipid particle composition of claim 19, wherein

A is a diacylglycerolyl moiety;

X is a phosphoethanolamido;

Z is NR, wherein R is a hydrogen atom; and

Y is a member selected from the group consisting of about 1 to about 10 basic amino acids or derivatives thereof.

23. The nucleic acid-lipid particle composition of claim 22, wherein

A is a diacylgercerolyl moiety having 2 fatty acyl chains, wherein each acyl chain is independently between 2 and 30 carbons in length and is either saturated or has varying degrees of saturation.

24. The nucleic acid-lipid particle of composition of claim 1 or claim 19, wherein Y comprises a member selected from the group consisting of lysine, arginine, asparagine, glutamine, derivatives thereof and combinations thereof.

25. The nucleic acid-lipid particle composition of claim 22, wherein

A is a diacylgercerolyl moiety having 2 fatty acyl chains, wherein each acyl chain is a saturated C-18 carbon chain; and Y is a cationic group having 4 lysine residues or derivatives thereof.

26. The nucleic acid-lipid particle composition of claim 1, said conjugated lipid that inhibits aggregation of particles is a PEG-lipid.

27. The nucleic acid-lipid particle composition of claim 26, wherein said PEG-lipid is PEG-ceramide.

28. The nucleic acid-lipid particle composition of claim 27, wherein the ceramide of said PEG-ceramide comprises a fatty acid group having about 8 to about 20 carbon atoms.

29. The nucleic acid-lipid particle composition of claim 27, wherein said PEG-lipid is PEG-phosphatidylethanolamine.

30. The nucleic acid-lipid particle composition of claim 1, wherein said conjugated lipid that inhibits aggregation of particles is an ATTA-lipid.

31. The nucleic acid-lipid particle composition of claim 1, wherein said nucleic acid is selected from the group consisting of a plasmid, an antisense oligonucleotide, and a ribozyme.

32. A method of introducing a nucleic acid into a cell, said method comprising:

contacting said cell with a nucleic acid-lipid particle composition, said particle composition comprising:

(a) a nucleic acid-lipid particle comprising a cationic lipid, a conjugated lipid that inhibits aggregation of particles, and a nucleic acid, wherein said nucleic acid is encapsulated in a lipid bilayer of said nucleic acid-lipid particle, and wherein said conjugated lipid that inhibits aggregation of particles is a member selected from the group consisting of a PEG-lipid, an ATTA-lipid and a cationic-polymer-lipid conjugate having the formula $$A\text{-}W\text{-}Y \qquad \text{I}$$

wherein

A is a lipid moiety;

W is a hydrophilic polymer; and

Y is a polycationic moiety; and (b) an endosomal membrane destabilizer, wherein said endosomal membrane destabilizer is $Ca^{++}$ ion.

33. The method of introducing a nucleic acid into a cell of claim 32, wherein said endosomal membrane destabilizer is outside said nucleic acid-lipid particle.

34. The method of introducing a nucleic acid into a cell of claim 32, wherein said endosomal membrane destabilizer is $Ca^{++}$ ion.

35. The method of introducing a nucleic acid into a cell of claim 34, wherein the concentration of $Ca^{++}$ ion is from about 0.1 mM to about 100 mM.

36. The method of introducing a nucleic acid into a cell of claim 35, wherein the concentration of $Ca^{++}$ ion is from about 1 mM to about 20 mM.

37. The method of introducing a nucleic acid into a cell of claim 32, wherein said particle has a median diameter of less than about 150 nm.

38. The method of introducing a nucleic acid into a cell of claim 32, wherein said cationic lipid is a member selected from a group consisting of N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), and N,N-dimethyl-2,3-dioleyloxy)propylamine (DODMA) and combinations thereof.

39. The method of introducing a nucleic acid into a cell of claim 32, wherein said particle further comprises an additional noncationic lipid.

40. The method of introducing a nucleic acid into a cell of claim 39, wherein said noncationic lipid is selected from the group consisting of DOPE, POPC, and EPC.

41. The method of introducing a nucleic acid into a cell of claim 32, wherein said particle comprises a functional group that facilitates $Ca^{++}$ ion chelation.

42. The method of introducing a nucleic acid into a cell of claim 32, wherein said conjugated lipid that inhibits aggregation of particles has the formula $$A\text{-}W\text{-}Y \qquad \text{I}$$

wherein

A is a lipid moiety;

W is a hydrophilic polymer; and

Y is a polycationic moiety.

43. The method of introducing a nucleic acid into a cell of claim 42, wherein W is a polymer selected from the group consisting of PEG, polyamide, polylactic acid, polyglycolic acid, polylactic acid/polyglycolic acid copolymers and combinations thereof, said polymer having a molecular weight of about 250 to about 7000 daltons.

44. The method of introducing a nucleic acid into a cell of claim 42, wherein Y has at least 4 positive charges at a selected pH.

45. The method of introducing a nucleic acid into a cell of claim 42, wherein Y is a member selected from the group consisting of lysine, arginine, asparagine, glutamine, derivatives thereof and combinations thereof.

46. The method of introducing a nucleic acid into a cell of claim 42, wherein A is a member selected from the group consisting of a diacyiglycerolyl moiety, a dialkylglycerolyl moiety, a N-N-dialkylamino moiety, a 1,2-diacyloxy-3-aminopropane moiety and a 1,2-diakyl-3-aminopropane moiety.

47. The method of introducing a nucleic acid into a cell of claim 42, wherein W is PEG.

48. The method of introducing a nucleic acid into a cell of claim 42, wherein W is a polyamide polymer.

49. The method of introducing a nucleic acid into a cell of claim 42, wherein W has a molecular weight of about 250 to 2000 daltons.

50. The method of introducing a nucleic acid into a cell of claim 47, having the general structure of Formula II:

$$A-\!\left(X-(CH_2-CH_2-O)_n-Z\right)\!-Y \qquad \text{II}$$

wherein

X is a member selected from the group consisting of a single bond or a functional group covalently attaching said lipid to at least one ethylene oxide unit;

Z is a member selected from the group consisting of a single bond or a functional group covalently attaching said at least one ethylene oxide unit to a cationic group; and n is an integer having a value of between about 5 to about 50.

51. The method of introducing a nucleic acid into a cell of claim 50, wherein X is a member selected from the group consisting of a single bond, phosphatidylethanolamino, phosphatidylethanolamido, phosphoro, phospho, phosphoethanolamino, phosphoethanolamido, carbonyl, carbamate, carboxyl, carbonate, amido, thioamido, oxygen, sulfur and NR, wherein R is a hydrogen or alkyl group.

52. The method of introducing a nucleic acid into a cell of claim 50, wherein Z is a member selected from a group consisting of a single bond, phosphatidylethanolamino, phosphatidylethanolamido, phosphoro, phospho, phosphoethanolamino, phosphoethanolamido, carbonyl, carbamate, carboxyl, carbonate, amido, thioamido, oxygen, sulfur and NR, wherein R is a hydrogen or alkyl group.

53. The method of introducing a nucleic acid into a cell of claim 50, wherein A is a diacylglycerolyl moiety;

X is phosphoethanolamido;

Z is NR, wherein R is a hydrogen atom; and

Y is a member selected from the group consisting of about 1 to about 10 basic amino acids or derivatives thereof.

54. The method of introducing a nucleic acid into a cell of claim 53, wherein A is a diacylgercerolyl moiety having 2 fatty acyl chains, wherein each acyl chain is independently between 2 and 30 carbons in length and is either saturated or has varying degrees of saturation.

55. The method of introducing a nucleic acid into a cell of claim 32 or claim 50, wherein Y comprises a member selected from the group consisting of lysine, arginine, asparagine, glutamine, derivatives thereof and combinations thereof.

56. The method of introducing a nucleic acid into a cell of claim 53, wherein A is a diacylgercerolyl moiety having 2 fatty acyl chains, wherein each acyl chain is a saturated C-18 carbon chain; and Y is a cationic group having 4 lysine residues or derivatives thereof.

57. The method of introducing a nucleic acid into a cell of claim 32, wherein said conjugated lipid that inhibits aggregation of particles is a PEG-lipid.

58. The method of introducing a nucleic acid into a cell of claim 57, wherein said PEG-lipid is PEG ceramide.

59. The method of introducing a nucleic acid into a cell of claim 58, wherein the ceramide of said PEG-ceramide comprises a fatty acid group having about 8 to about 20 carbon atoms.

60. The method of introducing a nucleic acid into a cell of claim 58, wherein said PEG-lipid is PEG-phosphatidylethanolamine.

61. The method of introducing a nucleic acid into a cell of claim 32, wherein said conjugated lipid that inhibits aggregation of particles is an ATTA-lipid.

62. The method of introducing a nucleic acid into a cell of claim 32, wherein said nucleic acid is selected from the group consisting of a plasmid, an antisense oligonucleotide, and a ribozyme.

* * * * *